US008679492B2

(12) United States Patent
Blein et al.

(10) Patent No.: US 8,679,492 B2
(45) Date of Patent: Mar. 25, 2014

(54) HUMANIZED ANTIBODIES THAT BIND TO CD19 AND THEIR USES

(75) Inventors: Stanislas Blein, La Chaux-de-Fonds (CH); Darko Skegro, La Chaux-de-Fonds (CH); Christophe Debonneville, La Chaux-de-Fonds (CH); Martin Bertschinger, La Chaux-de-Fonds (CH)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 634 days.

(21) Appl. No.: 12/710,442

(22) Filed: Feb. 23, 2010

(65) Prior Publication Data

US 2010/0215651 A1    Aug. 26, 2010

Related U.S. Application Data

(60) Provisional application No. 61/154,524, filed on Feb. 23, 2009.

(51) Int. Cl.
*A61K 39/395* (2006.01)
*A61P 35/02* (2006.01)
*C07K 16/00* (2006.01)

(52) U.S. Cl.
USPC ............... 424/133.1; 424/178.1; 435/328; 530/387.3; 530/391.7

(58) Field of Classification Search
None
See application file for complete search history.

(56) References Cited

U.S. PATENT DOCUMENTS

| | | | |
|---|---|---|---|
| 5,571,894 A | 11/1996 | Wels et al. | |
| 5,587,458 A | 12/1996 | King et al. | |
| 5,624,821 A | 4/1997 | Winter et al. | |
| 5,641,870 A | 6/1997 | Rinderknecht et al. | |
| 5,648,260 A | 7/1997 | Winter et al. | |
| 5,677,425 A | 10/1997 | Bodmer et al. | |
| 5,869,046 A | 2/1999 | Presta et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 | 8/2001 | Ward | |
| 7,446,179 B2* | 11/2008 | Jensen et al. | 530/387.3 |
| 2003/0194406 A1* | 10/2003 | Reinhard et al. | 424/155.1 |
| 2004/0002587 A1* | 1/2004 | Watkins et al. | 530/388.15 |
| 2006/0263357 A1* | 11/2006 | Tedder et al. | 424/144.1 |

FOREIGN PATENT DOCUMENTS

| | | | |
|---|---|---|---|
| WO | 93/16185 A2 | 8/1993 | |
| WO | 94/13804 A1 | 6/1994 | |
| WO | 94/29351 A2 | 12/1994 | |
| WO | 00/42072 A2 | 7/2000 | |
| WO | 03/035835 | 5/2003 | |
| WO | WO 2006089133 A2 * | 8/2006 | |

OTHER PUBLICATIONS

Lewin. Genes IV. Oxford University Press, p. 810, 1990.*
Rudikoff, Giusti, Cook, and Scharff. Single amino acid substitution altering antigen-binding specificity. Proceedings of the National Academy of Science, 1982. vol. 79, p. 1979-1983.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Chen, Wiesmann, Fuh, Li, Christinger, Mc Kay, De Vos, and Lowman. Selection and analysis or an optimized anti-VEGF antibody: crystal structure of an affinity matured Fab in complex with antigen. Journal of Molecular Biology, 1999. vol. 293, pp. 865-881.*
Wu, Nie, Huse, and Watkins. Humanization of a murine monoclonal antibody by simultaneous optimization of framework and CDR residues. Journal of Molecular Biology, 1999. vol. 294, pp. 151-162.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Allen, T.M. (2002) Nat. Rev. Cancer 2:750-763.
Beers S.A. et al, 2008, Blood 112, (pp. 4170-4177).
Ward, et al., 1989 Nature, 341:544-546.
Brennan et al., Science, 229:81 (1985).
Bird et al. (1988) Science 242:423-426.
Beiboer et al, J. Mol. Biol. 296:833-849 (2000).
Barbas et al, J. Am. Chem. Soc. 116:2161-2162 (1994).
Chan H.T.C. et al., Cancer Research, 63:5480-5489).

*Primary Examiner* — Misook Yu
*Assistant Examiner* — Michael D Allen
(74) *Attorney, Agent, or Firm* — Sterne, Kessler, Goldstein & Fox P.L.L.C.; Timothy J. Shea, Jr.; Erin Heenan

(57) ABSTRACT

The present invention relates to humanized antibodies or fragments thereof that bind to human CD19. More specifically, the present invention relates to a humanized antibody or fragment thereof that binds to human CD19 comprising a heavy chain CDR1 comprising the amino acid sequence of SEQ ID NO: 27, and/or a heavy chain CDR2 comprising the amino acid sequence of SEQ ID NO: 28, and/or a heavy chain CDR3 comprising the amino acid sequence of SEQ ID NO: 29; and/or comprising a light chain CDR1 comprising the amino acid sequence of SEQ ID NO: 30, and/or a light chain CDR2 comprising the amino acid sequence of SEQ ID NO: 31 and/or a light chain CDR3 comprising the amino acid sequence of SEQ ID NO: 32.

15 Claims, 17 Drawing Sheets

(56) References Cited

OTHER PUBLICATIONS

Carter et al., Bio/Technology, 10: 163-167 (1992).
Cox, J. P. L. et al. (1994) "A Directory of Human Germline VH Segments Reveals a Strong Bias in their Usage" Eur. J. Immunol. 24:827-836.
Huston et al. (1988) Proc. Natl. Acad. ScL USA 85:5879-5883.
Holliger et al., 1993, Proc. Natl. Acad. Sci. U.S.A. 90:6444-6448.
Hekman et al, Cancer Immunol. Immunotherapy, 32:364-372 (1991).
Zola, et al., Immunol. Cell. Bio. 69:411-22 (1991).
Imai-Nishiya et al. 2007, BMC Biotechnol. 7:84).
Kaminski et al, N. Engl. J. Med., 329:459-465 (1993).
Klimka et al, British J. of Cancer 83[pound]2):252-260 (2000).
Longmore, et al., (1982) Carbohydr. Res. 365-92.
McCafferty et al. (1990), Nature 348:552-554.
Morimoto et al., J. of Biochemical and Biophysical Methods, 24:107-117 (1992).
Pastan, I. and Kreitman, R.J. (2002) Curr. Opin. Investig. Drugs 3: 1089-1091.
Payne, G. (2003) Cancer Cell 3:207-212.
Pietersz, et al., Cancer Immunol. Immunother., 41:53-60 (1995).
Rader, et al., Proc. Natl. Acad. ScL USA 95:8910-8915 (1998).
Saito, G. et al. (2003) Adv. Drug. Deliv. Rev. 55: 199-215.
Senter, P.D. and Springer, CJ. (2001) Adv. Drug Delivery Rev. 53: 247-264.
Tomlinson et al. 2000, Methods Enzymol. 326:461-479.
Tomlinson, I.M., et al. (1992) The Repertoire of Human Germline VH Sequences Reveals about Fifty Groups of VH Segments with Different Hypervariable Loops J. Mol. Biol. 227:776-798.
Trail, P.A. et al., (2003) Cancer Immunol. Immunother. 52:328-337.
Vermes, et al., 1995, J. Immunol. Methods. 184: 39-51.

\* cited by examiner

Figure 1
Figure 1A
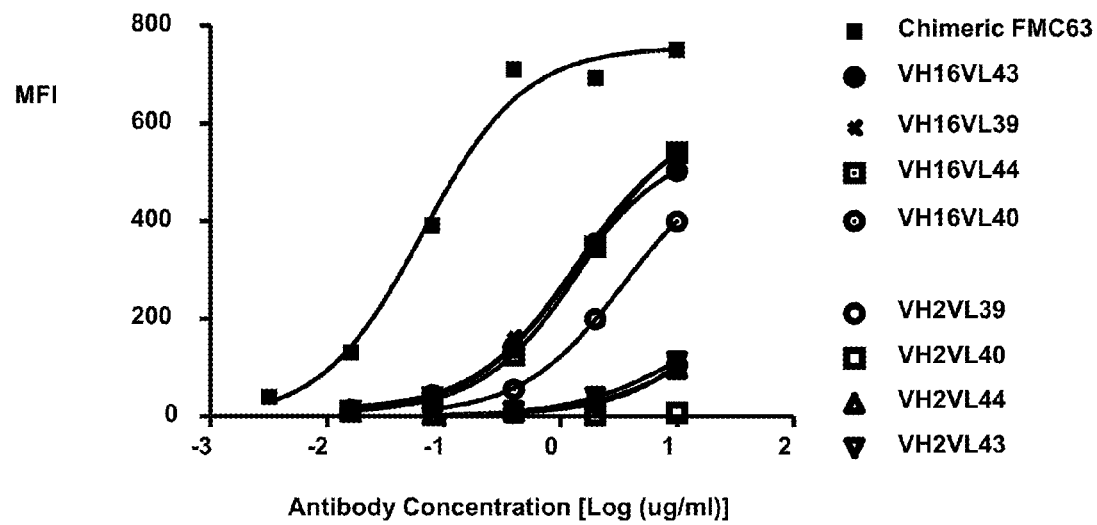
Figure 1B
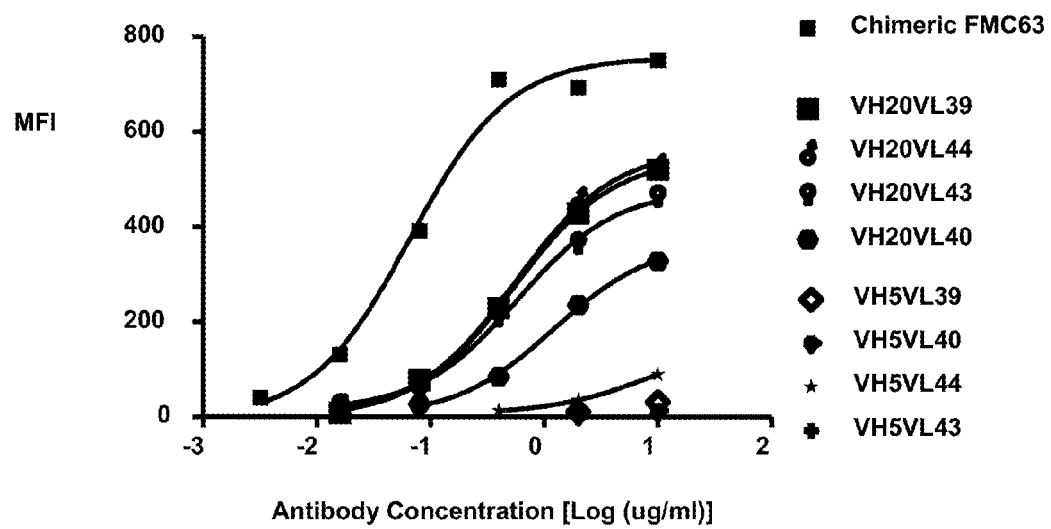

```
                         10        20        30        40        50        60
                ....|....|....|....|....|....|....|....|....|....|....|....|....
Kabat VL#       1234567890123456789012345 67ABCDEF890123456789012345678901234
SEQ ID No: 2 FMC63 VL   DIQMTQTTSSLSASLGDRVTISCRASQ~~~~~~DISKYLNWYQQKPDGTVKLLIYHTSRLHSGVPSRFSG
SEQ ID No: 3 [V1-5*03]  DIQMTQSPSTLSASVGDRVTITCRASQ~~~~~~SISSWLAWYQQKPGKAPKLLIYKASSLESGVPSRFSG
SEQ ID No: 4 [V1-27*01] DIQMTQSPSSLSASVGDRVTITCRASQ~~~~~~GISNYLAWYQQKPGKVPKLLIYAASTLQSGVPSRFSG
SEQ ID No: 5 [V1-39*01] DIQMTQSPSSLSASVGDRVTITCRASQ~~~~~~SISSYLNWYQQKPGKAPKLLIYAASSLQSGVPSRFSG
SEQ ID No: 6 [V1-12*01] DIQMTQSPSSVSASVGDRVTITCRASQ~~~~~~GISSWLAWYQQKPGKAPKLLIYAASSLQSGVPSRFSG
SEQ ID No: 23 (VL39)    DIVMTQSPSTLSASVGDRVTITCRASQ~~~~~~DISKYLNWYQQKPGKAPKLLIYHTSRLHSGVPSRFSG
SEQ ID No: 24 (VL40)    DIVMTQTPSSLSASVGDRVTITCRASQ~~~~~~DISKYLNWYQQKPGKVPNLLIYHTSRLHSGVPSRFSG
SEQ ID No: 25 (VL43)    DIVMTQTPSSLSASVGDRVTITCRASQ~~~~~~DISKYLNWYQQKPGKAPKLLIYHTSRLHSGVPSRFSG
SEQ ID No: 26 (VL44)    DIVMTQSPSSMSASIGDRVTITCRASQ~~~~~~DISKYLNWYQQKPGKAPNLLIYHTSRLHSGVPSRFSG 70        80        90        100
                ....|....|....|....|....|....|..........|....|....
Kabat VL#       567890123456789012345678901 2345ABCDEF67890123456A7
SEQ ID No: 2 FMC63 VL   SGSGTDYSLTISNLEQEDIATYFCQQGNTLP~~~~~~YTFGGGTKLEITR
SEQ ID No: 3 [V1-5*03]  SGSGTEFTLTISSLQPDDFATYYCQQYNSY
SEQ ID No: 4 [V1-27*01] SGSGTDFTLTISSLQPEDVATYYCQKYNSA
SEQ ID No: 5 [V1-39*01] SGSGTDFTLTISSLQPEDFATYYCQQSYST
SEQ ID No: 6 [V1-12*01] SGSGTDFTLTISSLQPEDFATYYCQQANSF
SEQ ID No: 23 (VL39)    SGSGTEFTLTISSLQPDDFATYYCQQGNTLP~~~~~~YTFGQGTKVEIKR
SEQ ID No: 24 (VL40)    SGSGTEFTLTISSLQPEDFATYYCQQGNTLP~~~~~~YTFGGGTKVEIKR
SEQ ID No: 25 (VL43)    SGSGTDFTLTISSLQPEDFATYYCQQGNTLP~~~~~~YTFGPGTKVDIKR
SEQ ID No: 26 (VL44)    SGSGTEFTLTISSLQPEDFATYYCQQGNTLP~~~~~~YTFGQGTKLEIKR
```

Figure 2B

```
                         10        20        30        40        50        60
                ....|....|....|....|....|....|....|.....|....|....|....|....|....|
Kabat VH#       123456789012345678901234567890123 45AB67890123456789012ABC3456789012345
SEQ ID No: 1 FMC63 VH   EVKLQESGPGLVAPSQSLSVTCTVSGVSLPDYGVS~~WIRQPPRKGLEWLGVIW~~~GSETTYYNSALKS
SEQ ID No: 11 [V3-33*01] QVQLVESGGGVVQPGRSLRLSCAASGFTFSSYGMH~~WVRQAPGKGLEWVAVIWY~~DGSNKYYADSVKG
SEQ ID No: 12 [V3-11*01] QVQLVESGGGLVKPGGSLRLSCAASGFTFSDYYMS~~WIRQAPGKGLEWVSYISS~~SGSTIYYADSVKG
SEQ ID No: 13 [V3-30*18] QVQLVESGGGVVQPGRSLRLSCAASGFTFSSYGMH~~WVRQAPGKGLEWVAVISY~~DGSNKYYADSVKG
SEQ ID No: 14 [V3-48*01] EVQLVESGGGLVQPGGSLRLSCAASGFTFSYSMN~~WVRQAPGKGLEWVSYISS~~SSSTIYYADSVKG
SEQ ID No: 19 (VH2)     EVQLVESGGGVVQPGRSLRLSCAASGVSLPDYGVS~~WVRQAPGKGLEWVAVIW~~~GSETTYYNSALKS
SEQ ID No: 20 (VH5)     EVQLVESGGGLVKPGGSLRLSCAASGVSLPDYGVS~~WIRQAPGKGLEWVAVIW~~~GSETTYYNSALKS
SEQ ID No: 21 (VH16)    QVQLVQSGGGVVQPGRSLRLSCAASGVSLPDYGVS~~WVRQAPGKGLEWVAVIW~~~GSETTYYNSALKS
SEQ ID No: 22 (VH20)    QVQLVQSGGGLVQPGGSLRLSCVASGVSLPDYGVS~~WVRQAPGKGLEWVSVIW~~~GSETTYYNSALKS 70        80        90        100       110
                ....|....|....|.....|....|....|....|....|.........|....|....|...
Kabat VH#       6789012345678901 2ABC345678901234567890ABCDEFGHIJK1234567890123
SEQ ID No: 1 FMC63 VH   RLTIIKDNSKSQVFLKMNSLQTDDTAIYYCAKHYYYGGSYAM~~~~~~~DYWGQGTSVTVSS
SEQ ID No: 11 [V3-33*01] RFTISRDNSKNTLYLQMNSLRAEDTAVYYCAR
SEQ ID No: 12 [V3-11*01] RFTISRDNAKNSLYLQMNSLRAEDTAVYYCAR
SEQ ID No: 13 [V3-30*18] RFTISRDNSKNTLYLQMNSLRAEDTAVYYCAR
SEQ ID No: 14 [V3-48*01] RFTISRDNAKNSLYLQMNSLRAEDTAVYYCAR
SEQ ID No: 19 (VH2)     RFTISRDNSKNTLYLQMNSLKTEDTAVYYCTTHYYYGGSYAM~~~~~~~DYWGQGTLVTVSS
SEQ ID No: 20 (VH5)     RFTISRDNAKNSLYLQMDSLRVEDTAVYYCAGHYYYGGSYAM~~~~~~~DYWGQGTLVTVSS
SEQ ID No: 21 (VH16)    RFTISRDNSKNTLYLQMNSLRAEDTAVYYCARHYYYGGSYAM~~~~~~~DYWGQGTLVTVSS
SEQ ID No: 22 (VH20)    RFTISRDNAKNSLYLQMNSLRAEDTAVYYCARHYYYGGSYAM~~~~~~~DYWGQGTLVTVSS
```

Figure 4
Figure 4A
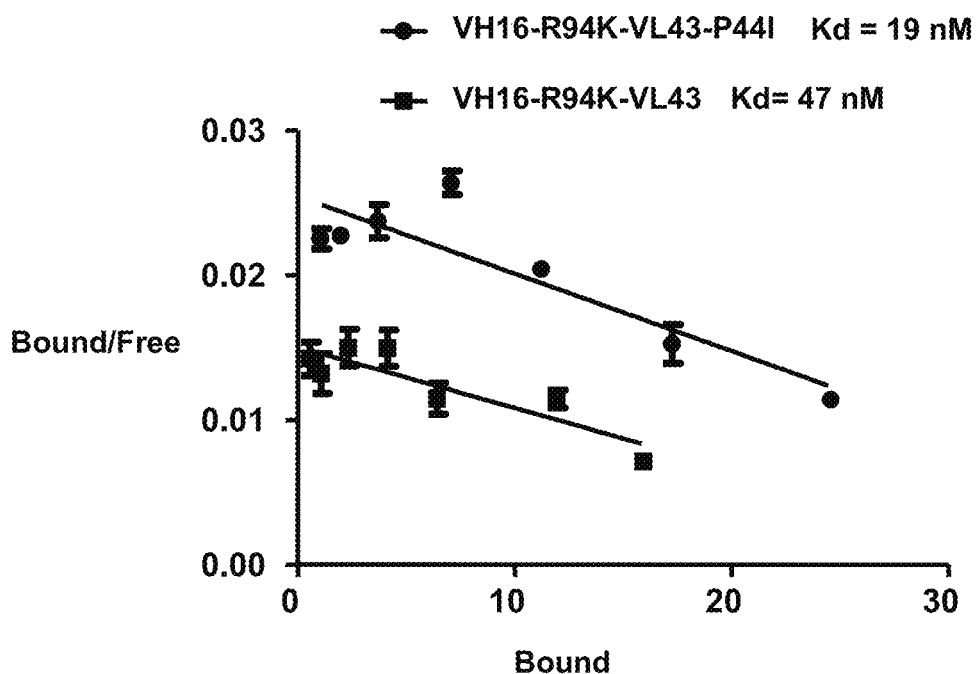
Figure 4B
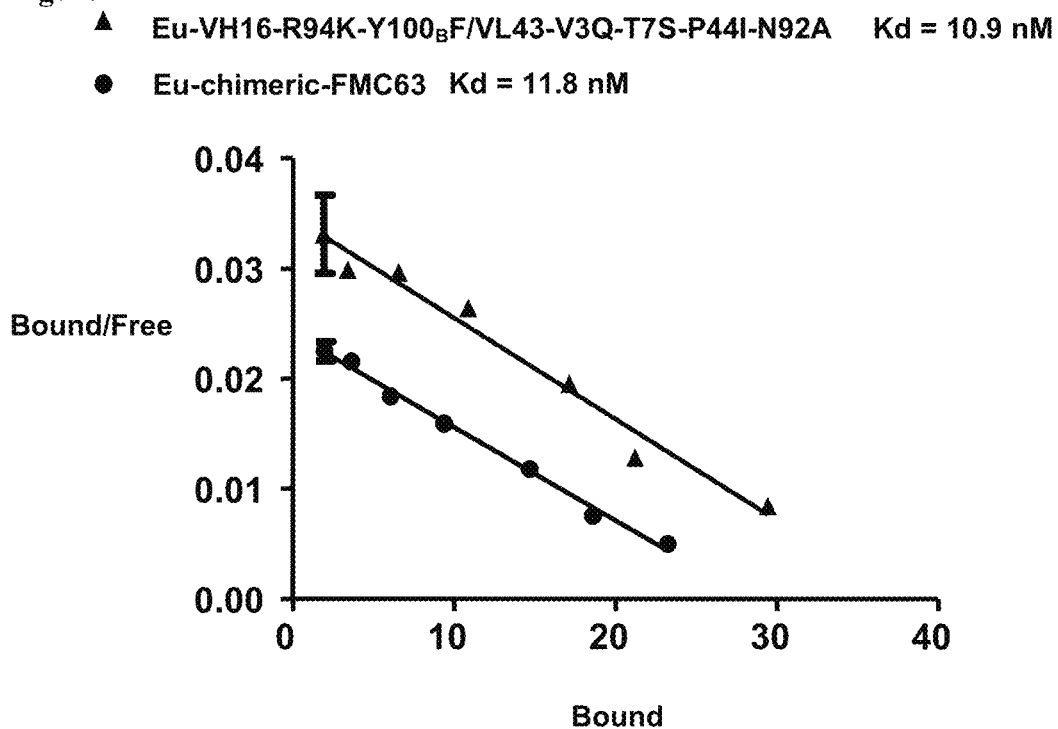

| Keys | |
|---|---|
| Isotype control IgG1 | IgG1 |
| VH16-R94K-Y100$_B$F/VL43-V3Q-T7S-Y32F-P44I-N92A | #1 |
| VH16-R94K/VL43-V3Q-T7S-P44I-N92A | #2 |
| VH16-R94K-Y100$_B$F/VL43-V3Q-T7S-P44I-N92A | #3 |
| VH16-R94K/VL43-P44I | #4 |

| Keys | |
|---|---|
| Isotype control IgG1 | IgG1 |
| Chimeric FMC63 | #A |
| VH16-R94K-Y100$_B$F/VL43-V3Q-T7S-Y32F-P44I-N92A | #1 |
| VH16-R94K/VL43-V3Q-T7S-P44I-N92A | #2 |
| VH16-R94K-Y100$_B$F/VL43-V3Q-T7S-P44I-N92A | #3 |

| Keys | |
|---|---|
| VH16-R94K/VL43-V3Q-T7S-P44I-N92A | #1 |
| VH16-R94K-Y100$_B$F/VL43-V3Q-T7S-P44I-N92A | #2 |
| Chimeric FMC63 | #3 |

| Keys | |
|---|---|
| Chimeric FMC63 | #1 |
| VH16-R94K/VL43-V3Q-T7S-P44I-N92A | #2 |
| VH16-R94K-Y100$_B$F/VL43-V3Q-T7S-Y32F-P44I-N92A | #3 |
| VH16-R94K/VL43-P44I | #4 |

HUMANIZED ANTIBODIES THAT BIND TO CD19 AND THEIR USES

THE FIELD OF THE INVENTION

The present invention relates to humanized antibodies or fragments thereof that bind to human CD19. More specifically, the present invention relates to a humanized antibody or fragment thereof that binds to human CD19 comprising a heavy chain CDR1 comprising the amino acid sequence of SEQ ID NO: 27, and/or a heavy chain CDR2 comprising the amino acid sequence of SEQ ID NO: 28, and/or a heavy chain CDR3 comprising the amino acid sequence of SEQ ID NO: 29; and/or comprising a light chain CDR1 comprising the amino acid sequence of SEQ ID NO: 30, and/or a light chain CDR2 comprising the amino acid sequence of SEQ ID NO: 31 and/or a light chain CDR3 comprising the amino acid sequence of SEQ ID NO: 32.

BACKGROUND OF THE INVENTION

B cell surface markers have been generally suggested as targets for the treatment of B cell disorders or diseases, autoimmune disease, and transplantation rejection. Examples of B cell surface markers include CD10, CD19, CD20, CD21, CD22, CD23, CD24, CD37, CD53, CD72, CD74, CD75, CD77, CD79a, CD79b, CD80, CD81, CD82, CD83, CD84, CD85, and CD86 leukocyte surface markers. Antibodies that specifically bind certain of these markers have been developed, and some have been tested for the treatment of diseases and disorders.

For example, chimeric or radiolabeled monoclonal antibody (mAb)-based therapies directed against the CD20 cell surface molecule specific for mature B cells and their malignant counterparts have been shown to be an effective in vivo treatment for non-Hodgkin's lymphoma (Tedder et al, Immunol. Today 15:450-454 (1994); Press et al, Hematology, 221-240 (2001); Kaminski et al, N. Engl. J. Med., 329:459-465 (1993); Weiner, Semin. Oncol, 26:43-51 (1999); Onrust et al, Drugs, 58:79-88 (1999); McLaughlin et al, Oncology, 12:1763-1769 (1998); Reff et al, Blood, 83:435-445 (1994); Maloney et al, Blood, 90:2188-2195 (1997); Maloney et al, J. Clin. Oncol, 15:3266-3274 (1997); Anderson et al, Biochem. Soc. Transac, 25:705-708 (1997)). Anti-CD20 monoclonal antibody therapy has also been found to ameliorate the manifestations of rheumatoid arthritis, systemic lupus erythematosus, idiopathic thrombocytopenic purpura and hemolytic anemia, as well as other immune-mediated diseases (Silverman et al, Arthritis Rheum., 48:1484-1492 (2002); Edwards et al, Rheumatology, 40:1-7 (2001); De Vita et al, Arthritis Rheumatism, 46:2029-2033 (2002); Leandro et al, Ann. Rheum. Dis., 61:883-888 (2002); Leandro et al, Arthritis Rheum., 46:2673-2677 (2001)). The anti-CD22 monoclonal antibody LL-2 was shown to be effective in treating aggressive and relapsed lymphoma patients undergoing chemotherapeutic treatment (Goldenberg U.S. Pat. Nos. 6,134,982 and 6,306,393). The anti-CD20 (IgG1) antibody, RITUXAN™, has successfully been used in the treatment of certain diseases such as adult immune thrombocytopenic purpura, rheumatoid arthritis, and autoimmune hemolytic anemia (Cured et al, WO 00/67796). Despite the effectiveness of this therapy, most acute lymphoblastic leukemias (ALL) and many other B cell malignancies either do not express CD20, express CD20 at low levels, or have lost CD20 expression following CD20 immunotherapy (Smith et al, Oncogene, 22:7359-7368 (2003)). Moreover, the expression of CD20 is not predictive of response to anti-CD20 therapy as only half of non-Hodgkin's lymphoma patients respond to CD20-directed immunotherapy.

The human CD19 molecule is a structurally distinct cell surface receptor expressed on the surface of human B cells, including, but not limited to, pre-B cells, B cells in early development {i.e., immature B cells), mature B cells through terminal differentiation into plasma cells, and malignant B cells. CD19 is expressed by most pre-B acute lymphoblastic leukemias (ALL), non-Hodgkin's lymphomas, B cell chronic lymphocytic leukemias (CLL), pro-lymphocytic leukemias, hairy cell leukemias, common acute lymphocytic leukemias, and some Null-acute lymphoblastic leukemias (Nadler et al, J. Immunol., 131:244-250 (1983), Loken et al, Blood, 70:1316-1324 (1987), Uckun et al, Blood, 71:13-29 (1988), Anderson et al, 1984. Blood, 63:1424-1433 (1984), Scheuermann, Leuk. Lymphoma, 18:385-397 (1995)). The expression of CD19 on plasma cells further suggests it may be expressed on differentiated B cell tumors such as multiple myeloma, plasmacytomas, Waldenstrom's tumors (Grossbard et al., Br. J. Haematol, 102:509-15 (1998); Treon et al, Semin. Oncol, 30:248-52 (2003)).

The CD19 antigen has also been one of the many proposed targets for immunotherapy. The CLB-CD19 antibody (anti-CD19 murine IgG2a mAb) was shown to inhibit growth of human tumors implanted in athymic mice (Hooijberg et al, Cancer Research, 55:840-846 (1995)). In another study, the monoclonal murine antibody FMC63 (IgG2a) was chimerized using a human IgG1 Fc region (Zola et al, Immunol Cell Biol 69:411-22 (1991)). This antibody did not induce complement-mediated cytotoxicity or ADCC in vitro and administration to SCID mice bearing a human B cell lymphoma (xenotransplantation model) resulted in moderate but unspecified killing of the transplanted tumor cells (Pietersz et al, Cancer Immunol. Immunother., 41:53-60 (1995)).

The results obtained using xenotransplantation mouse models of tumor implantation led to studies using murine anti-CD19 antibodies in human patients. The murine CLB-CD19 antibody was administered to six patients diagnosed with a progressive non-Hodgkin's lymphoma who had failed previous conventional therapy (chemotherapy or radiotherapy). These patients were given total antibody doses ranging from 225 to 1,000 mg (Hekman et al, Cancer Immunol. Immunotherapy, 32:364-372 (1991)). Although circulating tumor cells were temporarily reduced in two patients after antibody infusion, only one patient achieved partial remission after two periods of antibody treatment. No conclusions regarding therapeutic efficacy could be drawn from this small group of refractory patients.

Subsequently, these investigators showed that the anti-tumor effects of unconjugated CD20 mAbs are far superior to those of CD19 mAbs in transplantation models (Hooijberg et al, Cancer Res., 55:840-846 (1995); and Hooijberg et al, Cancer Res., 55:2627-2634 (1995)). Moreover, they did not observe additive or synergistic effects on tumor incidence when using CD19 and CD20 mAbs in combination (Hooijberg et al, Cancer Res., 55:840-846 (1995)). Although the xenotransplantation animal models were recognized to be poor prognostic indicators for efficacy in human subjects, the negative results achieved in these animal studies discouraged interest in therapy with naked anti-CD19 antibodies.

The use of anti-CD19 antibody-based immunotoxins produced equally discouraging results. In early clinical trials, the B4 anti-CD19 antibody (murine IgG1 mAb) was conjugated to the plant toxin ricin and administered to human patients having multiple myeloma who had failed previous conventional therapy (Grossbard et al., British Journal of Haematology, 102:509-515 (1998)), advanced non-Hodgkin's lymphoma (Grossbard et al, Clinical Cancer Research, 5:2392-2398 (1999)), and refractory B cell malignancies (Grossbard et al, Blood, 79:576-585 (1992)). These trials generally demonstrated the safety of administering the B4-ricin conjugate to humans; however, results were mixed and response rates were discouraging in comparison to clinical trials with RITUXAN™ (Grossbard et al, Clinical Cancer Research, 5:2392-2398 (1999)). In addition, a significant portion of the patients developed a human anti-mouse antibody (HAMA) response or a human anti-ricin antibody (HARA) response.

Given the fact that current therapies using naked anti-CD 19 antibodies or anti-CD 19 antibody-based immunotoxins produce equally discouraging results, there exists a need to develop anti-CD 19 antibodies that are more effective to treat CD19 mediated disorders, e.g. anti-CD 19 antibodies that are able to efficiently induce tumor cell death, by triggering apoptosis and blockade of B cell proliferation, and by mediating killing through ADCC.

SUMMARY OF THE INVENTION

The present disclosure relates generally to humanized antibodies or fragments thereof that bind to human CD19, methods for their preparation and use, including methods for treating CD19 mediated disorders. The humanized antibodies or fragments thereof that bind to human CD19 of the present invention exhibit numerous desirable properties including e.g. ADCC activity, induction of apoptosis and inhibition of B cell proliferation.

In one aspect, the present disclosure provides a humanized antibody or fragment thereof that binds to human CD19 comprising a heavy chain CDR1 comprising the amino acid sequence of SEQ ID NO: 27, and/or a heavy chain CDR2 comprising the amino acid sequence of SEQ ID NO: 28, and/or a heavy chain CDR3 comprising the amino acid sequence of SEQ ID NO: 29. In another aspect, the present disclosure provides a humanized antibody or fragment thereof that binds to human CD19 comprising a light chain CDR1 comprising the amino acid sequence of SEQ ID NO: 30, and/or a light chain CDR2 comprising the amino acid sequence of SEQ ID NO: 31 and/or a light chain CDR3 comprising the amino acid sequence of SEQ ID NO: 32.

In another aspect, the present disclosure provides a humanized antibody or fragment thereof that binds to human CD19 comprising a heavy chain CDR1 comprising the amino acid sequence of SEQ ID NO: 27, and/or a heavy chain CDR2 comprising the amino acid sequence of SEQ ID NO: 28, and/or a heavy chain CDR3 comprising the amino acid sequence of SEQ ID NO: 29; and/or comprising a light chain CDR1 comprising the amino acid sequence of SEQ ID NO: 30, and/or a light chain CDR2 comprising the amino acid sequence of SEQ ID NO: 31 and/or a light chain CDR3 comprising the amino acid sequence of SEQ ID NO: 32.

In a further aspect the present invention provides a humanized antibody or fragment thereof that binds to human CD19 comprising a heavy chain variable region sequence selected from the group consisting of SEQ ID NOS: 19, 20, 21, 22, and 42.

In a further aspect the present invention provides a humanized antibody or fragment thereof that binds to human CD19 comprising a heavy chain variable framework region that is the product of or derived from a human gene selected from the group consisting of V3-33*01 (SEQ ID NO: 11), V3-11*01 (SEQ ID NO: 12), V3-30*-18 (SEQ ID NO: 13) and V3-48*01 (SEQ ID NO: 14).

In a further aspect the present invention provides a humanized antibody or fragment thereof that binds to human CD19 comprising a light chain variable region sequence selected from the group consisting of SEQ ID NOS: 23, 24, 25, 26 and 41.

In a further aspect the present invention provides a humanized antibody or fragment thereof that binds to human CD19 comprising a light chain variable framework region that is the product of or derived from a human gene selected from the group consisting of V1-5*03 (SEQ ID NO: 3), V1-27*01 (SEQ ID NO:4), V1-39*-01 (SEQ ID NO: 5) and V1-12*01 (SEQ ID NO: 6).

In a further aspect the present invention provides a humanized antibody or fragment thereof that binds to human CD19 comprising a heavy chain variable region selected from the group consisting of SEQ ID NOS: 33, 34, 35, 36, 37, 43, 44, 45, 46, 47, 54 and 55.

In a further aspect the present invention provides a humanized antibody or fragment thereof that binds to human CD19 comprising a light chain variable region selected from the group consisting of SEQ ID NOS: 25, 38, 39, 40, 48, 49, 50, 51, 52, 53, 56, 57, 58, 59, 60, 61, 62 and 63.

In a further aspect the present invention provides a humanized antibody or fragment thereof that binds to human CD19 comprising
(a) a heavy chain sequence comprising the amino acid sequence of SEQ ID NO: 64; and
(b) a light chain sequence comprising the amino acid sequence of SEQ ID NO: 65.

In a further aspect the present invention provides a humanized antibody or fragment thereof that binds to human CD19 comprising
(a) a heavy chain sequence comprising the amino acid sequence of SEQ ID NO: 66; and
(b) a light chain sequence comprising the amino acid sequence of SEQ ID NO: 67.

In a further aspect the present invention provides a humanized antibody or fragment thereof that binds to human CD19 comprising
(a) a heavy chain sequence comprising the amino acid sequence of SEQ ID NO: 66; and
(b) a light chain sequence comprising the amino acid sequence of SEQ ID NO: 65.

In a further aspect the present invention provides humanized antibodies or fragments thereof that bind to human CD19 comprising human heavy and/or light constant regions, wherein the human heavy constant region comprises an isotypic variant comprising the CH1 from human IgG1, the hinge from human IgG1 and the Fc region from human IgG3.

In a further aspect the present invention provides humanized antibodies or fragments thereof that bind to human CD19 comprising a variant human IgG Fc region which comprises at least one amino acid modification relative to the human IgG Fc region of the parent antibody, whereas the antibody comprising the variant human IgG Fc region exhibits altered effector function compared to the parent antibody.

In a further aspect the present invention provides a humanized antibody or fragment thereof that binds to human CD19, wherein the antibody comprises a variant human IgG Fc region which comprises amino acid substitution S324N replacing serine at amino acid position 324 of the parent antibody with asparagine, whereas the antibody comprising the variant human IgG Fc region exhibits improved complement dependent cytotoxicity (CDC) compared to the parent antibody.

In a further aspect the present invention provides humanized antibodies or fragment thereof that bind to human CD19 which have various desirable properties such as binding to Raji tumor cells, binding to human CD19 with an affinity (Kd) of 50 nM or less, retaining at least 20% of the CD19 binding affinity ($K_d$) of the corresponding chimeric antibody, competing for binding to Raji tumor cells with an affinity (Ki) of 50 nM or less, induction of apoptosis in Raji tumor cells, ADCC activity in Raji tumor cells, inhibition of proliferation of malignant B-cells, inhibition of clonogenicity of Raji tumor cells, causing B-cell depletion in blood, internalization in Raji tumor cells and a FAB fragment thermostability temperature greater than 65° C.

The present disclosure also provides isolated nucleic acids encoding humanized antibodies and fragments thereof that bind to human CD19, vectors and host cells comprising the nucleic acid or the vector. Compositions comprising the humanized antibody or fragment thereof and a pharmaceutically acceptable carrier and immunoconjugates comprising the humanized antibody or fragment thereof linked to a therapeutic agent are also provided.

The present disclosure also provides methods for treating of CD19 mediated disorders, methods of inhibiting growth of tumor cells expressing CD 19 and methods of depleting B cells in a subject in need of such treatment.

The present disclosure also provides kits and articles of manufacturing comprising the humanized antibody or fragment thereof, the composition or the immunoconjugate for the treatment of a CD 19 mediated disorder.

BRIEF DESCRIPTION OF THE FIGURES

FIGS. 1A and 1B show flow cytometry analysis to determine binding activity of FMC63-CDRs grafted to human acceptor antibody frameworks on Raji tumor cells.

FIGS. 2A and 2B show alignment of the light chain (A) or heavy chain (B) variable region of FMC63 with selected germline frameworks from VBASE2 and CDR-grafted donor—amplified frameworks. The Kabat numbering is used and shown below the numbering row.

FIGS. 4A and 4B show Scatchard analysis curves of humanized anti-CD19 antibodies. Analysis was performed on Raji tumor cells using europium-labeled antibodies.

DETAILED DESCRIPTION OF THE INVENTION

Figure 3:
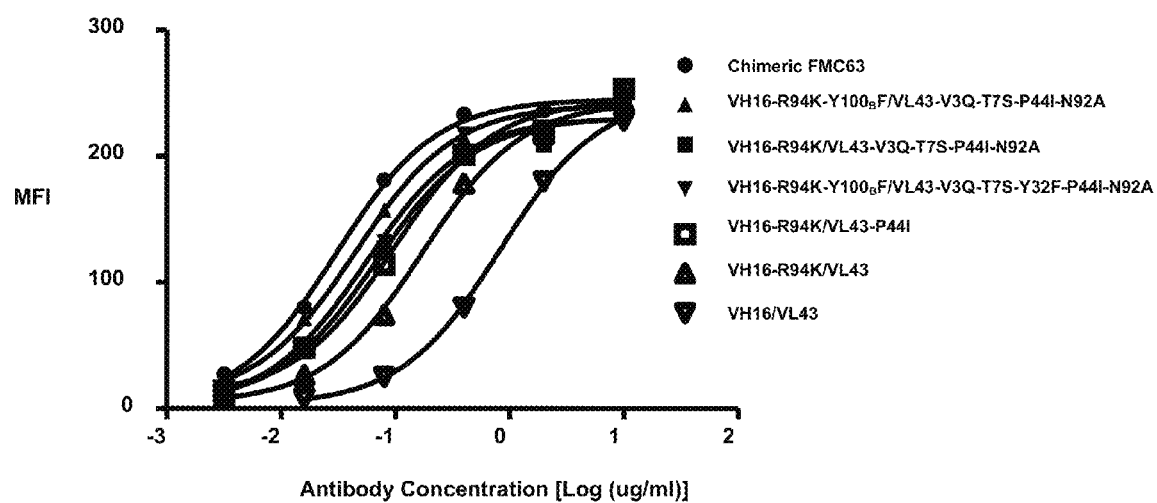
FIG. 3 shows binding activity of humanized antibodies on SU-DHL-6 human B cell lymphoma cells as determined by flow cytometry.

Co-assigned PCT application entitled "Humanized antibodies that bind to CD19 and their uses," filed on Feb. 23, 2010, is incorporated herein by reference in its entirety.

The present disclosure relates to humanized antibodies and fragments thereof that bind human CD 19.

The term "human CD19" as used herein includes variants, isoforms, and species homologs of human CD19. Accordingly, humanized antibodies of this disclosure may, in certain cases, cross-react with CD19 from species other than human. In certain embodiments, the antibodies may be completely specific for one or more human CD19 proteins and may not exhibit species or other types of non-human cross-reactivity. The complete amino acid sequence of an exemplary human CD19 has SwissProt accession number P 15391 (SEQ ID NO: 125). CD19 is also known as B-cell surface antigen B4, B-cell antigen CD19, CD19 antigen, and Leu-12. Human CD19 is designated GeneID: 930 by Entrez Gene, and HGNC: 1633 by HGNC. CD19 can be encoded by the gene designated CD19. The use of "human CD19" herein encompasses all known or as yet undiscovered alleles and polymorphic forms of human CD19. The term "CD19" as used herein refers to "human CD19" if not otherwise specifically indicated.

The term "antibody that bind to human CD19" as used herein includes antibodies, preferably IgG antibodies, that bind to human CD19 e.g. human CD19 as expressed on the surface of Raji tumor cells like Raji tumor cells DSMZ ACC319 with an affinity (Kd) of 500 nM or less, preferably 100 nM or less, more preferably 50 nM or less.

By "B cell" or "B lymphocyte" as used herein is meant a type of lymphocyte developed in bone marrow that circulates in the blood and lymph, and provides humoral immunity. B cells recognize free antigen molecules and differentiate or mature into plasma cells that secrete immunoglobulin (antibodies) that inactivate the antigens. Memory cells are also generated that make the specific Immunoglobulin (antibody) on subsequent encounters with such antigen. B cells are also known as "Beta cells" in the islet of Langerhans.

The term "antibody" as referred to herein includes whole antibodies and any antigen binding fragment or single chains thereof. An "antibody" refers to a glycoprotein comprising at least two heavy (H) chains and two light (L) chains interconnected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR or FW). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the First component (C1q) of the classical complement system.

The term "chimeric antibody" as used herein includes antibodies in which the variable region sequences are derived from one species and the constant region sequences are derived from another species, such as an antibody in which the variable region sequences are derived from a mouse antibody and the constant region sequences are derived from a human antibody.

The term "humanized antibody" as used herein includes antibodies in which CDR sequences derived from the germline of another mammalian species, such as a mouse, have been grafted onto human framework sequences. Additional framework region modifications may be made within the human framework sequences as well as within the CDR sequences derived from the germline of another mammalian species.

The term "human antibody" as used herein includes antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g. mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a humanized antibody comprises heavy or light chain variable framework regions that are "the product of" or "derived from" a particular human germline sequence (human gene) if the variable framework regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A humanized antibody which comprises a heavy or light chain variable framework region that is "the product of" or "derived from" a human germline immunoglobulin sequence can be identified as such by comparing the amino acid sequence of the heavy or light chain variable framework region of the humanized antibody to the amino acid sequences of the heavy or light chain variable framework region of human germline immunoglobulins. A humanized antibody that comprises a heavy or light chain variable framework region that is "the product of" a particular human germline immunoglobulin sequence has a heavy or light chain variable framework region which is 100% identical in amino acid sequence to the heavy or light chain variable framework region of the particular human germline immunoglobulin sequence. A humanized antibody that comprises a heavy or light chain variable framework region that is "derived from" a particular human germline immunoglobulin sequence may contain amino acid differences as compared to the heavy or light chain variable framework region of the particular germline sequence, due to, for example, naturally-occurring somatic mutations or intentional introduction of site-directed mutation. However, a selected humanized antibody typically is at least 90% identical in amino acid sequence of the heavy or light chain variable framework region to an amino acid sequence encoded by the heavy or light chain variable framework region of a human germline immunoglobulin gene and contains amino acid residues that identify the humanized antibody as being derived from human when compared to the germline immunoglobulin amino acid sequences of other species (e.g., murine germline sequences). In certain cases, a humanized antibody may be preferably at least 95%, more preferably at least 96%, most preferably at least 97%, in particular at least 98%, most particular at least 99%, identical in amino acid sequence of the heavy or light chain variable framework region to the amino acid sequence of the heavy or light chain variable framework region encoded by the germline immunoglobulin gene. Typically, the heavy or light chain variable framework region of a humanized antibody derived from a particular human germline sequence will display no more than 10 amino acid, preferably no more than 5, or even more preferably no more than 4, 3, 2, or 1 differences from the amino acid sequence of the heavy or light chain variable framework region encoded by the human germline immunoglobulin gene.

The term "Fab" or "Fab region" as used herein includes the polypeptides that comprise the VH, CH1, VL, and CL immunoglobulin domains. Fab may refer to this region in isolation, or this region in the context of a full length antibody or antibody fragment.

The term "Fc" or "Fc region", as used herein includes the polypeptide comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM, Fc may include the J chain. For IgG, Fc comprises immunoglobulin domains Cgamma2 and Cgamma3 (C[gamma]2 and C[gamma]3) and the hinge between Cgamma1 (C[gamma]1) and Cgamma2 (C[gamma]2). Although the boundaries of the Fc region may vary, the human IgG heavy chain Fc region is usually defined to comprise residues C226 or P230 to its carboxyl-terminus, wherein the numbering is according to the EU index as in Kabat. For human IgG1 the Fc region is herein defined to comprise residue P232 to its carboxyl-terminus, wherein the numbering is according to the EU index as in Kabat. Fc may refer to this region in isolation, or this region in the context of an Fc polypeptide, for example an antibody.

The term "hinge" or "hinge region" or "antibody hinge region" herein includes the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgGI) to 231 (A231 in IgGI), wherein the numbering is according to the EU index as in Kabat.

The term "parent antibody" or "parent immunoglobulin" as used herein includes an unmodified antibody that is subsequently modified to generate a variant. Said parent antibody may be a naturally occurring antibody, or a variant or engineered version of a naturally occurring antibody. Parent antibody may refer to the antibody itself, compositions that comprise the parent antibody, or the amino acid sequence that encodes it. By "parent anti-CD 19 antibody" as used herein is meant an antibody or immunoglobulin that binds human CD 19 and is modified to generate a variant.

The term "parental antibody" or "parental immunoglobulin" as used herein includes a murine or chimeric antibody that is subsequently modified to generate a humanized antibody.

The term "variant antibody" or "antibody variant" as used herein includes an antibody sequence that differs from that of a parent antibody sequence by virtue of at least one amino acid modification compared to the parent. The variant antibody sequence herein will preferably possess at least about 80%, most preferably at least about 90%, more preferably at least about 95% amino acid sequence identity with a parent antibody sequence. Antibody variant may refer to the antibody itself, compositions comprising the antibody variant, or the amino acid sequence that encodes it.

The term "amino acid modification" herein includes an amino acid substitution, insertion, and/or deletion in a polypeptide sequence. By "amino acid substitution" or "substitution" herein is meant the replacement of an amino acid at a particular position in a parent polypeptide sequence with another amino acid. For example, the substitution R94K refers to a variant polypeptide, in this case a heavy chain variable framework region variant, in which the arginine at position 94 is replaced with a lysine. For the preceding example, 94K indicates the substitution of position 94 with a lysine. For the purposes herein, multiple substitutions are typically separated by a slash. For example, R94K/L78V refers to a double variant comprising the substitutions R94K and L78V. By "amino acid insertion" or "insertion" as used herein is meant the addition of an amino acid at a particular position in a parent polypeptide sequence. For example, insert—94 designates an insertion at position 94. By "amino acid deletion" or "deletion" as used herein is meant the removal of an amino acid at a particular position in a parent polypeptide sequence. For example, R94—designates the deletion of arginine at position 94.

As used herein, the term "conservative modifications" or "conservative sequence modifications" is intended to refer to amino acid modifications that do not significantly affect or alter the binding characteristics of the antibody containing the amino acid sequence. Such conservative modifications include amino acid substitutions, insertions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions or within the framework regions of an antibody of the invention can be replaced with other amino acid residues from the same side chain family and the altered antibody (variant antibody) can be tested for retained function.

For all immunoglobulin heavy chain constant region positions discussed in the present invention, numbering is according to the EU index as in Kabat (Kabat et al., 1991, Sequences of Proteins of Immunological Interest, 5th Ed., United States Public Health Service, National Institutes of Health, Bethesda, incorporated entirely by reference). The "EU index as in Kabat" refers to the residue numbering of the human IgG1 EU antibody, as described in Edelman et al., 1969, Biochemistry 63:78-85.

The term "full length antibody" as used herein includes the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, CH1 (C[gamma]1), CH2 (C[gamma]2), and CH3 (C[gamma]3). In some mammals, for example in camels and llamas, IgG antibodies may consist of only two heavy chains, each heavy chain comprising a variable domain attached to the Fc region.

Antibody fragments include, but are not limited to, (i) the Fab fragment consisting of VL, VH, CL and CH1 domains, including Fab' and Fab'-SH, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) F(ab')2 fragments, a bivalent fragment comprising two linked Fab fragments (vi) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (vii) bispecific single chain Fv dimers (PCT/US92/09965), (viii) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448) and (ix) scFv genetically fused to the same or a different antibody (Coloma & Morrison, 1997, Nature Biotechnology 15, 159-163).

Antibodies are grouped into classes, also referred to as isotypes, as determined genetically by the constant region. Human constant light chains are classified as kappa (CK) and lambda (C[lambda]) light chains. Heavy chains are classified as mu, delta, gamma, alpha, or epsilon, and define the antibody's isotype as IgM, IgD, IgG, IgA, and IgE, respectively. The IgG class is the most commonly used for therapeutic purposes. In humans this class comprises subclasses IgG1, IgG2, IgG3, and IgG4. In mice this class comprises subclasses IgG1, IgG2a, IgG2b, IgG3. IgM has subclasses, including, but not limited to, IgM1 and IgM2. IgA has several subclasses, including but not limited to IgA1 and IgA2. Thus, "isotype" as used herein is meant any of the classes or subclasses of immunoglobulins defined by the chemical and antigenic characteristics of their constant regions. The known human immunoglobulin isotypes are IgG1, IgG2, IgG3, IgG4, IgA1, IgA2, IgM1, IgM2, IgD, and IgE.

The term "ADCC" or "antibody dependent cell-mediated cytotoxicity" as used herein includes the cell-mediated reaction wherein nonspecific cytotoxic cells that express Fc[gamma]Rs recognize bound antibody on a target cell and subsequently cause lysis of the target cell. In various aspects, the enhanced ADCC effector function can mean enhanced potency or enhanced efficacy. By "potency" as used in the experimental context is meant the concentration of antibody when a particular therapeutic effect is observed EC50 (half maximal effective concentration). By "efficacy" as used in the experimental context is meant the maximal possible effector function at saturating levels of antibody.

The term "ADCP" or antibody dependent cell-mediated phagocytosis as used herein includes the cell-mediated reaction wherein nonspecific cytotoxic cells that express Fc[gamma]Rs recognize bound antibody on a target cell and subsequently cause phagocytosis of the target cell.

The term "CDC" or "complement dependent cytotoxicity" as used herein includes the reaction wherein one or more complement protein components recognize bound antibody on a target cell and subsequently cause lysis of the target cell.

The term "effector function" as used herein includes a biochemical event that results from the interaction of an antibody Fc region with an Fc receptor or ligand. Effector functions include Fc[gamma]R-mediated effector functions such as ADCC and ADCP, and complement-mediated effector functions such as CDC.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc. Preferably the subject is human.

The term "isotypic variant" as used herein includes an amino acid modification that converts at least one amino acid of one isotype, preferably at least one amino acid of the heavy chain constant region of one isotype, to the corresponding amino acid in a different, aligned isotype. The amino acid modification may comprise conversion of a whole constant region immunoglobulin domain or, preferably, of an Fc region of one isotype in a different isotype, e.g. the conversion of the Fc region of the human IgG1 heavy constant region to an Fc region from human IgG3 resulting in an isotypic variant comprising the CH1 from human IgG1, the hinge from human IgG1 and the Fc region from human IgG3.

The term "isotypic modification" as used herein includes an amino acid modification that converts one amino acid of one isotype to the corresponding amino acid in a different, aligned isotype. For example, because IgG1 has a tyrosine and IgG2 a phenylalanine at Kabat position 296, a F296Y substitution in IgG2 is considered an isotypic modification.

The term "mature core carbohydrate structure" as used herein includes a processed core carbohydrate structure attached to an Fc region which generally consists of the carbohydrate structure GlcNAc (Fucose)-GlcNAc-Man-(Man-GlcNAc)$_2$ typical of biantennary oligosaccharides represented schematically below:

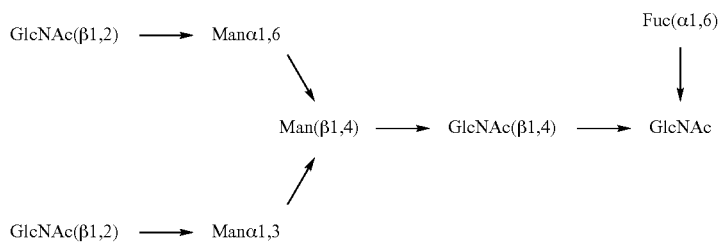

This term specifically includes G-1 forms of the core mature carbohydrate structure lacking a β1,2 GlcNAc residue. Preferably, however, the core carbohydrate structure includes both β1,2 GlcNAc residues. The mature core carbohydrate structure herein generally is not hypermannosylated. The mature core carbohydrate structure is attached to the Fc region of the glycoprotein, generally via N-linkage to Asn297 of a CH2 domain of the Fc region.

Anti-CD19 Antibodies

In a first aspect the present invention provides a humanized antibody or fragment thereof that binds to human CD19 comprising a heavy chain CDR1 comprising the amino acid sequence of SEQ ID NO: 27, and/or a heavy chain CDR2 comprising the amino acid sequence of SEQ ID NO: 28, and/or a heavy chain CDR3 comprising the amino acid sequence of SEQ ID NO: 29. In another aspect, the present disclosure provides a humanized antibody or fragment thereof that binds to human CD19 comprising a light chain CDR1 comprising the amino acid sequence of SEQ ID NO: 30, and/or a light chain CDR2 comprising the amino acid sequence of SEQ ID NO: 31 and/or a light chain CDR3 comprising the amino acid sequence of SEQ ID NO: 32.

In another aspect, the present disclosure provides a humanized antibody or fragment thereof that binds to human CD19 comprising a heavy chain CDR1 comprising the amino acid sequence of SEQ ID NO: 27, and/or a heavy chain CDR2 comprising the amino acid sequence of SEQ ID NO: 28, and/or a heavy chain CDR3 comprising the amino acid sequence of SEQ ID NO: 29; and/or comprising a light chain CDR1 comprising the amino acid sequence of SEQ ID NO: 30, and/or a light chain CDR2 comprising the amino acid sequence of SEQ ID NO: 31 and/or a light chain CDR3 comprising the amino acid sequence of SEQ ID NO: 32.

Preferably the humanized antibody or fragment thereof that binds to human CD19 comprises a heavy chain CDR1 comprising the amino acid sequence of SEQ ID NO: 27, a heavy chain CDR2 comprising the amino acid sequence of SEQ ID NO: 28, and a heavy chain CDR3 comprising the amino acid sequence of SEQ ID NO: 29 and/or a light chain CDR1 comprising the amino acid sequence of SEQ ID NO: 30, a light chain CDR2 comprising the amino acid sequence of SEQ ID NO: 31 and a light chain CDR3 comprising the amino acid sequence of SEQ ID NO: 32. More preferably the humanized antibody or fragment thereof that binds to human CD19 comprises a heavy chain CDR1 comprising the amino acid sequence of SEQ ID NO: 27, a heavy chain CDR2 comprising the amino acid sequence of SEQ ID NO: 28, and a heavy chain CDR3 comprising the amino acid sequence of SEQ ID NO: 29; and a light chain CDR1 comprising the amino acid sequence of SEQ ID NO: 30, a light chain CDR2 comprising the amino acid sequence of SEQ ID NO: 31 and a light chain CDR3 comprising the amino acid sequence of SEQ ID NO: 32.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al, British J. of Cancer 83 [pound]2):252-260 (2000) (describing the production of a humanized anti-CD30 antibody using only the heavy chain variable domain CDR3 of murine anti-CD30 antibody Ki-4); Beiboer et al, J. Mol. Biol. 296:833-849 (2000) (describing recombinant epithelial glycoprotein-2 (EGP-2) antibodies using only the heavy chain CDR3 sequence of the parental murine MOC-31 anti-EGP-2 antibody); Rader et al, Proc. Natl. Acad. ScL U.S.A. 95:8910-8915 (1998) (describing a panel of humanized anti-integrin [alpha]v[beta]3 antibodies using a heavy and light chain variable CDR3 domain of a murine anti-integrin [alpha]v[beta]3 antibody LM609 wherein each member antibody comprises a distinct sequence outside the CDR3 domain and capable of binding the same epitope as the parental murine antibody with affinities as high or higher than the parental murine antibody); Barbas et al, J. Am. Chem. Soc. 116:2161-2162 (1994) (disclosing that the CDR3 domain provides the most significant contribution to antigen binding).

Accordingly, the present invention provides humanized antibodies and fragments thereof that bind to human CD19 comprising one or more heavy and/or light chain CDR3 domains from an antibody of a non-human animal e.g from a murine antibody like FMC63, in particular comprising heavy chain CDR3 comprising the amino acid sequence of SEQ ID NO: 29 and/or light chain CDR3 comprising the amino acid sequence of SEQ ID NO: 32, wherein the antibody is capable of binding to CD 19. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human e.g. murine antibody.

In a further aspect the present invention provides a humanized antibody or fragment thereof that binds to human CD19 comprising a heavy chain variable region sequence selected from the group consisting of SEQ ID NOS: 19, 20, 21, 22 and 42, preferably a heavy chain variable region sequence selected from the group consisting of SEQ ID NOS: 21, 22 and 42, more preferably a heavy chain variable region sequence comprising SEQ ID NO: 21.

In another aspect the present invention provides a humanized antibody or fragment thereof that binds to human CD19 comprising a light chain variable region sequence selected from the group consisting of SEQ ID NOS: 23, 24, 25, 26 and 41, preferably a light chain variable region sequence selected from the group consisting of SEQ ID NOS: 25 and 41, more preferably a light chain variable region sequence comprising SEQ ID NO: 41.

In some embodiments the humanized antibody or fragment thereof that binds to human CD19 comprises a heavy chain variable region sequence selected from the group consisting of SEQ ID NOS: 19, 20, 21, 22, and 42 and a light chain variable region sequence selected from the group consisting of SEQ ID NOS: 23, 24, 25, 26 and 41, preferably a heavy chain variable region sequence selected from the group consisting of SEQ ID NOS: 21, 22 and 42 and a light chain variable region sequence selected from the group consisting of SEQ ID NOS: 23, 24, 25, 26 and 41, more preferably a heavy chain variable region sequence selected from the group consisting of SEQ ID NOS: 21, 22 and 42 and a light chain variable region sequence selected from the group consisting of SEQ ID NOs: 25 and 41, most preferably a heavy chain variable region sequence comprising SEQ ID NO: 21 and a light chain variable region sequence comprising SEQ ID NO: 41.

Given that each of these heavy and light chain variable region sequences can bind to human CD19, the heavy and light chain variable region sequences can be "mixed and matched" to create anti-CD19 binding molecules of the invention. CD 19 binding of such "mixed and matched" antibodies can be tested using the binding assays described e.g. in the Examples.

In another aspect the present invention provides variants of a humanized antibody or fragment thereof that binds to human CD19. Thus the present invention provides humanized antibodies or fragments thereof that have an amino acid sequence of the heavy and/or light chain variable framework region which is at least 80% identical (having at least 80% amino acid sequence identity) to the amino acid sequence of the heavy and/or light chain variable framework region of the parent humanized antibody of either the heavy or the light chain e.g. of either the heavy and light variable region sequences as in SEQ ID NO: 21 or SEQ ID NO: 41, respectively. Preferably the amino acid sequence identity of the heavy and/or light chain variable framework region is at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to an amino acid sequence is defined herein as the percentage of amino acid residues in the candidate sequence that are identical with the humanized antibody or fragment thereof that binds to human CD19, after aligning the sequences and introducing gaps, if necessary, to achieve the maximum percent sequence identity. Thus sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM250 (a standard scoring matrix; see Dayhoff et al., in Atlas of Protein Sequence and Structure, vol 5, supp. 3 (1978)) can be used in conjunction with the computer program. For example, the percent identity can be calculated as: the total number of identical matches multiplied by 100 and then divided by the sum of the length of the longer sequence within the matched span and the number of gaps introduced into the longer sequences in order to align the two sequences.

In some embodiments the present disclosure thus provides a humanized antibody or fragment thereof that binds to human CD19, wherein the humanized antibody or fragment thereof comprises a heavy chain variable framework region sequence which is at least 80% identical to the framework region sequence of SEQ ID NOS: 19, 20, 21, 22 or 42 and/or a light chain variable framework region sequence which is at least 80% identical to the framework region sequence of SEQ ID NOS: 23, 24, 25, 26 and 41.

In some embodiments the present disclosure provides a humanized antibody or fragment thereof that binds to human CD19, wherein the humanized antibody or fragment thereof comprises a heavy chain variable framework region sequence which is at least 80% identical to the framework region sequence of SEQ ID NO: 21, 22 or 42 and/or a light chain variable framework region sequence which is at least 80% identical to the framework region sequence of SEQ ID NO: 25 or 41. In some embodiments the present disclosure provides a humanized antibody or fragment thereof that binds to human CD19, wherein the humanized antibody or fragment thereof comprises a heavy chain variable framework region sequence which is at least 80% identical to the framework region sequence of SEQ ID NO: 21 and/or a light chain variable framework region sequence which is at least 80% identical to the framework region sequence of SEQ ID NO: 41.

In another aspect the present invention provides a humanized antibody or fragment thereof that binds to human CD19 comprising the heavy and or light chain CDRs as described supra and further comprising a heavy chain variable framework region that is the product of or derived from a human gene selected from the group consisting of V3-33*01 (SEQ ID NO: 11), V3-11*01 (SEQ ID NO: 12), V3-30*-18 (SEQ ID NO: 13) and V3-48*01 (SEQ ID NO: 14), preferably a heavy chain variable framework region that is the product of or derived from human gene V3-30*-18 (SEQ ID NO: 13) or V3-48*01 (SEQ ID NO: 14), more preferably a heavy chain variable framework region that is the product of or derived from human gene V3-30*-18 (SEQ ID NO: 13). The heavy chain variable framework region may comprise one or more (e.g., one, two, three and/or four) heavy chain framework region sequences (e.g., framework 1 (FW1), framework 2 (FW2), framework 3 (FW3) and/or framework 4 (FW4)) present in the product of or derived from those human genes. Preferably the heavy chain variable region framework comprises FW1, FW2 and/or FW3, more preferably FW1, FW2 and FW3 present in the product of or derived from a human gene selected from the group consisting of V3-33*01 (SEQ ID NO: 11), V3-11*01 (SEQ ID NO: 12), V3-30*-18 (SEQ ID NO: 13) and V3-48*01 (SEQ ID NO: 14). Heavy chain framework region sequences as used herein include FW1 (position 1 to position 25), FW2 (position 36 to position 49), FW3 (position 66 to position 94) and FW4 (position 103 to position 113), wherein the amino acid position is indicated utilizing the numbering system set forth in Kabat.

In another aspect the present invention provides a humanized antibody or fragment thereof that binds to human CD19 comprising a light chain variable framework region that is the product of or derived from a human gene selected from the group consisting of V1-5*03 (SEQ ID NO: 3), V1-27*01 (SEQ ID NO:4), V1-39*-01 (SEQ ID NO: 5) and V1-12*01 (SEQ ID NO: 6), preferably a light chain variable framework region that is the product of or derived from human gene V1-39*-01 (SEQ ID NO: 5). The light chain variable region framework region may comprise one or more (e.g., one, two, three and/or four) light chain framework region sequences (e.g., framework 1 (FW1), framework 2 (FW2), framework 3 (FW3) and/or framework 4 (FW4)) present in the product of or derived from those human genes. Preferably the light chain variable region framework comprises FW1, FW2 and/or FW3, more preferably FW1, FW2 and FW3 present in the product of or derived from a human gene selected from the group consisting of V1-5*03 (SEQ ID NO: 3), V1-27*01 (SEQ ID NO:4), V1-39*-01 (SEQ ID NO: 5) and V1-12*01 (SEQ ID NO: 6). Light chain framework region sequences as used herein include FW1 (position 1 to position 23), FW2 (position 35 to position 49), FW3 (position 57 to position 88) and FW4 (position 98 to position 108), wherein the amino acid position is indicated utilizing the numbering system set forth in Kabat.

In some embodiments the humanized antibody or fragment thereof that binds to human CD19 comprises a heavy chain variable framework region that is the product of or derived from a human gene selected from the group consisting of V3-33*01 (SEQ ID NO: 11), V3-11*01 (SEQ ID NO: 12), V3-30*-18 (SEQ ID NO: 13) and V3-48*01 (SEQ ID NO: 14) and a light chain variable framework region that is the product of or derived from a human gene selected from the group consisting of V1-5*03 (SEQ ID NO: 3), V1-27*01 (SEQ ID NO:4), V1-39*-01 (SEQ ID NO: 5) and V1-12*01 (SEQ ID NO: 6), preferably a heavy chain variable framework region that is the product of or derived from human gene V3-30*-18 (SEQ ID NO: 13) or V3-48*01 (SEQ ID NO: 14), and a light chain variable framework region that is the product of or derived from human gene V1-39*-01 (SEQ ID NO: 5), more preferably a heavy chain variable framework region that is the product of or derived from human gene V3-30*-18 (SEQ ID NO: 13) and a light chain variable framework region that is the product of or derived from human gene V1-39*-01 (SEQ ID NO: 5).

As well combinations of heavy chain variable region framework regions which are present in the product of or derived from different human genes and/or of light chain variable region framework regions which are present in the product of or derived from different human genes are encompassed by the present invention, e.g. FW1 and FW2 present in the product of or derived from V3-30*-18 (SEQ ID NO: 13) combined with FW3 present in the product of or derived from V3-48*01 (SEQ ID NO: 14) and/or FW1 and FW2 present in the product of or derived from V1-39*-01 (SEQ ID NO: 5) combined with FW3 present in the product of or derived from V1-12*01 (SEQ ID NO: 6).

Germline DNA sequences for human heavy and light chain variable region genes can be found in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germline VH Segments Reveals a Strong Bias in their Usage" Eur. J. Immunol. 24:827-836. As another example, the germline DNA sequences for human heavy and light chain variable region genes can be found in the Genbank database.

In another aspect, the present disclosure also provides a humanized antibody or fragment thereof that binds to human CD19, wherein at least one of the heavy chain CDRs and/or at least one of the light chain CDRs comprises at least one amino acid modification. Site-directed mutagenesis or PCR-mediated mutagenesis can be performed to introduce the modification(s) and the effect on antibody binding, or other functional property of interest, can be evaluated in in vitro or in vivo assays as described herein and provided in the Examples. Preferably conservative modifications are introduced. The modification(s) may be amino acid substitutions, additions or deletions, but are preferably substitutions. Typically, no more than five, preferably no more than four, more preferably no more than three, even more preferably no more than two, most preferably no more than one amino acid modifications are performed within a CDR region.

Thus the present disclosure also provides a humanized antibody or fragment thereof that binds to human CD19, comprising an amino acid modification comprising amino acid substitution Y32F within heavy chain CDR1, and/or comprising an amino acid modification comprising amino acid substitution Y58F or Y59F within heavy chain CDR2 and/or comprising an amino acid modification comprising one or more amino acid substitutions selected from the group consisting of Y96F, Y97F, Y98F and $Y100_BF$ within heavy chain CDR3. Preferred amino acid modifications of the humanized antibody or fragment thereof is amino acid substitution Y32F within heavy chain CDR1 and amino acid substitutions selected from the group consisting of Y96F, Y97F, Y98F and $Y100_BF$ within heavy chain CDR3. More preferred amino acid modifications of the humanized antibody or fragment thereof are amino acid substitution Y32F within heavy chain CDR1 and/or amino acid substitution $Y100_BF$ within heavy chain CDR3.

The present disclosure also provides a humanized antibody or fragment thereof, comprising an amino acid modification comprising amino acid substitution Y32F within light chain CDR1 and/or comprising an amino acid modification comprising an amino acid substitution selected from the group consisting of N92A, T93A and T93V within light chain CDR3. Preferred amino acid modifications of the humanized antibody or fragment thereof are amino acid substitution Y32F within light chain CDR1 and/or amino acid substitution N92A within light chain CDR3.

In some embodiments the present disclosure provides a humanized antibody or fragment thereof that binds to human CD19, comprising an amino acid modification comprising amino acid substitution Y32F within heavy chain CDR1, and/or comprising an amino acid modification comprising amino acid substitution Y58F or Y59F within heavy chain CDR2 and/or comprising an amino acid modification comprising one or more amino acid substitutions selected from the group consisting of Y96F, Y97F, Y98F and $Y100_BF$ within heavy chain CDR3 and comprising an amino acid modification comprising amino acid substitution Y32F within light chain CDR1 and/or comprising an amino acid modification comprising an amino acid substitution selected from the group consisting of N92A, T93A and T93V within light chain CDR3.

In certain embodiments, framework sequences can be used to engineer variable regions to produce variant antibodies. Variant antibodies of the invention include those in which modifications have been made to framework residues within VH and/or VK, e.g. to improve the properties of the antibody. Typically such framework modifications are made to decrease the immunogenicity of the antibody. For example, one approach is to "backmutate" one or more framework residues to the corresponding murine sequence or to "backmutate" one or more framework residues to a corresponding germline sequence.

Thus in a further aspect the present disclosure provides a humanized antibody or fragment thereof that binds to human CD19, wherein at least one of the framework regions of the heavy chain variable region of the humanized antibody or fragment thereof comprises at least one amino acid modification from the corresponding framework region of the heavy chain variable region of the corresponding murine antibody. Preferably the amino acid modification is an amino acid substitution. Typically, no more than five, preferably no more than four, more preferably no more than three, even more preferably no more than two, most preferably no more than one amino acid modifications are performed within a framework region.

In some embodiments the present disclosure provides a humanized antibody or fragment thereof that binds to human CD19, wherein the amino acid modification of the framework regions of the heavy chain variable region comprise an amino acid substitution at amino acid position selected from the group consisting of 37, 42, 48, 49, 67, 71, 78 and 94. Preferred amino acid substitution of the framework regions of the heavy chain variable region are at amino acid positions selected from the group consisting of 42, 67, 71, 78 and 94. More preferred amino acid substitutions of the framework regions of the heavy chain variable region are selected from the group consisting of G42R, F67L, R71K, L78V and R94K, with the proviso that if the amino acid modification is R94K the heavy chain variable region sequence is not SEQ ID NO: 19 or SEQ ID NO: 20, whereas R94K is the most preferred amino acid substitution of the framework regions of the heavy chain variable region.

The present disclosure also provides a humanized antibody or fragment thereof that binds to human CD19, wherein at least one of the framework regions of the light chain variable region of the humanized antibody or fragment thereof comprises at least one amino acid modification from the corresponding framework region of the light chain variable region of the corresponding murine antibody. Preferably the amino acid modification is an amino acid substitution. Typically, no more than five, preferably no more than four, more preferably no more than three, even more preferably no more than two, most preferably no more than one amino acid modifications are performed within a framework region. In some embodiments the present disclosure provides a humanized antibody or fragment thereof, wherein the amino acid modification of the framework regions of the light chain variable region sequence comprises an amino acid substitution at amino acid position selected from the group consisting of 44, 71 and 87. More preferred amino acid substitutions of the framework regions of the light chain variable region sequence are selected from the group consisting of P44V, P44I, P44L, F71Y, F71H, F71S, F71T and Y87F. Most preferred amino acid substitutions of the framework regions of the light chain variable region sequence are selected from the group consisting of P44V, P44I, F71Y, and Y87F, whereas P44I is particular preferred.

In some embodiments the humanized antibody or fragment thereof of the present invention may comprise amino acid modifications of the framework regions of the heavy chain variable region sequence as set out supra and amino acid modifications of the framework regions of the light chain variable region sequence as set out supra.

The present disclosure also provides a humanized antibody or fragment thereof that binds to human CD19 that comprises a heavy chain variable region selected from the group consisting of SEQ ID NOS: 33, 34, 35, 36, 37, 43, 44, 45, 46, 47, 54 and 55, preferably selected from the group consisting of SEQ ID NOS: 37, 43 and 47, more preferably selected from the group consisting of SEQ ID NOS: 37 and 47.

The present disclosure also provides a humanized antibody or fragment thereof that binds to human CD19 that comprises a light chain variable region selected from the group consisting of SEQ ID NOS: 25, 38, 39, 40, 48, 49, 50, 51, 52, 53, 56, 57, 58, 59, 60, 61, 62 and 63, preferably selected from the group consisting of SEQ ID NOS: 25, 59 and 60, more preferably selected from the group consisting of SEQ ID NOS: 59 and 60.

In some embodiments the humanized antibody or fragment thereof that binds to human CD19 comprises a heavy chain variable region selected from the group consisting of SEQ ID NOS: 33, 34, 35, 36, 37, 43, 44, 45, 46, 47, 54 and 55, and a light chain variable region selected from the group consisting of SEQ ID NOS: 25, 38, 39, 40, 48, 49, 50, 51, 52, 53, 56, 57, 58, 59, 60, 61, 62 and 63.

In some embodiments the humanized antibody or fragment thereof that binds to human CD19 comprises a heavy chain variable region selected from the group consisting of SEQ ID NOS: 37, 43 and 47, and a light chain variable region selected from the group consisting of SEQ ID NOS: 25, 59 and 60. In more preferred embodiments the humanized antibody or fragment thereof that binds to human CD19 comprises a heavy chain variable region selected from the group consisting of SEQ ID NOS: 37 and 47, and a light chain variable region selected from the group consisting of SEQ ID NOS: 59 and 60. Most preferred is a humanized antibody or fragment thereof that binds to human CD19 comprising a heavy chain variable region comprising the amino acid sequence of SEQ ID NO: 37, and a light chain variable region comprising the amino acid sequence of SEQ ID NO: 59, a humanized antibody or fragment thereof that binds to human CD19 comprising a heavy chain variable region comprising the amino acid sequence of SEQ ID NO: 47, and a light chain variable region comprising the amino acid sequence of SEQ ID NO: 60, a humanized antibody or fragment thereof that binds to human CD19 comprising a heavy chain variable region comprising the amino acid sequence of SEQ ID NO: 47, and a light chain variable region comprising the amino acid sequence of SEQ ID NO: 59, a humanized antibody or fragment thereof that binds to human CD19 comprising a heavy chain variable region comprising the amino acid sequence of SEQ ID NO: 37, and a light chain variable region comprising the amino acid sequence of SEQ ID NO: 25, a humanized antibody or fragment thereof that binds to human CD19 comprising a heavy chain variable region comprising the amino acid sequence of SEQ ID NO: 37, and a light chain variable region comprising the amino acid sequence of SEQ ID NO: 49, a humanized antibody or fragment thereof that binds to human CD19 comprising a heavy chain variable region comprising the amino acid sequence of SEQ ID NO: 47, and a light chain variable region comprising the amino acid sequence of SEQ ID NO: 49 or a humanized antibody or fragment thereof that binds to human CD19 comprising a heavy chain variable region comprising the amino acid sequence of SEQ ID NO: 43, and a light chain variable region comprising the amino acid sequence of SEQ ID NO: 59, in particular a humanized antibody or fragment thereof that binds to human CD19 comprising a heavy chain variable region comprising the amino acid sequence of SEQ ID NO: 37, and a light chain variable region comprising the amino acid sequence of SEQ ID NO: 59, a humanized antibody or fragment thereof that binds to human CD19 comprising a heavy chain variable region comprising the amino acid sequence of SEQ ID NO: 47, and a light chain variable region comprising the amino acid sequence of SEQ ID NO: 60, a humanized antibody or fragment thereof that binds to human CD19 comprising a heavy chain variable region comprising the amino acid sequence of SEQ ID NO: 47, and a light chain variable region comprising the amino acid sequence of SEQ ID NO: 59.

Given that each of these heavy and light chain variable region sequences can bind to human CD19, the heavy and light chain variable region sequences can be "mixed and matched" to create anti-CD19 binding molecules of the invention. CD19 binding of such "mixed and matched" antibodies can be tested using the binding assays described e.g. in the Examples.

In some embodiments the humanized antibody or fragment thereof that binds to human CD19 comprises a heavy chain sequence comprising the amino acid sequence of SEQ ID NO: 64, and a light chain sequence comprising the amino acid sequence of SEQ ID NO: 65.

In some embodiments the humanized antibody or fragment thereof that binds to human CD19 comprises a heavy chain sequence comprising the amino acid sequence of SEQ ID NO: 66, and a light chain sequence comprising the amino acid sequence of SEQ ID NO: 67.

In some embodiments the humanized antibody or fragment thereof that binds to human CD19 comprises a heavy chain sequence comprising the amino acid sequence of SEQ ID NO: 66, and a light chain sequence comprising the amino acid sequence of SEQ ID NO: 65.

The present disclosure also provides a humanized antibody or fragment thereof that binds to human CD19 which further comprises a human heavy and/or light constant domain. Human heavy constant regions may be selected from the group of human immunoglobulins consisting of IgG1, IgG2, IgG3, IgG4, IgA1, IgA2, IgM1, IgM2, IgD, and IgE, whereas the human heavy constant region IgG, in particular IgG1 is preferred. Human light constant region may be selected from the group of human immunoglobulins consisting of kappa or lambda constant regions, whereas human kappa constant region is preferred. In some preferred embodiments the humanized antibody or fragment thereof comprises a human IgG1 heavy constant domain and a human light kappa constant domain. The present disclosure also provides a humanized antibody or fragment thereof that binds to human CD19 comprising human heavy and/or light constant regions, wherein the human heavy constant region comprises an isotypic variant comprising the CH1 from human IgG1, the hinge from human IgG1 and the Fc region from human IgG3. Preferably the humanized antibody comprising the isotypic variant is a full length antibody. A particular preferred humanized antibody or fragment thereof that binds to human CD19 comprising an isotypic variant comprising the CH1 from human IgG1, the hinge from human IgG1 and the Fc region from human IgG3 comprises a heavy chain sequence comprising the amino acid sequence of SEQ ID NO: 124 and a light chain sequence comprising the amino acid sequence of SEQ ID NO: 65. It has been found that the isotypic variant exhibits improved complement dependent cytotoxicity (CDC) as compared to a humanized antibody or fragment thereof that binds to human CD19 which comprises a human heavy constant region from human IgG1 (which is usually a native human IgG1), i.e. as compared to a humanized antibody or fragment thereof that binds to human CD19 that only differs from the isotypic variant with regard to the modified heavy constant region.

The present disclosure also provides a fragment of a humanized antibody that binds to human CD19 selected from the group consisting of Fab, Fab', Fab'-SH, Fd, Fv, dAb, F(ab')2, scFv, bispecific single chain Fv dimers, diabodies, triabodies and scFv genetically fused to the same or a different antibody. Preferred fragments are scFv, bispecific single chain Fv dimers and diabodies. The present disclosure also provides a full length humanized antibody that binds to human CD19.

In addition or alternative to modifications made within the framework regions or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation. Each of these embodiments is described in further detail below. Modifications within the Fc region as outlined below are according to the numbering of residues in the Fc region of the EU index of Kabat. In one embodiment, the hinge region of CH1 is modified such that the number of cysteine residues in the hinge region is altered, e.g., increased or decreased. This approach is described further in U.S. Pat. No. 5,677,425 by Bodmer et al.

The number of cysteine residues in the hinge region of CH1 is altered to, for example, facilitate assembly of the light and heavy chains or to increase or decrease the stability of the antibody. In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al. In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. In a further embodiment Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al. In another example, one or more amino acid residues within amino acid positions 231 to 238 in the N-terminal region of the CH2 domain are altered to thereby alter the ability of the antibody to fix complement. This approach is described further in PCT Publication WO 94/29351 by Bodmer et al. In yet another example, the Fc region is modified to increase the ability of the antibody to mediate antibody dependent cellular cytotoxicity (ADCC) and/or to increase the affinity of the antibody for an Fc[gamma] receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta.

Thus in a preferred embodiment the present disclosure provides a humanized antibody or fragment thereof that binds to human CD19, which comprises a variant human IgG Fc region which comprises at least one amino acid modification relative to the human IgG Fc region of the parent antibody, whereas the antibody comprising the variant human IgG Fc region exhibits altered effector function compared to the parent antibody. Preferably the antibody comprises a variant human IgG1 Fc region. More preferred is a full length antibody comprising a variant human IgG1 Fc region. The parent antibody is a humanized antibody or fragment thereof that binds to human CD19 and is identical to the humanized antibody that binds to human CD19 which comprises a variant human IgG Fc region, except for the amino acid modification in the human IgG Fc region and is usually an antibody with a native human IgG Fc region. The amino acid modification is preferably not isotopic.

The effector function altered is usually complement dependent cytotoxicity (CDC) and/or C1q binding and/or antibody dependent cell mediated cytotoxicity (ADCC) and/or binding affinity of the antibody for an Fc[gamma] receptor, preferably complement dependent cytotoxicity (CDC) and/or antibody dependent cell mediated cytotoxicity (ADCC). CDC, C1q binding, ADCC, and binding affinity of the antibody for an Fc[gamma] receptor are measured by standard in vitro assays, which are known in the art and commercially available. Usually ADCC is measured by the lactate dehydrogenase (LDH)-releasing assay as described e.g. in Example 4 of the present application and CDC is measure by the cell-based assay described e.g. in Example 10 of the present application.

In one embodiment the amino acid modification which alters the effector function compared to the parent antibody comprises an amino acid substitution at amino acid position selected from the group consisting of 269, 274, 276, 298, 324 and 334, preferably selected from the group consisting of 269, 298 and 324, more preferably 298 and/or 324, wherein the amino acid position of each group member is indicated utilizing the numbering system set forth in Kabat.

In a further embodiment the amino acid modification which alters the effector function compared to the parent antibody comprises an amino acid substitution selected from the group consisting of E269D, K274Q, N276K, S298A, S324N, and K334R, preferably selected from the group consisting of E269D, S298A and S324N, more preferably S298A and/or S324N, wherein the amino acid position of each group member is indicated utilizing the numbering system set forth in Kabat.

In a further embodiment the amino acid modification which alters the effector function compared to the parent antibody comprises a combination of amino acid substitutions at amino acid position selected from the group consisting of 269/274, 269/276, 269/298, 269/324, 269/334, 274/276, 274/298, 274/324, 274/334, 276/298, 276/324, 276/334, 298/324, 298/334, 324/334, 269/274/276, 269/274/298, 269/274/324, 269/274/334, 269/276/298, 269/276/324, 269/276/334, 269/298/324, 269/298/334, 274/276/298, 274/276/324, 274/276/334, 274/298/324, 274/298/334, 276/298/324, and 276/298/334, preferably selected from the group consisting of 274/276, 269/298, 298/324, 274/276/334, and 269/298/324, more preferably selected from the group consisting of 298/324 and 269/298/324, wherein the amino acid position of each group member is indicated utilizing the numbering system set forth in Kabat.

In a further embodiment the amino acid modification which alters the effector function compared to the parent antibody comprises a combination of amino acid substitutions selected from the group consisting of E269D/K274Q, E269D/N276K, E269D/S298A, E269D/S324N, E269D/K334R, K274Q/N276K, K274Q/S298A, K274Q/S324N, K274Q/K334R, N276K/S298A, N276K/S324N, N276K/K334R, S298A/S324N, S298A/K334R, S324N/K334R, E269D/K274Q/N276K, E269D/K274Q/S298A, E269D/K274Q/S324N, E269D/K274Q/K334R, E269D/N276K/S298A, E269D/N276K/S324N, E269D/N276K/K334R, E269D/S298A/S324N, E269D/S298A/K334R, K274Q/N276K/S298A, K274Q/N276K/S324N, K274Q/N276K/K334R, K274Q/S298A/S324N, K274Q/S298A/K334R, N276K/S298A/S324N, and N276K/S298A/K334R, preferably selected from the group consisting of K274Q/N276K, E269D/S298A, S298A/S324N, K274Q/N276K/K334R, and E269D/S298A/S324N, more preferably selected from the group consisting of S298A/S324N and E269D/S298A/S324N, wherein the amino acid position of each group member is indicated utilizing the numbering system set forth in Kabat.

Preferably the humanized anti-CD-19 antibody of the present disclosure comprising the variant human IgG Fc region exhibits improved CDC in an in vitro assay as described above compared to the parent antibody. Exhibition of improved CDC as used herein includes a) exhibition of enhanced CDC compared to the parent antibody, i.e. the parent antibody already exhibits CDC which is enhanced by the amino acid modification of the human IgG Fc region and b) de novo exhibition of CDC compared to the parent antibody, i.e. the parent antibody does not exhibit CDC, thus CDC has been introduced de novo by the amino acid modification of the human IgG Fc region.

In a further embodiment, variants of the human IgG Fc region of the humanized anti-CD-19 antibody of the present invention which exhibit improved CDC in an in vitro assay compared to the parent antibody comprise an amino acid substitution or a combination of amino acid substitutions at amino acid positions selected from the group consisting of 324, 334, 274/276, 298/324, 274/276/334, and 269/298/324, preferably selected from the group consisting of 324, 334, 298/324, 274/276/334, and 269/298/324, more preferably selected from the group consisting of 324, 298/324, and 269/298/324, wherein the amino acid position of each group member is indicated utilizing the numbering system set forth in Kabat. In a further embodiment, variants of the human IgG Fc region of the humanized anti-CD-19 antibody of the present invention which exhibit improved CDC in an in vitro assay compared to the parent antibody comprise an amino acid substitution or a combination of amino acid substitutions at amino acid positions selected from the group consisting of S324N, K334R, K274Q/N276K, S298A/S324N, K274Q/N276K/K334R, and E269D/S298A/S324N, preferably selected from the group consisting of S324N, K334R, S298A/S324N, K274Q/N276K/K334R, and E269D/S298A/S324N, more preferably selected from the group consisting of S324N, S298A/S324N, and E269D/S298A/S324N, wherein the amino acid position of each group member is indicated utilizing the numbering system set forth in Kabat.

In a further embodiment, variants of the human IgG Fc region of the humanized anti-CD-19 antibody of the present invention which exhibit improved ADCC in an in vitro assay compared to the parent antibody comprise an amino acid substitution or a combination of amino acid substitutions at amino acid position selected from the group consisting of 269, 298, 269/298, 269/324, 298/324, and 269/298/324, preferably selected from the group consisting of 298, 269/298, 269/298/324, wherein the amino acid position of each group member is indicated utilizing the numbering system set forth in Kabat.

In a further embodiment, variants of the human IgG Fc region of the humanized anti-CD-19 antibody of the present invention which exhibit improved ADCC in an in vitro assay compared to the parent antibody comprise an amino acid substitution or a combination of amino acid substitutions at amino acid position selected from the group consisting of E269D, S298A, E269D/S298A, E269D/S324N, S298A/S324N, and E269D/S298A/S324N, preferably selected from the group consisting of S298A, E269D/S298A, and E269D/S298A/S324N, wherein the amino acid position of each group member is indicated utilizing the numbering system set forth in Kabat.

Thus particular preferred humanized antibodies or fragments thereof that binds to human CD19 and exhibit altered effector function compared to the parent humanized antibody provided by the present disclosure are humanized antibodies or fragments thereof comprising a heavy chain sequence comprising the amino acid sequence of SEQ ID NO: 114 (VH16 R94K/S298A) and a light chain sequence comprising the amino acid sequence of SEQ ID NO: 65 (VL43 V3Q/T7S/P44I/N92A); a heavy chain sequence comprising the amino acid sequence of SEQ ID NO: 115 (VH16 R94K/E269D/S298A) and a light chain sequence comprising the amino acid sequence of SEQ ID NO: 65 (VL43 V3Q/T7S/P44I/N92A); a heavy chain sequence comprising the amino acid sequence of SEQ ID NO: 116 (VH16 R94K/S298A/S324N) and a light chain sequence comprising the amino acid sequence of SEQ ID NO: 65 (VL43 V3Q/T7S/P44I/N92A); a heavy chain sequence comprising the amino acid sequence of SEQ ID NO: 117 (VH16 R94K/E269D/S298A/S324N) and a light chain sequence comprising the amino acid sequence of SEQ ID NO: 65 (VL43 V3Q/T7S/P44I/N92A); a heavy chain sequence comprising the amino acid sequence of SEQ ID NO: 118 (VH16 R94K/S324N) and a light chain sequence comprising the amino acid sequence of SEQ ID NO: 65 (VL43 V3Q/T7S/P44I/N92A); a heavy chain sequence comprising the amino acid sequence of SEQ ID NO: 119 (VH16 R94K/K274Q) and a light chain sequence comprising the amino acid sequence of SEQ ID NO: 65 (VL43 V3Q/T7S/P44I/N92A); a heavy chain sequence comprising the amino acid sequence of SEQ ID NO: 120 (VH16 R94K/N276K) and a light chain sequence comprising the amino acid sequence of SEQ ID NO: 65 (VL43 V3Q/T7S/P44I/N92A); a heavy chain sequence comprising the amino acid sequence of SEQ ID NO: 121 (VH16 R94K/K334R) and a light chain sequence comprising the amino acid sequence of SEQ ID NO: 65 (VL43 V3Q/T7S/P44I/N92A) a heavy chain sequence comprising the amino acid sequence of SEQ ID NO: 122 (VH16 R94K/K274Q/N276K) and a light chain sequence comprising the amino acid sequence of SEQ ID NO: 65 (VL43 V3Q/T7S/P44I/N92A); or a heavy chain sequence comprising the amino acid sequence of SEQ ID NO: 123 (VH16 R94K/K274Q/N276K/K334R) and a light chain sequence comprising the amino acid sequence of SEQ ID NO: 65 (VL43 V3Q/T7S/P44I/N92A).

The present disclosure further provides a humanized antibody or fragment thereof that binds to human CD19, wherein the antibody comprises a variant human IgG Fc region which comprises amino acid substitution S324N replacing serine at amino acid position 324 of the parent antibody with asparagine, whereas the antibody comprising the variant human IgG Fc region exhibits improved complement dependent cytotoxicity (CDC) compared to the parent antibody. Preferably the antibody comprises a variant human IgG1 Fc region. More preferred is a full length antibody comprising a variant human IgG1 Fc region. It has surprisingly found that among 16 different amino acid substitutions at amino acid position 324 the substitution S324N significantly improves CDC compared to the parent antibody whereas the other substitutions do not improve CDC compared to the parent antibody as described in Example 10. Without being bound by theory, this unexpected selective effect on CDC of the S324N substitution seems to be due to an enhanced binding to human complement component C1q.

The present disclosure also provides a humanized antibody or fragment thereof that binds to human CD19 which comprises a human IgG Fc region, wherein the mature core carbohydrate structure attached to the human IgG Fc region lacks fucose. Preferably the antibody comprises a human IgG1 Fc region, wherein the mature core carbohydrate structure attached to the human IgG1 Fc region lacks fucose. More preferred is a full length antibody comprising a human IgG1 Fc region, wherein the mature core carbohydrate structure attached to the human IgG1 Fc region lacks fucose. It is known from WO 2003/035835 that lack of fucose in the mature core carbohydrate structure attached to the human IgG Fc region may enhance ADCC. Thus in a further embodiment the humanized antibody or fragment thereof of the present disclosure comprises a human IgG Fc region, wherein the mature core carbohydrate structure attached to the human IgG Fc region lacks fucose, whereas the antibody lacking fucose exhibits enhanced ADCC compared to the parent humanized antibody or fragment thereof not lacking fucose. A preferred antibody or fragment thereof that binds to human CD19 comprising a human IgG Fc region, wherein the mature core carbohydrate structure attached to the human IgG Fc region lacks fucose, whereas the antibody lacking fucose exhibits enhanced ADCC compared to the parent humanized antibody or fragment thereof not lacking fucose is the antibody comprising a heavy chain sequence comprising the amino acid sequence of SEQ ID NO: 64, and a light chain sequence comprising the amino acid sequence of SEQ ID NO: 65. Methods to generate antibodies which lack fucose are, for example, (a) use of an engineered or mutant host cell that is deficient in fucose metabolism such that it has a reduced ability (or is unable to) fucosylate proteins expressed therein; (b) culturing cells under conditions which prevent or reduce fucosylation; (c) post-translational removal of fucose (e.g. with a fucosidase enzyme); (d) post-translational addition of the desired carbohydrate, e.g. after recombinant expression of a non-glycosylated glycoprotein; or (e) purification of the glycoprotein so as to select for product which is not fucosylated. Preferably used are methods described in Example 14, e.g. methods described in Longmore et al. (1982), Carbohydr. Res. 365-92, or in Imai-Nishiya et al. (2007), BMC Biotechnol. 7, 84.

Anti-CD19 Antibodies Properties

Standard assays to evaluate the binding ability of the antibodies toward e.g. human CD19 are known in the art, including for example, ELISAs, Western blots, R1As, and flow cytometry analysis. Suitable assays are described in detail in the Examples. The binding kinetics (e.g., binding affinity like $K_d$) of the antibodies also can be assessed by standard assays known in the art, such as by Scatchard or Biacore<(R)>system analysis and can be performed and calculated e.g. as described in Example 3. The relative binding affinity $K_i$ can be assessed by standard competition assay known in the art and can be performed and calculated e.g. as described in Example 3. To assess binding, Raji tumor cells (human Burkitt lymphoma, DSMZ ACC319), NALM-6 (human B cell precursor leukemia, DSMZ AC128) or SU-DHL-6 (human B cell lymphoma, DSMZ ACC572) can be used, preferably Raji tumor cells such as human Burkitt lymphoma, DSMZ ACC319 or SU-DHL-6 (human B cell lymphoma, DSMZ ACC572), more preferably Raji tumor cells such as human Burkitt lymphoma, DSMZ ACC319 are used. Those cells can be obtained from publicly available sources, such as the Deutsche Sammlung von Mikroorganismen and Zellkulturen GmbH, Braunschweig, Germany, and can be used in standard assays, such as flow cytometric analysis. The corresponding chimeric antibody which can be used in the assays of the present invention is usually a chimeric version of murine antibody FMC63 which consists of the FMC63 murine heavy variable domain fused to human IgG1 heavy constant domains and the murine light variable domain fused to kappa constant domain. The corresponding chimeric antibody which is preferably used in the assays of the present invention is a chimeric version of antibody FMC63 comprising a heavy chain sequence comprising the amino acid sequence of SEQ ID NO: 68 and a light chain sequence comprising the amino acid sequence of SEQ ID NO: 69. The parental non-humanized antibody or corresponding parental non-humanized antibody which can be used in the assays of the present invention is usually a murine antibody, in particular murine antibody FMC63.

The present disclosure also provides a humanized antibody or fragment thereof that binds to Raji tumor cells with Mid-Point Fluorescence (MPF) of at least 10% relative to the binding of the corresponding chimeric antibody. Raji tumor cells do express CD19 on their surface to which the humanized antibody or fragment thereof can bind. Values for Mid-Point Fluorescence can be obtained from measurements of Mean Fluorescent Intensity (MFI) of cell staining using flow cytometry versus antibody concentration. Preferably the humanized antibody or fragment thereof binds to Raji tumor cells with MPF of at least 30%, more preferably of at least 50%, most preferably of at least 70%, in particular of at least 80%, more particular of at least 90%, most particular of at least 95% relative to the binding of the corresponding chimeric antibody. Raji tumor cells as described supra can be used for assessing binding to CD19.

The present disclosure also provides a humanized antibody or fragment thereof that binds to human CD19 with an affinity ($K_d$) of 50 nM or less, in particular 40 nM or less, more particular 30 nM or less, even more particular 20 nM or less, most particular 15 nM or less. Raji tumor cells as described supra can be used for assessing binding to human CD19.

The present disclosure also provides a humanized antibody or fragment thereof that retains at least 20% of the CD19 binding affinity ($K_d$) of the corresponding chimeric antibody. Preferably the humanized antibody or fragment thereof retains at least 40%, more preferably at least 60%, most preferably at least 80%, in particular at least 90%, more particular at least 95% of the CD19 binding affinity ($K_d$) of the corresponding chimeric antibody. Raji tumor cells or SU-DHL-6 cells as described supra can be used for assessing binding to human CD19.

The present disclosure also provides a humanized antibody or fragment that binds to human CD19 and competes for binding to Raji tumor cells with an affinity ($K_i$) of 50 nM or less, preferably 20 nM or less, more preferably 10 nM or less, most preferably 5 nM or less, in particular 4 nM or less, more particular 3 nM or less, most particular at least about 1.5 nM to about 5.0 nM (e.g. 1,9; 1.6 or 2.9 to about 2.6 or 4.9 nM). Binding competition is usually measured against the corresponding chimeric antibody, whereas Raji tumor cells as described supra can be used for assessing $K_i$.

The present disclosure also provides a humanized antibody or fragment thereof that binds to human CD19 and induces apoptosis in Raji tumor cells. Induction of apoptosis in Raji tumor cells can be measured by annexin-V and propidium iodine staining (Vermes et al., 1995, J. Immunol. Methods. 184: 39-51). The induction of apoptosis is a very surprising property displayed by the humanized antibodies of the present invention in view of the fact that the corresponding chimeric antibody has no effect on apoptosis. Raji tumor cells as described supra can be used for assessing apoptosis. Thus the present disclosure also provides a humanized antibody or fragment thereof wherein apoptosis is induced in at least 10%, preferably in at least 15%, more preferably in at least 20%, most preferably in at least 25% of Raji tumor cells.

The present disclosure also provides a humanized antibody or fragment thereof that binds to human CD19 and induces ADCC activity in Raji tumor cells. ADCC related specific lysis of target cells such as Raji tumor cells as described supra can be assessed using e.g. a lactate dehydrogenase release assay (CytoTox 96 Non radioactive assay, Promega, Madison, USA). Surprisingly the humanized antibody or fragment thereof that binds to human CD19 induces ADCC activity in Raji tumor cells equivalent or even greater to induction of ADCC activity of the corresponding chimeric antibody. Preferably the humanized antibody or binding fragment thereof that binds CD19 has at least 80%, more preferably at least 100%, most preferably at least 120% of the ADCC activity of the corresponding chimeric antibody.

The present disclosure also provides a humanized antibody or fragment thereof that binds to human CD19 and that inhibits proliferation of malignant B-cells. Preferably, the humanized antibody or fragment thereof retains at least 60%, more preferably at least 80%, most preferably at least 90%, in particular 95%, more particular 100% of the inhibition of the proliferation of malignant B-cells of the corresponding chimeric antibody. To measure inhibition of cell proliferation by antibodies, Raji tumor cells or SU-DHL-6 cells as described supra can be used for assessing proliferation of malignant B-cells.

The present disclosure also provides a humanized antibody or fragment thereof that binds to human CD19 and that inhibits clonogenicity of Raji tumor cells. The inhibition of clonogenicity is measured by counting the number of clones after treatment with the antibody and can be carried out according to e.g. Nahimana et al., 2009, Blood. 0: blood-2008-08-173369v1" (Blood, 2009, Vol. 113, No. 14, pp. 3276-3286). Raji tumor cells as described supra can be used for assessing clonogenicity. The number of clones counted after treatment with the humanized antibodies of the invention is at least 30%, preferably at least 40%, more preferably at least 50%, most preferably at least 60% less than the number of clones counted after treatment with the corresponding chimeric antibody. The inhibition of clonogenicity of Raji tumor cells confirms the strong inhibitory function of the humanized antibodies of the invention on B cell proliferation.

The present disclosure also provides a humanized antibody or fragment thereof that binds to human CD19 and that causes B-cell depletion in blood. Preferably, the B cell depletion caused is at least identical, preferably at least 1.5 times, more preferably at least 2 times greater than the B cell depletion caused by the corresponding chimeric antibody. B cell depletion can be assessed by determining the % positive B cells in whole blood after incubation with antibody as described in the Examples.

The present disclosure also provides a humanized antibody or fragment thereof that binds to human CD19 and that internalizes in Raji tumor cells. The humanized antibody or fragment of the present invention internalizes at a degree comparable to the degree of internalization of the corresponding chimeric antibody. Preferably, the internalization degree of the humanized antibody of the invention used at 0.01 µg/ml is between 50% and 150%, more preferably between 60% and 140%, most preferably between 70% and 130% of the internalization degree of the corresponding chimeric antibody. Antibody internalization can be assessed on Raji tumor cells as described supra using e.g. a secondary anti-human antibody conjugated to the toxin saporin (Hum-Zap, Advanced Targeting Systems, San Diego, Calif., USA).

The present disclosure also provides a humanized antibody or fragment thereof that binds to human CD19 which has a FAB fragment thermostability temperature greater than 65° C., preferably greater than 70° C., more preferably greater than 75° C., most preferably greater than 80° C. For analysis of FAB fragment thermostability differential scanning calorimetry measurements are used, whereas a mid-point melting temperature of the FAB fragment in context of a full-length IgG is identified. These kind of calorimetric measurements are known to the skilled person and can be carried out according to e.g. Garber and Demarest (2007), BBRC 355:751-7. Surprisingly, it has been found that the humanized antibody of the present invention has a FAB fragment thermostability temperature equivalent to the corresponding chimeric antibody. Thus the present disclosure also provides a humanized antibody or fragment thereof that binds to human CD19 which has a FAB fragment thermostability temperature equivalent to the FAB fragment thermostability temperature of the corresponding chimeric antibody.

Nucleic Acids, Vectors and Host Cells

The present disclosure also provides isolated nucleic acids encoding the humanized antibodies and fragments thereof that bind to human CD19, vectors and host cells comprising the nucleic acid or the vector. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art, see e.g. F. Ausubel, et al, ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques e.g. cDNAs encoding the light and heavy chains of the antibody or encoding VH and VL segments can be obtained by standard PCR amplification or cDNA cloning techniques. For antibodies obtained from an immunoglobulin gene library (e.g., using phage display techniques), one or more nucleic acids encoding the antibody can be recovered from the library. The methods of introducing exogenous nucleic acid into host cells are well known in the art, and will vary with the host cell used. Techniques include but are not limited to dextran-mediated transfection, calcium phosphate precipitation, calcium chloride treatment, polybrene mediated transfection, protoplast fusion, electroporation, viral or phage infection, encapsulation of the polynucleotide(s) in liposomes, and direct microinjection of the DNA into nuclei. In the case of mammalian cells, transfection may be either transient or stable. Preferred nucleic acids molecules of the invention are those encoding the light chain variable region selected from the group consisting of SEQ ID NOS: 25, 38, 39, 40, 48, 49, 50, 51, 52, 53, 56, 57, 58, 59, 60, 61, 62 and 63 and/or the heavy chain variable region selected from the group consisting of SEQ ID NOS: 33, 34, 35, 36, 37, 43, 44, 45, 46, 47, 54 and 55. More preferred are nucleic acids molecules encoding a heavy chain sequence comprising the amino acid sequence of SEQ ID NO: 64, and a light chain sequence comprising the amino acid sequence of SEQ ID NO: 65; encoding a heavy chain sequence comprising the amino acid sequence of SEQ ID NO: 66, and a light chain sequence comprising the amino acid sequence of SEQ ID NO: 67; or encoding a heavy chain sequence comprising the amino acid sequence of SEQ ID NO: 66, and a light chain sequence comprising the amino acid sequence of SEQ ID NO: 65; or encoding a heavy chain sequence comprising the amino acid sequence of SEQ ID NO: 114, and a light chain sequence comprising the amino acid sequence of SEQ ID NO: 65; or encoding a heavy chain sequence comprising the amino acid sequence of SEQ ID NO: 115, and a light chain sequence comprising the amino acid sequence of SEQ ID NO: 65; or encoding a heavy chain sequence comprising the amino acid sequence of SEQ ID NO: 116, and a light chain sequence comprising the amino acid sequence of SEQ ID NO: 65; or encoding a heavy chain sequence comprising the amino acid sequence of SEQ ID NO: 117, and a light chain sequence comprising the amino acid sequence of SEQ ID NO: 65; or encoding a heavy chain sequence comprising the amino acid sequence of SEQ ID NO: 118, and a light chain sequence comprising the amino acid sequence of SEQ ID NO: 65; or encoding a heavy chain sequence comprising the amino acid sequence of SEQ ID NO: 119, and a light chain sequence comprising the amino acid sequence of SEQ ID NO: 65; or encoding a heavy chain sequence comprising the amino acid sequence of SEQ ID NO: 120, and a light chain sequence comprising the amino acid sequence of SEQ ID NO: 65; or encoding a heavy chain sequence comprising the amino acid sequence of SEQ ID NO: 121, and a light chain sequence comprising the amino acid sequence of SEQ ID NO: 65; or encoding a heavy chain sequence comprising the amino acid sequence of SEQ ID NO: 122, and a light chain sequence comprising the amino acid sequence of SEQ ID NO: 65; or encoding a heavy chain sequence comprising the amino acid sequence of SEQ ID NO: 123, and a light chain sequence comprising the amino acid sequence of SEQ ID NO: 65; or encoding a heavy chain sequence comprising the amino acid sequence of SEQ ID NO: 124, and a light chain sequence comprising the amino acid sequence of SEQ ID NO: 65.

The present disclosure also provides an isolated nucleic acid comprising the heavy chain encoding nucleic acid sequence of a humanized FMC63 variant that binds to human CD19 as deposited in a microorganism with DSMZ on Feb. 5, 2010, having accession No. DSM 23302. The heavy chain encoded by the deposited nucleic acid sequence of a humanized FMC63 variant that binds to human CD19 comprises a heavy chain CDR1 comprising the amino acid sequence of SEQ ID NO: 27, a heavy chain CDR2 comprising the amino acid sequence of SEQ ID NO: 28, and a heavy chain CDR3 comprising the amino acid sequence of SEQ ID NO: 29.

The present disclosure also provides an isolated nucleic acid comprising the light chain encoding nucleic acid sequence of a humanized FMC63 variant that binds to human CD19 as deposited in a microorganism with DSMZ on Feb. 5, 2010, having accession No. DSM 23303. The light chain encoded by the deposited nucleic acid sequence of a humanized FMC63 variant that binds to human CD19 comprises a light chain CDR1 comprising the amino acid sequence of SEQ ID NO: 30, a light chain CDR2 comprising the amino acid sequence of SEQ ID NO: 31, and a light chain CDR3 comprising the amino acid sequence of SEQ ID NO: 32.

Thus the present disclosure also provides a humanized antibody or fragment thereof that binds to human CD19 encoded by the isolated nucleic acid comprising the heavy chain encoding nucleic acid sequence of a humanized FMC63 variant that binds to human CD19 as deposited in a microorganism with DSMZ on Feb. 5, 2010, having accession No. DSM 23302 and the isolated nucleic acid comprising the light chain encoding nucleic acid sequence of a humanized FMC63 variant that binds to human CD19 as deposited in a microorganism with DSMZ on Feb. 5, 2010, having accession No. DSM 23303.

In one embodiment the humanized antibody or fragment thereof that binds to human CD19 encoded by the isolated nucleic acid comprising the heavy chain encoding nucleic acid sequence of a humanized FMC63 variant that binds to human CD19 as deposited in a microorganism with DSMZ on Feb. 5, 2010, having accession No. DSM 23302 comprises a variant human IgG Fc region, preferably a variant human IgG1 Fc region, which comprises an amino acid substitution at amino acid position selected from the group consisting of 269, 274, 276, 298, 324 and 334, preferably selected from the group consisting of 269, 298 and 324, more preferably 298 and/or 324, wherein the amino acid position of each group member is indicated utilizing the numbering system set forth in Kabat.

Once DNA fragments encoding VH and VL segments are obtained, these DNA fragments can be further manipulated by standard recombinant DNA techniques, for example to convert the variable region genes to full-length antibody chain genes, or to fragments genes corresponding to the fragments described supra like Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame. The isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 constant region. For a Fab fragment heavy chain gene, the V[pi]-encoding DNA can be operatively linked to another DNA molecule encoding only the heavy chain CH1 constant region. The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region, preferably a kappa constant region. To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. ScL USA 85:5879-5883; McCafferty et al, (1990) Nature 348:552-554). Various techniques have been developed for the production of antibody fragments of humanized antibodies. Traditionally, these fragments were derived via proteolytic digestion of intact antibodies (see, e.g., Morimoto et al., Journal of Biochemical and Biophysical Methods, 24:107-117 (1992); and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology, 10: 163-167 (1992)). According to another approach, F(ab')2 fragments can be isolated directly from recombinant host cell culture. Other techniques for the production of antibody fragments will be apparent to the skilled practitioner. In other embodiments, the antibody of choice is a single-chain Fv fragment (scFv), see e.g. WO 1993/16185; U.S. Pat. No. 5,571,894; and U.S. Pat. No. 5,587,458. The antibody fragment may also be a "linear antibody", e.g., as described in U.S. Pat. No. 5,641,870, for example.

The nucleic acids that encode the antibodies of the present invention may be incorporated into an expression vector in order to express the protein. A variety of expression vectors may be utilized for protein expression. Expression vectors may comprise self-replicating extra-chromosomal vectors or vectors which integrate into a host genome. Expression vectors are constructed to be compatible with the host cell type. Thus expression vectors which find use in the present invention include but are not limited to those which enable protein expression in mammalian cells, bacteria, insect cells, yeast, and in in vitro systems. As is known in the art, a variety of expression vectors are available, commercially or otherwise, that may find use in the present invention for expressing antibodies.

Expression vectors typically comprise a protein operably linked with control or regulatory sequences, selectable markers, any fusion partners, and/or additional elements. By "operably linked" herein is meant that the nucleic acid is placed into a functional relationship with another nucleic acid sequence. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology, Methods in Enzymology 185, Academic Press, San Diego, Calif. (1990)). Generally, these expression vectors include transcriptional and translational regulatory nucleic acid operably linked to the nucleic acid encoding the antibody, and are typically appropriate to the host cell used to express the protein. In general, the transcriptional and translational regulatory sequences may include promoter sequences, ribosomal binding sites, transcriptional start and stop sequences, translational start and stop sequences, and enhancer or activator sequences. As is also known in the art, expression vectors typically contain a selection gene or marker to allow the selection of transformed host cells containing the expression vector. Selection genes are well known in the art and will vary with the host cell used. For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr− host cells with methotrexate selection/amplification) and the neo gene (for G418 selection).

Suitable host cells for cloning or expressing the DNA in the vectors herein are prokaryote, yeast, or higher eukaryote cells. Suitable prokaryotes for this purpose include eubacteria, including gram-negative or gram-positive organisms, for example, Enterobacteriaceae such as *Escherichia*, e.g., *E. coli, Enterobacter, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Suitable *E. coli* cloning hosts include *E. coli* 294 (ATCC 31,446), *E. coli* B, *E. coli* X1776 (ATCC 31,537), and *E. coli* W3110 (ATCC 27,325).

In addition to prokaryotes, eukaryotic microbes such as filamentous fungi or yeast are suitable cloning or expression hosts. *Saccharomyces cerevisiae*, or common baker's yeast, is the most commonly used among lower eukaryotic host microorganisms. However, a number of other genera, species, and strains are commonly available and useful, such as *Schizosaccharoriyces pombe; Kluyveromyces* hosts including *K. lactis, K. fragilis* (ATCC 12,424), *K. bulgaricus* (ATCC 16,045), *K. wickeramii* (ATCC 24,178), K. WaltH (AJCC 56,500), *K. drosoparum* (ATCC 36,906), *K. thermotolerans*, or *K. marxianusyarrowia* (EP 402226); *Pichia pastoris* (EP 183,070); *Candida; Trichoderma reesia* (EP 244234); *Neurospora crassa; Schwanniomyces* such as *Schwanniomyces occidentalis*; and filamentous fungi including *Neurospora, Penicillium, Tolypocladium*, or *Aspergillus* hosts such as *A. nidulans* or *A. niger*.

Suitable host cells for the expression of the humanized antibodies of the invention are derived from multicellular organisms. Examples of invertebrate cells include plaril and insect cells. Numerous baculoviral strains and variants and corresponding permissive insect host cells from hosts such as *Spodoptera frugiperda* (caterpillar), *Aedes augypti* (mosquito), *Aedes albopictus* (mosquito), *Drosophila melanogaster* (fruitfly), and *Bombyx mori* have been identified. A variety of viral strains for transfection are publicly available, for example, the L-1 variant of *Autographa californica* NPV and the Bm-5 strain of *Bombyx mori* NPV, and such viruses may be used, particularly for transfection of *Spodoptera frugiperda* cells. Plant cell cultures of cotton, corn, potato, soybean, petunia, tomato, and tobacco can also be utilized as hosts.

Host cells for expressing the recombinant antibodies of the invention are preferably mammalian host cells which include Chinese Hamster Ovary (CHO cells) (including dhfr<–> CHO cells, described in Urlaub and Chasin, (1980) Proc. Natl. Acad. ScL USA 77:4216-4220, used with a DHFR selectable marker, e.g., as described in R. J. Kaufman and P. A. Sharp (1982) J. MoI. Biol 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338841 (to Bebbington). When recombinant antibody genes are introduced into mammalian host cells, the antibodies are produced by culturing the host cells for a period of time sufficient to allow for expression of the antibody in the host cells or, more preferably, for secretion of the antibody into the culture medium in which the host cells are grown. Host cells useful for producing antibodies that bind to human CD19 may be cultured in a variety of media. Commercially available media such as Ham's F10 (Sigma), Minimal Essential Medium ((MEM), (Sigma), RPMI-1640 (Sigma or Chemie Brunschwig AG, PAA, Basel, Switzerland), and Dulbecco's Modified Eagle's Medium ((DMEM), Sigma) are suitable for culturing the host cells. Antibodies can be recovered from the culture medium using standard protein purification methods.

Antibodies may be operably linked to a fusion partner to enable targeting of the expressed protein, purification, screening, display, and the like. Fusion partners may be linked to the antibody sequence via a linker sequences. The linker sequence will generally comprise a small number of amino acids, typically less than ten, although longer linkers may also be used. Typically, linker sequences are selected to be flexible and resistant to degradation. As will be appreciated by those skilled in the art, any of a wide variety of sequences may be used as linkers. For example, a common linker sequence comprises the amino acid sequence GGGGS (SEQ ID NO: 126).

A fusion partner may be a targeting or signal sequence that directs antibody and any associated fusion partners to a desired cellular location or to the extracellular media. As is known in the art, certain signaling sequences may target a protein to be either secreted into the growth media, or into the periplasmic space, located between the inner and outer membrane of the cell. A fusion partner may also be a sequence that encodes a peptide or protein that enables purification and/or screening. Such fusion partners include but are not limited to polyhistidine tags (His-tags) (for example H6 and H10 or other tags for use with Immobilized Metal Affinity Chromatography (IMAC) systems (e.g. Ni<+2> affinity columns)), GST fusions, MBP fusions, Strep-tag, the BSP biotinylation target sequence of the bacterial enzyme BirA, and epitope tags which are targeted by antibodies (for example c-myc tags, flag-tags, and the like). As will be appreciated by those skilled in the art, such tags may be useful for purification, for screening, or both.

Construction and Production of Antibodies

Antibodies can be produced by recombinant DNA techniques known to the skilled person. In additional antibodies can be produced by enzymatic or chemical cleavage of naturally occurring antibodies. Humanized antibodies of the present invention may be constructed by transferring one or more CDRs or portions thereof from VH and/or VL regions from a non-human animal (e.g., mouse) to one or more framework regions from human VH and/or VL regions. Optionally, human framework residues thus present in the VH and/or VL regions may be replaced by corresponding non-human (e.g., mouse) residues when needed or desired for decreasing immunogenicity of the antibody and/or maintaining binding affinity.

Optionally, non-human amino acid residues present in the CDRs may be replaced with human residues. Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al).

Humanized antibodies of the present invention may be constructed wherein the human acceptor molecule for the heavy chain variable region is selected based on homology considerations between potential acceptor molecule variable regions and the heavy chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same heavy chain class as the murine donor molecule, and of the same canonical structural class of the variable region of the murine donor molecule. Secondary considerations for selection of the human acceptor molecule for the heavy chain variable region elude homology in CDR length between the murine donor molecule and the human acceptor molecule. Human acceptor antibody molecules are preferably selected by homology search to the V-BASE database, although other databases such as the Kabat and the public NCBI databases may be used as well.

Humanized antibodies of the present invention may be constructed wherein the human acceptor molecule for the light chain variable region is selected based on homology considerations between potential acceptor molecule variable regions and with the light chain variable region of the murine antibody. Germline candidate human acceptor molecules are preferred to reduce potential immunogenicity. Germline databases are made up of antibody sequences that read through the end of the heavy chain FW3 region and partially into the CDR3 sequence. For selection of a FW4 region, databases of mature antibody sequences which have been derived from the selected germline molecule can be searched or antibody sequences which have been derived from the selected germline molecule from a human donor can be used. Human acceptor molecules are preferably selected from the same light chain class as the murine donor molecule, and of the same canonical structural class of the variable region of the murine donor molecule. Secondary considerations for selection of the human acceptor molecule for the light chain variable region include homology in CDR length between the murine donor molecule and the human acceptor molecule. Human acceptor antibody molecules are preferably selected by homology searches to the V-BASE database, and other databases such as the Kabat and the public NCBI databases may be used as well.

Methods for humanizing a nonhuman antibody are described herein, including in the Examples below.

The present invention provides a method of producing a humanized antibody or fragment thereof that binds to human CD19 comprising culturing a host cell comprising an isolated nucleic acid encoding the humanized antibody or fragment thereof that binds to human CD19 or a vector comprising an isolated nucleic acid encoding the humanized antibody or fragment thereof that binds to human CD19 so that the nucleic acid is expressed and the antibody produced. Preferably the antibody is isolated.

As host cells, nucleic acids and vectors, the ones described supra can be used. Expression of the nucleic acids can be obtained by, for example, a combination of recombinant DNA techniques and gene transfection methods as is well known in the art (e.g., Morrison, S. (1985) Science 229:1202) and as further outlined supra. For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into vectors such as expression vectors. The expression vector and expression control sequences are chosen to be compatible with the expression host cell used.

The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VK segment is operatively linked to the CL segment within the vector.

Characterization and Purification of Anti-CD19 Antibodies.

Antibodies of the invention can be tested for binding to human CD19 by, for example, standard ELISA or by binding to Raji tumor cells. Antibodies of the present invention may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. To purify anti-CD19 antibodies, selected host cells can be grown in e.g spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity.

Immunoconjugates

In another aspect, the present invention provides a humanized anti-CD19 antibody or a fragment thereof that binds to human CD19, linked to a therapeutic agent, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be linked to an antibody of the invention include duocarmycins, calicheamicins, maytansines and auristatins, and derivatives thereof. An example of a calicheamicin antibody conjugate is commercially available (Mylotarg®; American Home Products). Cytotoxins can be linked to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55: 199-215; Trail, P. A. et al. (2003) Cancer Immunol. Immunother. 52: 328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3: 1089-1091; Senter, P. D. and Springer, C J. (2001) Adv. Drug Deliv. Rev. 53: 247-264. Antibodies of the present invention also can be linked to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine<131>, indium<111>, yttrium<90> and lutetium<177>. Methods for preparing radioimmunconjugates are established in the art. Examples of radioimmunoconjugates are commercially available, including Zevalin® (EDEC Pharmaceuticals) and Bexxar® (Corixa Pharmaceuticals), and similar methods can be used to prepare radioimmunoconjugates using the antibodies of the invention. The antibody immunoconjugates of the invention can be used to modify a given biological response, and the drug moiety is not to be construed as limited to classical chemical therapeutic agents.

For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-[gamma]; or, biological response modifiers such as, for example, lymphokines, interleukin-1 ("IL-I"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for linking such therapeutic agents to antibodies are well known, see, e.g., Arnon et al, "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al, "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al, Immunol. Rev., 62: 119-58 (1982).

Pharmaceutical Compositions

In another aspect, the present invention provides a composition, e.g., a pharmaceutical composition, comprising the humanized antibody or fragment thereof, of the present invention, and a pharmaceutically acceptable carrier. Such compositions may include one or a combination of (e.g., two or more different) antibodies or immunoconjugates of the invention. For example, a pharmaceutical composition of the invention can comprise a combination of antibodies (or immunoconjugates) that bind to different epitopes on the target antigen or that have complementary activities. Pharmaceutical compositions of the invention also can be administered in combination therapy, i.e., combined with other agents. For example, the combination therapy can include an anti-CD19 antibody of the present invention combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody or immunoconjugate, may be coated in a material to protect the compound from the action of acids and other natural conditions that may inactivate the compound. Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

In another aspect, the present invention provides a composition comprising an immunoconjugate comprising the humanized antibody or fragment thereof that binds to human CD19 linked to a therapeutic agent and a pharmaceutically acceptable carrier. Immunoconjugates and therapeutic agents which can be used are as described supra.

A pharmaceutical composition of the invention may also include a pharmaceutically acceptable antioxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic-acid (EDTA), sorbitol, tartaric acid, phosphoric acid, and the like. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic and Other Uses

The humanized antibodies of the present invention have numerous in vitro and in vivo diagnostic and therapeutic utilities involving the diagnosis and treatment of CD19 mediated disorders. For example, these molecules can be administered to cells in culture, in vitro or ex vivo, or to human subjects, e.g., in vivo, to treat, prevent and to diagnose a variety of CD19-mediated disorders. Preferred subjects are human and include patients having disorders mediated by CD19 activity (CD19 mediated disorders). The methods are particularly suitable for treating human patients having a CD19-mediated disorder associated with aberrant B cell populations.

A "patient" for the purposes of the present invention includes both humans and other animals, preferably mammals and most preferably humans. Thus the antibodies of the present invention have both human therapy and veterinary applications. The term "treatment" or "treating" in the present invention is meant to include therapeutic treatment, as well as prophylactic, or suppressive measures for a disease or disorder. Thus, for example, successful administration of an antibody prior to onset of the disease results in treatment of the disease.

As another example, successful administration of an antibody after clinical manifestation of the disease to combat the symptoms of the disease comprises treatment of the disease. "Treatment" and "treating" also encompasses administration of an antibody after the appearance of the disease in order to eradicate the disease. Successful administration of an antibody after onset and after clinical symptoms have developed, with possible abatement of clinical symptoms and perhaps amelioration of the disease, comprises treatment of the disease.

Those "in need of treatment" include mammals already having the disease or disorder, as well as those prone to having the disease or disorder, including those in which the disease or disorder is to be prevented.

In a particular embodiment, the humanized antibodies are used in vivo to treat, prevent or diagnose a variety of CD19-mediated diseases. Thus the invention provides a method for treating a CD19 mediated disorder in a subject, the method comprising administering to the subject a therapeutically effective amount of the humanized antibody or fragment thereof. Exemplary CD19 mediated disorders include autoimmune disorder including rheumatoid arthritis, cancer, non-Hodgkin's lymphoma, acute lymphocytic leukemia (ALL), chronic lymphocytic leukemia (CLL), hairy cell leukemia, Burkitt's lymphoma, anaplastic large-cell lymphomas (ALCL), cutaneous T-cell lymphomas, nodular small cleaved-cell lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, anti-CD20 antibody resistant B-cell cancers and other B-cell lymphomas and leukemias. Anti-CD20 antibody resistant B-cell cancers are e.g. rituximab (Rituxan®) resistant B-cell cancers, which is the preferred anti-CD20 antibody resistant B-cell cancer. Preferred cancers are hematologic cancers, especially cancers relating to lymphomas and leukemias expressing CD19, in particular non-Hodgkin's lymphoma, acute lymphocytic leukemia (ALL), chronic lymphocytic leukemia (CLL), and hairy cell leukemia. Preferred CD19 mediated disorders to be treated with the antibody of the invention are selected from the group consisting of non-Hodgkin's lymphoma, acute lymphocytic leukemia (ALL), chronic lymphocytic leukemia (CLL), hairy cell leukemia, rheumatoid arthritis, systemic lupus erythematosus (SLE), and anti-CD20 antibody resistant B-cell cancers. More preferred CD19 mediated disorders to be treated with the antibody of the invention are rheumatoid arthritis, non-Hodgkin's lymphoma or anti-CD20 antibody resistant B-cell cancers.

"Autoimmune disorders" include allogenic islet graft rejection, alopecia greata, ankylosing spondylitis, antiphospholipid syndrome, autoimmune Addison's disease, antineutrophil cytoplasmic autoantibodies (ANCA), autoimmune diseases of the adrenal gland, autoimmune hemolytic anemia, autoimmune hepatitis, autoimmune myocarditis, autoimmune neutropenia, autoimmune oophoritis and orchitis, autoimmune thrombocytopenia, autoimmune urticaria, Behcet's disease, bullous pemphigoid, cardiomyopathy, Castleman's syndrome, celiac spruce-dermatitis, chronic fatigue immune disfunction syndrome, chronic inflammatory demyelinating polyneuropathy, Churg-Strauss syndrome, cicatrical pemphigoid, CREST syndrome, cold agglutinin disease, Crohn's disease, dermatomyositis, discoid lupus, essential mixed cryoglobulinemia, factor VIII deficiency, fibromyalgia-fibromyositis, glomerulonephritis, Grave's disease, Guillain-Barre, Goodpasture's syndrome, graft-versus-host disease (GVHD), Hashimoto's thyroiditis, hemophilia A, idiopathic pulmonary fibrosis, idiopathic thrombocytopenia purpura (ITP), IgA neuropathy, IgM polyneuropathies, immune mediated thrombocytopenia, juvenile arthritis, Kawasaki's disease, lichen planrus, lupus erthematosis, Meniere's disease, mixed connective tissue disease, multiple sclerosis (MS), type 1 diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobinulinemia, primary biliary cirrhosis, psoriasis, psoriatic arthritis, Reynauld's phenomenon, Reiter's syndrome, rheumatoid arthritis (RA), sarcoidosis, scleroderma, Sjogren's syndrome, solid organ transplant rejection, stiff-man syndrome, systemic lupus erythematosus (SLE), takayasu arteritis, temporal arteristis/giant cell arteritis, thrombotic thrombocytopenia purpura, ulcerative colitis, uveitis, vasculitides such as dermatitis herpetiformis vasculitis, vitiligo, anti-neutrophil cytoplasmic antibody associated vasculitis, graft vs. host disease, cryoglobulinemia, IgM mediated neuropathy, neuromyelitis optica, idiopathic membranous nephropathy, opsoclonus myoclonus, and Wegner's granulomatosis.

Furthermore, given the expression of CD19 on various tumor cells and given the fact that the humanized antibody or fragment thereof of the present invention inhibits proliferation of malignant B-cells expressing CD19 as mentioned supra, the CD19 mediated disease is preferably a tumorigenic disorder like cancer, e.g., a disorder characterized by the presence of tumor cells expressing CD19 including, for example, non-Hodgkin's lymphoma (NHL), acute lymphocytic leukemia (ALL), chronic lymphocytic leukemia (CLL), hairy cell leukemia Burkitt's lymphoma, anaplastic large-cell lymphomas (ALCL), multiple myeloma, cutaneous T-cell lymphomas, nodular small cleaved-cell lymphomas, lymphocytic lymphomas, peripheral T-cell lymphomas, Lennert's lymphomas, immunoblastic lymphomas, T-cell leukemia/lymphomas (ATLL), adult T-cell leukemia (T-ALL), entroblastic/centrocytic (cb/cc) follicular lymphomas cancers, diffuse large cell lymphomas of B lineage, angioimmunoblastic lymphadenopathy (AILD)-like T cell lymphoma, HIV associated body cavity based lymphomas, Embryonal Carcinomas, undifferentiated carcinomas of the rhino-pharynx (e.g., Schmincke's tumor), Castleman's disease, Kaposi's Sarcoma, Multiple Myeloma, Waldenstrom's macroglobulinemia, anti-CD20 antibody resistant B-cell cancers and other B-cell lymphomas and leukemias.

Thus in a further aspect the present invention provides a method of inhibiting growth of tumor cells expressing CD19, comprising contacting the cells with the humanized antibody or fragment thereof of the invention, in an amount effective to inhibit growth of tumor cells. Tumor cells are typically selected from human Burkitt lymphoma cells, human B cell precursor leukemia cells, human B cell leukemia cells or human B-cell lymphoma cells, preferably human Burkitt lymphoma cells or human B-cell lymphoma cells.

Given the fact that the humanized antibody or fragment thereof of the present invention causes B-cell depletion in blood, the present invention further provides a method of depleting B cells in a subject comprising administering to the subject the humanized antibody or fragment thereof of the invention in an amount effective to deplete B cells from the subject.

In one embodiment, the antibodies of the invention can be used to detect levels of CD19, or levels of cells which contain CD19 on their membrane surface, which levels can then be linked to certain disease symptoms. Alternatively, the antibodies can be used to inhibit or block CD19 function which, in turn, can be linked to the prevention or amelioration of certain disease symptoms, thereby implicating CD19 as a mediator of the disease. This can be achieved by contacting a sample and a control sample with the anti-CD19 antibody under conditions that allow for the formation of a complex between the antibody and CD19. Any complexes formed between the antibody and CD19 are detected and compared in the sample and the control. In light of the specific binding of the antibodies of the invention for CD19, the antibodies of the invention can be used to specifically detect CD19 expression on the surface of cells and, moreover, can be used to purify CD19 via immunoaffinity purification.

In another embodiment, the antibodies of the invention can be initially tested for binding activity associated with therapeutic or diagnostic use in vitro. For example, compositions of the invention can be tested using the flow cytometric assays described in the Examples below.

The present disclosure further provides the use of a humanized antibody or fragment thereof as a medicament and the use of a humanized antibody or fragment thereof in the preparation of a medicament for the treatment of a CD19 mediated disorder. In a further embodiment the present disclosure provides the humanized antibody or fragment thereof for use as a medicament. Also provided by the present disclosure is the humanized antibody or fragment thereof for use in a method for treating a CD19 mediated disorder. CD19 mediated disorders are the ones as described supra.

As previously described, human anti-CD19 antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation.

For administration of the antibody, the dosage ranges from about 0.0001 to 100 mg/kg, and more usually 0.01 to 10 mg/kg, of the host body weight. An exemplary treatment regime entails administration once per week, once every two weeks, once every three weeks, once every four weeks, once a month, once every 3 months or once every three to 6 months.

The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml. Alternatively, antibody can be administered as a sustained release formulation, in which case less frequent administration is required. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated.

Actual dosage levels of the active ingredients, i.e. the antibody in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of an anti-CD19 antibody of the invention preferably results in a decrease in severity of disease symptoms, an increase in frequency and duration of disease symptom-free periods, and/or a prevention of impairment or disability due to the disease affliction. For example, for the treatment of a tumorogenic disorder (CD19<+> tumors), a "therapeutically effective amount" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The antibody or the composition of the present invention can be administered via one or more routes of administration using one or more of a variety of methods known in the art. As will be appreciated by the skilled artisan, the route and/or mode of administration will vary depending upon the desired results. Preferred routes of administration include intravenous, intramuscular, intradermal, intraperitoneal, subcutaneous, spinal or other parenteral routes of administration, for example by injection or infusion. More preferred routes of administration are intravenous or subcutaneous. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, for example, intranasally, orally, vaginally, rectally, sublingually or topically.

Article of Manufacture and Kit

In another embodiment of the disclosure, an article of manufacture comprising the humanized antibody or fragment thereof, the composition or the immunoconjugate of the invention for the treatment of a CD19 mediated disorder is provided. The article of manufacture may comprise a container and a label or package insert on or associated with the container. Suitable containers include, for example, bottles, vials or syringes. The containers may be formed from a variety of materials such as glass or plastic. The container holds a composition that may be effective for treating the condition and may have a sterile access port (e.g., the container may be an intravenous solution bag or a vial having a stopper pierceable by a hypodermic injection needle). At least one active agent in the composition may be the humanized antibody described herein. The label or package insert may indicate that the composition may be used for treating the condition of choice, such as cancer. In one embodiment, the label or package insert may indicate that the composition comprising the humanized antibody may be used to treat a CD19-mediated disorder.

Moreover, the article of manufacture may comprise (a) a first container with a composition contained therein, wherein the composition comprises the humanized antibody herein, and (b) a second container with a composition contained therein, wherein the composition comprises a therapeutic agent other than the humanized antibody. The article of manufacture in this embodiment of the disclosure may further comprise a package insert indicating that the first and second compositions can be used in combination to treat a CD19 mediated disease or disorder. Such therapeutic agent may be any of the adjunct therapies described in the preceding section (e.g., a thrombolytic agent, an anti-platelet agent, a chemotherapeutic agent, an anti-angiogenic agent, an anti-hormonal compound, a cardioprotectant, and/or a regulator of immune function in a mammal, including a cytokine).

Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Also within the scope of the present invention are kits comprising the antibody, the compositions or the immunoconjugates of the invention and instructions for use. The kit can further contain one or more additional reagents, such as an immunosuppressive reagent, a cytotoxic agent or a radiotoxic agent, or one or more additional humanized antibodies of the invention (e.g., a humanized antibody having a complementary activity which binds to an epitope in the CD 19 antigen distinct from the first humanized antibody).

Deposit of Material:

The following materials have been deposited with the Deutsche Sammlung von Mikroorganismen and Zellkulturen GmbH (DSMZ), Inhoffenstr. 7 B, 38124 Braunschweig, Germany:

Microorganism (*E. coli*) deposited with DSMZ on Feb. 5, 2010, having accession No. DSM 23303, comprising isolated nucleic acid comprising the light chain encoding nucleic acid sequence of humanized FMC63 variant that binds to human CD19 as described in Example 1. Microorganism (*E. coli*) deposited with DSMZ on Feb. 5, 2010, having accession No. DSM 23302, which comprises isolated nucleic acid comprising the heavy chain encoding nucleic acid sequence of humanized FMC63 variant that binds to human CD19 as described in Example 1. These deposits were made under the provisions of the Budapest Treaty on the International Recognition of the Deposit of Microorganisms for the Purpose of Patent Procedure and the Regulations thereunder (Budapest Treaty).

Without further description, it is believed that one of ordinary skill in the art may, using the preceding description and the following illustrative examples, make and utilize the agents of the present disclosure and practice the claimed methods. The following working examples are provided to facilitate the practice of the present disclosure, and are not to be construed as limiting in any way the remainder of the disclosure.

EXAMPLES

Example 1

Humanization of Mouse Monoclonal FMC63 Antibody Against Human CD19

Humanizing the anti-human CD19 murine antibody FMC63 including selection of human acceptor frameworks, back mutations, and mutations that substantially retain and/or improve the binding properties of human CDR-grafted acceptor frameworks is described herein.

FMC63 is a murine IgG2a, kappa antibody isolated from mice immunized with the human prolymphocytic leukaemia cell line JVM3 (Zola H. et al (1991), Immunol Cell Biol., 69:411-22.), and for which variable regions are known and publicly available (Heavy chain NCBI accession number, CAA74659 (SEQ ID NO: 1); Light chain NCBI accession number, CAA74660 (SEQ ID NO: 2)). Methods for assaying antigen-binding affinity are well known in the art and include half-maximal binding assays, competition assays, and Scatchard plot analysis.

Design of the Reshaped Variable Regions

Selection of human acceptor frameworks: Homology matching was used to choose human acceptor frameworks to graft FMC63 CDRs. Databases (e.g. a database of germline variable genes from the immunoglobulin loci of human and mouse, VBASE2 (Retter I. et al, 2005, Nucleic Acids Res., 33, Database issue D671-D674), or the Kabat database (Johnson G. et al, 2000, Nucleic Acids Res., 28, p 214-218)) or publications (e.g., Kabat et al, Sequences of Proteins of Immunological Interest, 1992) may be used to identify the human subfamilies to which the murine heavy and light chain V regions belong and determine the best-fit human germline framework to use as the acceptor molecule. Selection of VH and VL sequences within these subfamilies to be used as acceptor may be based upon sequence homology and/or a match of structure of the CDR1 and CDR2 regions to help preserve the appropriate relative presentation of the six CDRs after grafting.

For example, use of the VBASE2 database indicates that the kappa light chain of FMC63 is of the kappa one subfamily given that good homology was identified between the FMC63 VL framework and the members of the human kappa subfamily I. The highest homology and identity of both CDRs and framework sequences is observed for four germline sequences: IGKV1-5*03 (VBASE2 ID humIGKV087) (SEQ ID NO:3), IGKV1-27*01 (VBASE2 ID humIGKV106) (SEQ ID NO:4), IGKV1-39*01 (VBASE2 ID humIGKV115) (SEQ ID NO:5), and IGKV1-12*01 (VBASE2 ID humIGKV094) (SEQ ID NO:6); which have a sequence identity of 70.4%, 75%, 76.1%, and 72.7% respectively for the whole sequence up to CDR3 and a sequence identity of 74.3%, 78.6%, 78.6%, and 77.1% respectively for frameworks regions. Since complete LCDR3 and framework 4 regions are not included in VBASE2, best matching JK segment sequences to human acceptor framework were identified by analysis of complementary DNA (cDNA) prepared from healthy donor B-cell mRNA, which were subsequently amplified using a degenerate primer and immunoglobulin light chain first constant domain from kappa isotype as shown in Table 1. Using this approach, best matching sequences from amplifications were: SEQ ID NO: 7, SEQ ID NO: 8, SEQ ID NO: 9, and SEQ ID NO: 10 for IGKV1-5*03 (SEQ ID NO: 3), IGKV1-27*01 (SEQ ID NO: 4), IGKV1-39*01 (SEQ ID NO: 5), and IGKV1-12*01 (SEQ ID NO: 6) respectively.

TABLE 1

| Forward Primer Sequence (5'→3') | Reverse Primer Sequence (5'→3') |
|---|---|
| GATCGGATCCACTGGTGATATTG TGATGACYCAGWCTCC (SEQ ID NO: 70) | GATCGCGGCCGCACACTCTCCCCTG TTGAAGCTCTT (SEQ ID NO: 71) |
| Germline variable region | Amplified variable region |
| Hum IGKV 087 (SEQ ID NO: 3) | pAE18 VL-2a clone#39 (SEQ ID NO: 7) |
| Hum IGKV 106 (SEQ ID NO: 4) | pAE18 VL-2a clone#40 (SEQ ID NO: 8) |
| Hum IGKV 115 (SEQ ID NO: 5) | pAE18 VL-2a clone#43 (SEQ ID NO: 9) |
| Hum IGKV 094 (SEQ ID NO: 6) | pAE18 VL-2a clone#44 (SEQ ID NO: 10) |

Similarly, use of VBASE2 indicates that the VH sequence of FMC63 through to framework three falls in the human VH subfamily III. Within the human VH subfamily III, FMC63 shows the highest sequence homology with IGHV3-33*01 (VBASE2-ID: humIGHV199) (SEQ ID NO: 11), IGHV3-11*01 (VBASE2-ID; humIGHV175) (SEQ ID NO: 12), IGHV3-30*18 (VBASE2-ID: humIGHV195) (SEQ ID NO: 13), and IGHV3-48*01 (VBASE2-ID: humIGHV031) (SEQ ID NO: 14), which exhibit sequence homology above 70.4% for framework and CDR regions. As for the light chain, a source to identify compatible JH segments is cDNAs prepared from healthy donor B-cell mRNA amplified with degenerate primers and IgM heavy chain first constant domain (Table 2). The following sequences: SEQ ID NO: 15, SEQ ID NO: 16, SEQ ID NO: 17, and SEQ ID NO: 18 were closest to IGHV3-33*01 (VBASE2-ID: humIGHV199) (SEQ ID NO: 11), IGHV3-11*01 (VBASE2-ID: humIGHV175) (SEQ ID NO: 12), IGHV3-30*03 (VBASE2-ID: humIGHV195) (SEQ ID NO: 13), and IGHV3-48*01 (VBASE2-ID: humIGHV031) (SEQ ID NO: 14) respectively.

TABLE 2

| Forward Primer Sequence (5'→3') | Reverse Primer Sequence (5'→3') |
|---|---|
| GATCGGATCCACTGGTGAGGTGCAGCTGGT GGAGTC (SEQ ID NO: 72) | GATCGCGGCCGCTGG AAGAGGCACGTTCTTTTCT TT (SEQ ID NO: 73) |
| GATCGGATCCACTGGTCAGGTYCAGCTKGT GCAGTCTGG (SEQ ID NO: 113) | |
| Germline variable region | Primers | Amplified variable region |
| Hum IGHV 199 (SEQ ID NO: 11) | SEQ ID NO: 72 SEQ ID NO: 73 | pAE18 VH-3a clone#2 (SEQ ID NO: 15) |
| Hum IGHV 175 (SEQ ID NO: 12) | SEQ ID NO: 72 SEQ ID NO: 73 | pAE18 VH-3a clone#5 (SEQ ID NO: 16) |
| Hum IGHV 195 (SEQ ID NO: 13) | SEQ ID NO: 113 SEQ ID NO: 73 | pAE18 VH-1b clone#16 (SEQ ID NO: 17) |
| Hum IGHV 031 (SEQ ID NO: 14) | SEQ ID NO: 113 SEQ ID NO: 73 | pAE18 VH-1b clone#20 (SEQ ID NO: 18) |

Making Initial CDR Grafted Human Variable Regions

Human VH and VL fragments prepared above were used to initiate humanization process. cDNAs were used as templates for CDR grafting using overlap PCR assembly to provide first humanized candidates based on the following heavy and light chains: VH2 (SEQ ID NO: 19), VH5 (SEQ ID NO: 20), VH16 (SEQ ID NO: 21), VH20 (SEQ ID NO: 22), VL39 (SEQ ID NO: 23), VL40 (SEQ ID NO: 24), VL43 (SEQ ID NO: 25), and VL44 (SEQ ID NO: 26), in which original CDRs have been replaced with FMC63 CDRs as shown in Table 3.

TABLE 3

FMC63 CDR regions.

| | Heavy chain | | Light chain | |
|---|---|---|---|---|
| | Amino-acid sequence | SEQ ID NO: | Amino-acid sequence | SEQ ID NO: |
| CDR1 | GVSLPDYGVS | 27 | RASQDISKYLN | 30 |
| CDR2 | VIWGSETTYYNSALKS | 28 | HTSRLHS | 31 |
| CDR3 | HYYYGGSYAMDY | 29 | QQGNTLPYT | 32 |

VH2, VH5, VH16 and VH20 heavy chains were based on cDNA encoding SEQ ID NO: 15, SEQ ID NO: 16, SEQ ID NO: 17, and SEQ ID NO: 18, respectively, with CDRs exchanged for FMC63 CDRs using a four-fragment assembly PCR strategy as described in Tables 4, and 5. A similar strategy was used for VL39, VL40, VL43, and VL44 as shown in Tables 6, and 7.

For heavy chains, products of PCR-amplifications described in Table 4, were subcloned by running a secondary PCR using adaptor primers (sense primer, HindIII VJ2C (SEQ ID NO: 93); and anti-sense primer, SalI adaptor (SEQ ID NO: 92)) to append a SalI site at the 3' end of the variable domain cDNA (see below). Amplifications described in Table 6 allow direct Kappa chains cloning into a mammalian cell expression vector (described below). In this instance, products contained variable as well as full-length constant kappa domain and were cloned in a mammalian cell expression vector using a BamHI and NotI site strategy.

TABLE 4

Summary of templates and primers used to construct 1st CDR-grafted heavy chain variable regions.

| Construct | Template | Fragment 1 PCR primers | Fragment 2 PCR primers | Fragment 3 PCR primers | Fragment 4 PCR primers |
|---|---|---|---|---|---|
| VH2/FMC6 3 grafted (SEQ ID NO: 19) | pAE18 VH-3a clone#2 (SEQ ID NO: 15) | CMV-IE Forward (SEQ ID NO: 74) and VH2 mCDR1 linker Reverse (SEQ ID NO: 76) | VH2 mCDR1 linker Forward (SEQ ID NO: 77) and VH2 mCDR2 linker Reverse (SEQ ID NO: 78) | VH2 mCDR2 linker Forward (SEQ ID NO: 79) and VH2 mCDR3 linker Reverse (SEQ ID NO: 80) | VH2 mCDR3 linker Forward (SEQ ID NO: 81) and BGH Reverse (SEQ ID NO: 75) |
| VH5/FMC6 3 grafted (SEQ ID NO: 20) | pAE18 VH-3a clone#5 (SEQ ID NO: 16) | CMV-IE Forward (SEQ ID NO: 74) and VH5 mCDR1 linker Reverse (SEQ ID NO: 82) | VH5 mCDR1 linker Forward (SEQ ID NO: 83) and VH20 mCDR2 linker Reverse (SEQ ID NO: 89) | VH5 mCDR2 linker Forward (SEQ ID NO: 84) and VH5 mCDR3 linker Reverse (SEQ ID NO: 85) | VH5 mCDR3 linker Forward (SEQ ID NO: 86) and BGH Reverse (SEQ ID NO: 75) |
| VH16/FMC 63 grafted (SEQ ID NO: 21) | pAE18 VH-1b clone#16 (SEQ ID NO: 17) | CMV-IE Forward (SEQ ID NO: 74) and VH5 mCDR1 linker Reverse (SEQ ID NO: 82) | VH2 mCDR1 linker Forward (SEQ ID NO: 77) and VH2 mCDR2 linker Reverse (SEQ ID NO: 78) | VH2 mCDR2 linker Forward (SEQ ID NO: 79) and VH16 mCDR3 linker Reverse (SEQ ID NO: 87) | VH2 mCDR3 linker Forward (SEQ ID NO: 81) and BGH Reverse (SEQ ID NO: 75) |
| VH20/FMC 63 grafted (SEQ ID NO: 22) | pAE18 VH-1b clone#20 (SEQ ID NO: 18) | CMV-IE Forward (SEQ ID NO: 74) and VH20 mCDR1 linker Reverse (SEQ ID NO: 88) | VH2 mCDR1 linker Forward (SEQ ID NO: 77) and VH20 mCDR2 linker Reverse (SEQ ID NO: 89) | VH20 mCDR2 linker Forward (SEQ ID NO: 90) and VH20 mCDR3 linker Reverse (SEQ ID NO: 91) | VH2 mCDR3 linker Forward (SEQ ID NO: 81) and BGH Reverse (SEQ ID NO: 75) |

TABLE 5

Sequences of primers used to construct selected human heavy chain 1st CDR - grafted variable regions.

| Primer | Sequence (5'→3') |
|---|---|
| CMV-IE Forward (SEQ ID NO: 74) | CGC AAA TGG GCG GTA GGC GTG |
| BGH Reverse (SEQ ID NO: 75) | TAG AAG GCA CAG TCG AGG |
| VH2 mCDR1 linker Reverse (SEQ ID NO: 76) | GCT CAC GCC GTA GTC GGG CAG GCT CAC GCC AGA CGC TGC ACA GGA GAG TCT C |
| VH2 mCDR1 linker Forward (SEQ ID NO: 77) | GGC GTG AGC CTG CCC GAC TAC GGC GTG AGC TGG GTC CGC CAG GCT CCA GG |
| VH2 mCDR2 linker Reverse (SEQ ID NO: 78) | GGC GCT GTT GTA GTA GGT TGT CTC GGA GCC CCA GAT CAC TGC CAC CCA CTC CAG CCC CTT G |
| VH2 mCDR2 linker Forward (SEQ ID NO: 79) | GGC TCC GAG ACA ACC TAC TAC AAC AGC GCC CTG AAG AGC CGA TTC ACC ATC TCC AGA GAC AAT TCC |
| VH2 mCDR3 linker Reverse (SEQ ID NO: 80) | CAT GGC GTA GCT GCC GCC GTA GTA GTA GTG TGT GGT ACA GTA ATA CAC GGC |
| VH2 mCDR3 linker Forward (SEQ ID NO: 81) | CAC TAC TAC TAC GGC GGC AGC TAC GCC ATG GAC TAC TGG GGC CAG GGA ACC CTG |
| VH5 mCDR1 linker Reverse (SEQ ID NO: 82) | GCT CAC GCC GTA GTC GGG CAG GCT CAC GCC AGA GGC TGC ACA GGA GAG TCT C' |

TABLE 5-continued

Sequences of primers used to construct selected human heavy chain 1st CDR - grafted variable regions.

| Primer | Sequence (5'→3') |
|---|---|
| VH5 mCDR1 linker Forward (SEQ ID NO: 83) | GGC GTG AGC CTG CCC GAC TAC GGC GTG AGC TGG ATC CGC CAG GCT CCA GGG |
| VH5 mCDR2 linker Forward (SEQ ID NO: 84) | GGC TCC GAG ACA ACC TAC TAC AAC AGC GCC CTG AAG AGC CGA TTC ACC ATC TCC AGG GAC AAC GCC |
| VH5 mCDR3 linker Reverse (SEQ ID NO: 85) | GTA GTC CAT GGC GTA GCT GCC GCC GTA GTA GTA GTG CCC CGC ACA GTA ATA AAC GGC |
| VH5 mCDR3 linker Forward (SEQ ID NO: 86) | CAC TAC TAC TAC GGC GGC AGC TAC GCC ATG GAC TAC TGG GGC CAG GGA ACC CTG GTC ACC |
| VH16 mCDR3 linker Reverse (SEQ ID NO: 87) | CAT GGC GTA GCT GCC GCC GTA GTA GTA GTG TCT CGC ACA GTA ATA CAC GGC |
| VH20 mCDR1 linker Reverse (SEQ ID NO: 88) | GCT CAC GCC GTA GTC GGG CAG GCT CAC GCC AGA GGC TAC ACA GGA GAG TCT C |
| VH20 mCDR2 linker Reverse (SEQ ID NO: 89) | GGC GCT GTT GTA GTA GGT TGT CTC GGA GCC CCA GAT CAC TGA AAC CCA CTC CAG CCC CTT C |
| VH20 mCDR2 linker Forward (SEQ ID NO: 90) | GGC TCC GAG ACA ACC TAC TAC AAC AGC GCC CTG AAG AGC CGA TTC ACC ATC TCC AGA GAC AAC GCC |
| VH20 mCDR3 linker Reverse (SEQ ID NO: 91) | CAT GGC GTA GCT GCC GCC GTA GTA GTA GTG TCT CGC ACA GTA ATA CAC AGC |
| SalI adaptor (SEQ ID NO: 92) | GATC GTCGAC GC TGA GGA GAC GGT GAC CAG GG |
| HindIII VJ2C Forward (SEQ ID NO: 93) | GATCAAGCTTGCCGCCACCATGGAGACAGACACACTC |

TABLE 6

Summary of templates and primers used to construct 1st CDR-grafted light chain variable regions.

| Construct | Template | Fragment 1 PCR primers | Fragment 2 PCR primers | Fragment 3 PCR primers | Fragment 4 PCR primers |
|---|---|---|---|---|---|
| VL39/FMC63 grafted (SEQ ID NO: 23) | pAE18 VL-2a clone#39 (SEQ ID NO: 7) | CMV-IE (SEQ ID NO: 74) and VL43 mCDR1 linker Reverse (SEQ ID NO: 101) | VL43 mCDR1 linker Forward (SEQ ID NO: 102) and VL43 mCDR2 linker Reverse (SEQ ID NO: 103) | VL39 mCDR2 linker Forward (SEQ ID NO: 94) and VL39 mCDR3 linker Reverse (SEQ ID NO: 95) | VL39 mCDR3 linker Forward (SEQ ID NO: 96) and NotI Kappa Reverse (SEQ ID NO: 112) |
| VL40/FMC63 grafted (SEQ ID NO: 24) | pAE18 VL-2a clone#40 (SEQ ID NO: 8) | CMV-IE (SEQ ID NO: 74) and VL43 mCDR1 linker Reverse (SEQ ID NO: 101) | VL43 mCDR1 linker Forward (SEQ ID NO: 102) and VL40 mCDR2 linker Reverse (SEQ ID NO: 97) | VL40 mCDR2 linker Forward (SEQ ID NO: 98) and VL40 mCDR3 linker Reverse (SEQ ID NO: 99) | VL40 mCDR3 linker Forward (SEQ ID NO: 100) and NotI Kappa Reverse (SEQ ID NO: 112) |
| VL43/FMC63 grafted (SEQ ID NO: 25) | pAE18 VL-2a clone#43 (SEQ ID NO: 9) | CMV-IE (SEQ ID NO: 74) and VL43 mCDR1 linker Reverse (SEQ ID NO: 101) | VL43 mCDR1 linker Forward (SEQ ID NO: 102) and VL43 mCDR2 linker Reverse (SEQ ID NO: 103) | VL43 mCDR2 linker Forward (SEQ ID NO: 104) and VL43 mCDR3 linker Reverse (SEQ ID NO: 105) | VL43 mCDR3 linker Forward (SEQ ID NO: 106) and NotI Kappa Reverse (SEQ ID NO: 112) |

TABLE 6-continued

Summary of templates and primers used to construct 1st CDR-grafted light chain variable regions.

| Construct | Template | Fragment 1 PCR primers | Fragment 2 PCR primers | Fragment 3 PCR primers | Fragment 4 PCR primers |
|---|---|---|---|---|---|
| VL44/FMC63 grafted (SEQ ID NO: 26) | pAE18 VL-2a clone#44 (SEQ ID NO: 10) | CMV-IE (SEQ ID NO: 74) and VL44 mCDR1 linker Reverse (SEQ ID NO: 107) | VL43 mCDR1 linker Forward (SEQ ID NO: 102) and VL44 mCDR2 linker Reverse (SEQ ID NO: 108) | VL44 mCDR2 linker Forward (SEQ ID NO: 109) and VL44 mCDR3 linker Reverse (SEQ ID NO: 110) | VL44 mCDR3 linker Forward (SEQ ID NO: 111) and NotI Kappa Reverse (SEQ ID NO: 112) |

TABLE 7

Sequences of primers used to construct selected human light chain 1st CDR - grafted variable regions.

| Primer | Sequence (5'→3') |
|---|---|
| VL39 mCDR2 linker Forward (SEQ ID NO: 94) | CAC ACC AGC CGG CTG CAC AGC GGG GTC CCA TCA AGG TTC AGC GGC |
| VL39 mCDR3 linker Reverse (SEQ ID NO: 95) | GGT GTA GGG CAG TGT GTT GCC TTG CTG GCA GTA ATA AGT TGC AAA ATC ATC |
| VL39 mCDR3 linker Forward (SEQ ID NO: 96) | CAG CAA GGC AAC ACA CTG CCC TAC ACC TTC GGC CAA GGG ACC AAG GTG G |
| VL40 mCDR2 linker Reverse (SEQ ID NO: 97) | GCT GTG CAG CCG GCT GGT GTG ATA GAT CAG GAG GTT AGG AAC |
| VL40 mCDR2 linker Forward (SEQ ID NO: 98) | CAC ACC AGC CGG CTG CAC AGC GGG GTC CCA TCT CGG TTC AGC GGC |
| VL40 mCDR3 linker Reverse (SEQ ID NO: 99) | GGT GTA GGG CAG TGT GTT GCC TTG CTG ACA GTA ATA AGT TGC AAA ATC TTC |
| VL40 mCDR3 linker Forward (SEQ ID NO: 100) | CAG CAA GGC AAC ACA CTG CCC TAC ACC TTC GGC GGA GGG ACC AAG GTG |
| VL43 mCDR1 linker Reverse (SEQ ID NO: 101) | GTT CAG GTA CTT GCT GAT GTC CTG GCT GGC CCG GCA AGT GAT GGT GAC TCT GTC TCC |
| VL43 mCDR1 linker Forward (SEQ ID NO: 102) | CGG GCC AGC CAG GAC ATC AGC AAG TAC CTG AAC TGG TAT CAG CAG AAA CCA GGG |
| VL43 mCDR2 linker Reverse (SEQ ID NO: 103) | GCT GTG CAG CCG GCT GGT GTG ATA GAT CAG GAG CTT AGG GGC |
| VL43 mCDR2 linker Forward (SEQ ID NO: 104) | CAC ACC AGC CGG CTG CAC AGC GGG GTC CCA TCA AGG TTC AGT GGC |
| VL43 mCDR3 linker Reverse (SEQ ID NO: 105) | GGT GTA GGG CAG TGT GTT GCC TTG CTG ACA GTA GTA AGT TGC AAA ATC TTC |
| VL43 mCDR3 linker Forward (SEQ ID NO: 106) | CAG CAA GGC AAC ACA CTG CCC TAC ACC TTC GGC CCT GGG ACC AAA GTG G |
| VL44 mCDR1 linker Reverse (SEQ ID NO: 107) | GTT CAG GTA CTT GCT GAT GTC CTG GCT GGC CCG ACA AGT GAT GGT GAC TCT GTC TCC |

TABLE 7-continued

Sequences of primers used to construct selected human light chain 1st CDR - grafted variable regions.

| Primer | Sequence (5'→3') |
|---|---|
| VL44 mCDR2 linker Reverse (SEQ ID NO: 108) | GCT GTG CAG CCG GCT GGT GTG ATA GAT CAG GAG GTT AGG GGC |
| VL44 mCDR2 linker Forward (SEQ ID NO: 109) | CAC ACC AGC CGG CTG CAC AGC GGG GTC CCA TCA AGG TTC AGC GGC |
| VL44 mCDR3 linker Reverse (SEQ ID NO: 110) | GGT GTA GGG CAG TGT GTT GCC TTG CTG ACA ATA ATA AGT TGC AAA ATC TTC |
| VL44 mCDR3 linker Forward (SEQ ID NO: 111) | CAG CAA GGC AAC ACA CTG CCC TAC ACC TTT GGC CAG GGG ACC AAG TTG G |
| NotI Kappa Reverse (SEQ ID NO: 112) | GATC GCGGCCGC TTA TCA ACA CTC TCC CCT GTT GAA GC |

Engineered heavy and light chains coding DNA sequences were ligated in independent vectors that are based on a modified pREP4 (Invitrogen, CA, USA) vector carrying CMV promoter and Bovine Growth Hormone poly-adenylation signal. Light chain specific vector allows expression of Kappa isotype light chains by ligating variable Kappa light chain cDNA fragments in front of Kappa light chain constant domain cDNA using BamHI and BsiWI restriction sites; while heavy chain specific vector was engineered to ligate variable heavy chain cDNA fragments in front of a cDNA encoding the γ1, hinge, γ2, and γ3 constant domains using BamHI and SalI restriction sites. In both heavy and light chain expression vectors, secretion was driven by the murine VJ2C leader peptide containing the BamHI site. Note that BsiWI site is located in the Kappa constant domain; while SalI site is situated in the Cγ1 domain.

For transient expression of immunoglobulin candidates, equal quantities of heavy and light chains vectors were co-transfected into suspension-adapted HEK-EBNA cells (ATCC-CRL-10852) using Polyethyleneimine (PEI). Typically, 100 ml of cells in suspension at a density of 0.8-1.2 million cells per ml is transfected with a DNA-PEI mixture containing 50 μg of expression vector encoding the heavy chain and 50 μg expression vector encoding the light chain. When recombinant expression vectors encoding antibody genes are introduced into the host cells, antibodies are produced by further culturing the cells for a period of 4 to 5 days to allow for secretion into the culture medium (EX-CELL 293, HEK293-serum-free medium, Sigma, Buchs, Switzerland), supplemented with 0.1% pluronic acid, 4 mM glutamine, and 0.25 μg/ml geneticin). Antibodies were then purified from cell-free supernatant using recombinant protein-A streamline media (GE, Switzerland), and buffered exchanged into phosphate buffer saline prior to assays.

Humanization strategy was based on the initial four grafted heavy and light chains (above), which were combined in a pair-wise fashion to derive 16 initial full-length immunoglobulin candidates. These immunoglobulins were assessed for antigen-binding affinity by half-maximal binding assays on B-cell lymphoma cell-lines (FACS) and compared to a chimeric version of FMC63 (this was to standardized level of staining from the anti-human Fc PE-labeled detection-antibody, as described in Example 2). From this initial work, immunoglobulin candidates that contained VH16 (SEQ ID NO: 21) or VH20 (SEQ ID NO: 22) showed best binding to Raji cells in FACS experiments, as seen in FIGS. 1A and 1B. The antibody consisting of VH16 heavy chain paired to light VL43 had superior level of expression in transient transfections as well as superior melting temperature of its FAB fragment and consequently was selected for further back-mutations and rational engineering as shown in Table 8.

TABLE 8

IgG transient expression level and FAB stability of the 1st CDR-grafted antibodies.

| Antibody | Expression (mg/L) | Tm Fab (° C.) |
|---|---|---|
| Chimeric FMC63 | 48 | 84.27 |
| VH2/VL39 | 11 | 78.78 |
| VH2/VL40 | 23 | 76.55 |
| VH2/VL43 | 13 | 73.17 |
| VH2/VL44 | 21 | 78.27 |
| VH5/VL39 | 5 | 76.08 |
| VH5/VL40 | 9 | ND |
| VH5/VL43 | 19 | 76.76 |
| VH5/VL44 | 12 | 74.81 |
| VH16/VL39 | 8 | 71.67 |
| VH16/VL40 | 11 | 71.81 |
| VH16/VL43 | 20 | 83.54 |
| VH16/VL44 | 7 | 85.16 |
| VH20/VL39 | 11 | 82.41 |
| VH20/VL40 | 24 | 79.46 |
| VH20/VL43 | 37 | 79.67 |
| VH20/VL44 | 26 | 82.00 |

Back Mutations of the Human Frameworks

Since straight grafting of CDRs from FMC63 mouse antibody led to human acceptors with low binding properties, it was desirable to mutate certain residues in the frameworks back to murine residues at some positions. This process called back-mutation is the most unpredictable procedure in the humanization of monoclonal antibodies, and necessitate the identification of critical framework residues from the parent antibody that need to be retained in order to substantially retain the binding properties of the parent antibody while at the same time minimizing the potential immunogenicity of the resultant antibody. Tables 9 and 10 and FIGS. 2A and 2B show residues (Kabat numbering) that may affect the conformations of CDRs and which were selected as potential candidates for back mutations to murine residues.

TABLE 9

Comparison of FMC63 and human acceptor light chain frameworks. VH

| Kabat position | FMC63 | VH16 | VH20 |
|---|---|---|---|
| 37 | I | V | V |
| 42 | R | G | G |
| 48 | L | V | V |
| 49 | G | A | S |
| 67 | L | F | F |
| 71 | K | R | R |
| 78 | V | L | L |
| 94 | K | R | R |

TABLE 10

Comparison of FMC63 and human acceptor heavy chain frameworks. VL

| Kabat position | FMC63 | VL39, VL40, VL43, VL44 |
|---|---|---|
| 44 | V | P, P, P, P |
| 71 | Y | F, F, F, F |
| 87 | F | Y, Y, Y, Y |

Among the eight possible back mutations for the heavy chain, changes at position 37, 48, and 49 were discarded because of their conservative nature. Hence four reshaped versions of VH16 were made, and combined in a pair-wise fashion with all three back mutants of VL 43. In addition reshaped variants were paired to parental VH16 and VL43 to investigate the impact of each individual back mutation. A total of 24 full-length immunoglobulin candidates were investigated. The five heavy chain variants had the following single point mutation compared to VH16 sequence: G42R, F67L, R71K, L78V, and R94K; while, the three light chain variants had P44V, F71Y, and Y87F, compared to VL43.

From FACS experiments (as described in example 2), transient expression levels and FAB stability measurements it was found that back-mutations heavy chain R94K and/or light chain P44V dramatically increase binding to Raji cells or NALM-6 cells while improving expression level and maintaining good FAB stability as shown in Table 11, and 12. These two positions alone restored about half of the binding of parental FMC63 antibody.

TABLE 11

FACS staining of humanized back-mutated anti-CD19 antibodies on Raji and NALM-6 tumour cell-lines.

| | VL43 | | VL43-P44V | | VL43-F71Y | | VL43-Y87F | |
|---|---|---|---|---|---|---|---|---|
| | Raji | NALM-6 | Raji | NALM-6 | Raji | NALM-6 | Raji | NALM-6 |
| VH16 | 7.42 | 3.29 | 9.72 | 6.05 | 11.29 | NA | 10 | NA |
| VH16-G42R | NA | 3.48 | 8.33 | NA | NA | 3.97 | 8.43 | 3.65 |
| VH16-F67L | NA | 2.40 | NA | 2.37 | 6.54 | NA | 4.35 | NA |
| VH16-R71K | 4.43 | NA | 6.93 | NA | NA | 2.67 | 4.19 | NA |
| VH16-L78V | 10.77 | NA | 25.93 | 10.95 | 12.28 | NA | 17.95 | NA |
| VH16-R94K | 27.06 | 14.38 | 52.87 | 32.86 | 41.82 | 23.47 | 31.82 | NA |

Values (indicated as Raji, and NALM-6 for measurements on Raji and NALM-6 cells, respectively) correspond to antibodies mid-point fluorescence (MPF) measure by flow-cytometry expressed as percentage to that observed for the FMC63 chimeric antibody.

TABLE 12

IgG transient expression level and FAB stability of the humanized back-mutated anti-CD19 antibodies.

| | VL43 | | VL43-P44V | | VL43-F71Y | | VL43-Y87F | |
|---|---|---|---|---|---|---|---|---|
| | FAB Tm (° C.) | Transient exp. level (mg/l) | FAB Tm (° C.) | Transient exp. level (mg/l) | FAB Tm (° C.) | Transient exp. level (mg/l) | FAB Tm (° C.) | Transient exp. level (mg/l) |
| VH16 | 83.54 | 20 | 81.04 | 29 | 83.9 | 25 | 82.97 | 24 |
| VH16-G42R | 82.59 | 48 | 79.84 | 20 | 83.08 | 48 | 82.51 | 34 |
| VH16-F67L | 82.92 | 46 | 79.92 | 23 | 83.34 | 29 | 82.22 | 22 |
| VH16-R71K | 83.92 | 45 | 80.9 | 52 | 83.67 | 48 | 83.34 | 39 |
| VH16-L78V | 87.87 | 36 | 85.87 | 42 | 87.87 | 44 | 86.68 | 42 |
| VH16-R94K | 82.75 | 63 | 80.10 | 42 | 82.88 | 50 | 82.22 | 38 |

Germlining

Germline frameworks are typically better than individual mature antibody framework as acceptor frameworks for humanized antibodies because their lack of somatic mutations may lower the degree of immunogenicity. VH16 is derived from healthy donor B-cell mRNA using degenerate primers designed according to germline sequences from VBASE2, and this procedure provides antibodies that have not yet encountered any antigens. However, since the frequency of truly naïve antibodies depend heavily on the source of B cells, mutations can also be observed with the above procedure (Klein U. et al, 1997, Blood 89, p 1288-1298). Both VH16 and VL 43 had a low contain of non-germline residues that were mutated back to germline, these changes were VH16-Q6E, VL43-V3Q, and VL43-T7S as shown in Table 13.

TABLE 13

FACS staining of humanized back-mutated/germlined anti-CD19 antibodies on Raji tumour cell-lines.

|  | VL43 | | | VL43-V3Q/T7S | | |
| --- | --- | --- | --- | --- | --- | --- |
|  | Raji | Transient exp. level (mg/L) | FAB Tm (° C.) | Raji | Transient exp. level (mg/L) | FAB Tm (° C.) |
| VH16 | 7.14 | 20 | 83.54 | 4.93 | 28 | 83.51 |
| VH16-R94K | 26.79 | 60 | 82.75 | 27.78 | 13.5 | 82.36 |
| VH16-Q6E | ND | 30 | 83.12 | 5.68 | 36 | 83.46 |

Values (indicated as Raji) correspond to antibodies mid-point fluorescence (MPF) measure by flow-cytometry expressed as percentage to that observed for the FMC63 chimeric antibody. IgG transient expression level and FAB stability of the humanized back-mutated/germlined anti-CD19 antibodies are also indicated.

All germline changes were found to have no impact on VH16-VL43 antibody, whether on its affinity nor on its FAB stability and only transient level of expression was significantly increased. Subsequently, VH16-VL43 variants with germline residues at position VL43-V3Q, and VL43-T7S were used for affinity improvement through rational design (below).

Affinity Improvement of Back Mutated Human Acceptors by Rational Design and CDR Engineering Tyrosine mutants. FMC63 CDRs have high tyrosine content: heavy chain CDR1 (position 32), heavy chain CDR2 (positions 58, and 59), heavy chain CDR3 (positions 96, 97, 98, and 100b), light chain CDR1 (position 32), and light chain CDR3 (position 96). Of particular are the four tyrosine residues in heavy chain CDR3 (Y96, Y97, Y98, and Y100b), and the two other tyrosine residues found in heavy chain CDR1 and light chain CDR1, both at position 32. These residues, may define the putative interaction binding site for human CD19 molecule, since in addition to their hydrophobic nature and the fact that most of them are part of heavy chain CDR3, usually the most important CDR as it often determine specificity, they also notably protrude outside of the antibody binding-site plan in VH16-R94K/VL43 3D-model. Taken together these observations allow the identification of heavy chain CDR3 residues 96, 97, 98, 100b and light chain CDR1 residue 32 as candidates for rational affinity improvement. Tyrosine residues are unique because they have a dual hydrophobic and polar nature by virtue of their aromatic ring and hydroxyl group respectively. Hence, the above residues were mutated for phenylalanine to increase hydrophobicity and probe the importance of a polar versus hydrophobic content at these positions. Phenylalanine mutants measurements in the context of the heavy chain R94K mutations show that heavy chain mutant 32, 97, 98 as well as light chain mutant 32 are superior to parental molecule VH16-R94K/VL43, with heavy chain mutant Y97F having 72.8% of chimeric FMC63 affinity as shown in Table 14.

TABLE 14

FACS staining of humanized back-mutated/affinity matured anti-CD19 antibodies on Raji tumour cell-lines.

| Antibody | Relative Raji FACS staining | Transient exp. (mg/L) | FAB Tm (° C.) |
| --- | --- | --- | --- |
| VH16 R94K Y32F VL43 | 62.5 | 17 | 82.51 |
| VH16 R94K Y96F VL43 | 5.36 | 14 | 83.53 |
| VH16 R94K Y97F VL43 | 72.82 | 17 | 81.53 |
| VH16 R94K Y98F VL43 | 34.09 | 10 | 81.91 |
| VH16 R94K Y100bF VL43 | 27.78 | 24 | 82.92 |
| VH16 R94K VL43 Y32F | 39.47 | 25 | 82.56 |

Values (indicated as Raji) correspond to antibodies mid-point fluorescence (MPF) measure by flow-cytometry expressed as percentage to that observed for the FMC63 chimeric antibody. IgG transient expression level and FAB stability of the humanized back-mutated/affinity matured anti-CD19 antibodies are also indicated.

Light Chain-Pro 44 Mutants.

Light chain P44 is located at the bottom of the interface between heavy and light chain, a location that could explain the great affinity improvement when back mutated to valine. Two other hydrophobic amino-acids were investigated at position 44 to possibly tune (or better adjust) the interface between light and heavy chain: isoleucine and leucine variants were constructed in the context of the VH16-R94K variants as shown in Table 15. Affinity and stability measurements revealed that isoleucine was superior to the valine back-mutation at position 44, while change for a leucine only provided a mild improvement despite being a more logical choice.

TABLE 15

FACS staining of humanized back-mutated/affinity matured anti-CD19 antibodies on Raji tumour cell-lines.

| Antibody | Relative Raji FACS staining | Transient exp. (mg/L) | FAB Tm (° C.) |
| --- | --- | --- | --- |
| VH16 R94K VL43 P44I | 69.44 | 17 | 81.37 |
| VH16 R94K VL43 P44L | 37.50 | 18 | 80.10 |

Values (indicated as Raji) correspond to antibodies mid-point fluorescence (MPF) measure by flow-cytometry expressed as percentage to that observed for the FMC63 chimeric antibody. IgG transient expression level and FAB stability of the humanized back-mutated/affinity matured anti-CD19 antibodies are also indicated.

Removal of a Potential Deamidation Site.

Deamidation is a major route of antibody degradation. Deamidation of Asn to Asp is highly sequence-dependent and occurs in regions of the protein which are known or predicted to be flexible as in CDR regions (Bischoff and Kolbe (Journal of Chromatography B, 662 (1994), 261-278); this usually involves Asn residues located in CDRs. A high probability for deamidation of its asparagine was identified in CDR3 of the FMC63 light chain at position 91 to 93 (GNT). Hence to prevent putative deamidation, the following changes were investigated in the context of the VH16-R94K heavy chain: VL43-N92A, VL43-T93V and VL-43-T93A as shown in Table 16. It was found that both N92A and T93A maintain binding affinity. N92A variant was also found to have improved FAB stability.

TABLE 16

FACS staining of humanized back-mutated/deamidation site removed anti-CD19 antibodies on Raji tumour cell-lines.

| Antibody | Relative Raji FACS staining | Transient exp. (mg/L) | FAB Tm (° C.) |
|---|---|---|---|
| VH16 VL43 | 7.14 | 20 | 83.54 |
| VH16 R94K VL43 | 26.79 | 60 | 82.36 |
| VH16 R94K VL43 N92A | 25.86 | 33 | 84.09 |
| VK16 R94K VL43 T93V | 17.44 | 34 | 82.43 |
| VH16 R94K VL43 T93A | 34.09 | 35 | 82.81 |

Values (indicated as Raji) correspond to antibodies mid-point fluorescence (MPF) measure by correspond to antibodies mid-point fluorescence (MPF) measure by flow-cytometry expressed as percentage to that observed for the FMC63 chimeric antibody. IgG transient expression level and FAB stability of the humanized back-mutated/deamidation-site-removed anti-CD19 antibodies are also indicated.

Other improvements of VL43 human acceptor have been carried out at position F71. Binding activity to Raji of VH16 R94K VL43 F71H (SEQ ID NO: 61), VH16 R94K VL43 F71S (SEQ ID NO: 62), and VH16 R94K VL43 F71T (SEQ ID NO: 63) was similar to binding activity of VH16 R94K VL43.

Combining Back-Mutations and Rationally-Designed Mutations

To further increase binding to Raji cells, back mutations and rationally design mutations were combined in a systematic approach in which a limited number of combination were tested. Most improved mutations identified from tyrosine switch to phenylalanine in heavy and light chains (above) were combined with light chain changes P44I, and N92A, as well as germline changes V3Q, and T7S.

Although CDR changes have often an additive effect in terms of affinity, when these CDR changes are combined with mutations that affect framework, the outcome is not predictable. Table 17 shows the relative FACS staining for VH16/VL43 variants combining germline, framework, back and CDR mutations. It was found that combining heavy chain CDR changes Y32F, and Y97F with back mutations R94K result in loss of binding, whereas Y32F combined with heavy chain back mutation R94K and light chain change P44I and N92A greatly improved binding, which by our mean of measurements resulted in a relative mid-titration of staining superior to FMC63 chimera. Another favorable combination is both heavy chain CDR mutation Y100BF and Y32F in the context of heavy chain back mutation R94K, and light chain changes V3Q, T7S, Y32F, P44I and N92A.

TABLE 17

FACS staining of humanized back-mutated/germlined/affinity matured/deamidation-site-removed anti-CD19 antibodies on Raji tumour cell-lines.

| | VL43 | | | |
|---|---|---|---|---|
| VH16 | V3Q/T7S/ N92A | V3Q/T7S/ Y32F/N92A | V3Q/T7S/ P44I/N92A | V3Q/T7S/ Y32F/P44I/N92A |
| R94K | 18.18 | Low Saturation | 83.33 | 111.11 |
| Y32F/R94K | 58.82 | Low Saturation | 133.33 | Low Saturation |
| R94K/Y97F | Low Saturation | No Binding | NA | Low Saturation |
| R94K/Y100$_B$F | NA | NA | 101.01 | 144.93 |
| Y32F/R94K/Y97F | 16.95 | No Binding | Low Saturation | 6.67 |

Values (indicated as Raji) correspond to antibodies mid-point fluorescence (MPF) measure by flow-cytometry expressed as percentage to that observed for the FMC63 chimeric antibody.

Combinations which display high binding activity also retain high transient expression level (Table 18) as well as high FAB fragment thermostability (Table 19).

TABLE 18

IgG transient expression level of the humanized back-mutated/germlined/ affinity matured/deamidation-site-removed anti-CD19 antibodies.

| | VL43 | | | |
|---|---|---|---|---|
| VH16 | V3Q/T7S/ N92A | V3Q/T7S/ Y32F/N92A | V3Q/T7S/ P44I/ N92A | V3Q/T7S/ Y32F/P44I/ N92A |
| R94K | 15 | 45 | 47 | 34 |
| Y32F/R94K | 6.5 | 25 | 26 | 18 |
| R94K/Y97F | 23 | 31 | 25 | 22 |
| R94K/Y100$_B$F | NA | NA | NA | 32 |
| Y32F/R94K/Y97F | 20 | 32 | 26 | 24 |

TABLE 19

FAB stability (° C.) of the humanized back-mutated/germlined/ affinity matured/deamidation-site-removed anti-CD19 antibodies.

| | VL43 | | | |
|---|---|---|---|---|
| VH16 | V3Q/T7S/ N92A | V3Q/T7S/ Y32F/N92A | V3Q/T7S/ P44I/ N92A | V3Q/T7S/ Y32F/P44I/ N92A |
| R94K | 84.29 | 84.34 | 83.13 | 83.31 |
| Y32F/R94K | 84.45 | 84.31 | 83.21 | 83.39 |
| R94K/Y97F | 83.92 | 83.96 | 82.9 | 83.04 |
| R94K/Y100$_B$F | NA | NA | NA | 83.42 |
| Y32F/R94K/Y97F | 83.93 | 83.96 | 82.77 | 83.01 |

Example 2

Binding of the CD19 Antibodies to B Cell-Derived Tumor Cell Lines: Flow Cytometry Analysis Binding of the CD19 humanized monoclonal antibodies by flow cytometry to Raji tumor cells (human Burkitt lymphoma, DSMZ ACC319), NALM-6 (human B cell precursor leukemia, DSMZ ACC128) and SU-DHL-6 (human B cell lymphoma, DSMZ ACC572) (all cell lines from DSMZ Braunschweig, Deutschland) was assessed. Cells were incubated with serial dilutions of each humanized monoclonal antibody. An irrelevant human IgG1 was used as a negative control. The cells were washed and detected by a phycoerythrin-labeled (PE) anti-human secondary antibody (eBioscience, CA, USA) and analyzed by flow cytometry. To ensure comparable levels of staining between humanized candidates and parental murine antibody, a chimeric FMC63, i.e. an antibody which consists of the FMC63 murine heavy variable domain fused to human IgG1 heavy constant domains as shown in SEQ ID NO: 68 and the murine light variable domain fused to kappa constant domain as shown in SEQ ID NO: 69, was used as standard. Results for binding to Raji or NALM-6 are shown in Table 11, 13-17, and binding to the SU-DHL-6 cell line are shown in FIG. 3. All results in FIG. 3 were measures of the mean fluorescent intensity (MFI) of cell staining. From MFI versus antibody concentration curves, Mid-Point Fluorescence (MPF) value for each anti-CD19 humanized antibody was calculated using the software GraphPad Prism 5 (CA, USA). MPF of a dose response curve represents the concentration of antibody (µg/ml) where 50% of its maximal staining is observed. Thus, antibodies with better binding activity on cells have lower MPF (µg/ml). In Tables 11, 13-17, values represent relative MPF between the chimeric FMC63 and anti-CD19 humanized variants, and were calculated as follow: [1/(MPF chimeric FMC63/MPF anti-CD19 humanized antibody)]×100. Higher is the percentage; better is the binding activity of the antibody.

FIG. 3 shows the dramatic improvement in affinity for SU-DHL-6 cells along the different humanization steps from VH16/VL43 antibody to VH16-R94K-Y100BF/VL43-V3Q-T7S-P44I-N92A antibody. The latter reaches strong affinity to B cells similar to the FMC63 chimera. The affinity improvements of the FMC63 humanized antibodies to cells are a direct result of mutations that substantially retain and/or improve the binding properties of human CDR-grafted acceptor frameworks as described above.

Example 3

Scatchard Binding Analysis of the Anti-CD19 Human Antibodies to Raji Tumor Cells Scatchard Binding Analysis of Humanized Antibodies to Raji-B Tumor Cells The constant binding affinity of an antibody to its target can be determined with a saturation binding curve. At equilibrium, the amounts of bound and free antibody to its binding site are indicative of the dissociation binding constant Kd. Usually, for one single binding site, the ratio bound/free versus bound antibody has a linear correlation, where the slope corresponds to the inverse of the binding constant Kd.

Tested antibodies were labelled with the fluorescent dye europium ($Eu^{3+}$) (PerkinElmer, MA, USA). $Eu^{3+}$ offers the possibility to quantify the amount of bound antibody molecules to cells as well as free antibody molecules. Saturation of binding to Raji cells by selected humanized candidates was followed via $Eu^{3+}$ using time resolved fluorescence. To demonstrate the binding specificity of $Eu^{3+}$-labelled candidates without unspecific behaviour of the $Eu^{3+}$ dye to the cell surface, a negative isotype human IgG1 was also labelled with $Eu^{3+}$.

Raji cells as described in Example 2 were grown in RPMI-1640 medium (Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland). The cells were washed with the same culture medium and adjusted to a final concentration of $1\times10^6$ cells/ml. A 100 µl volume of Raji cells was seeded in U-bottomed 96-well plate. Serial dilutions of $Eu^{3+}$-labelled antibodies were prepared into PBS-2.5% FBS-0.05% sodium azide (NaN3) into a separate 96 well plate and cooled down to 4° C. A 100 µl volume of each $Eu^{3+}$-labelled antibody dilution was then transferred on the Raji cells, corresponding to a final dilution range for the $Eu^{3+}$-labelled antibodies of 13.3 nM to 6.5 pM. Cells were incubated with $Eu^{3+}$-antibody for 15 minutes on ice to reach equilibrium. The amount of free $Eu^{3+}$-labelled antibodies were measured by transferring aliquots of cell-free supernatant (volumes were empirically adjusted depending on antibody concentration; cells were spun at 1300 RPM for 2 min) into a fresh plate containing 100 µl of Delfia solution (PerkinElmer, MA, USA; an enhancer of $Eu^{3+}$ fluorescence). To ensure complete removal of the supernatant, cells were spin down once more at 1300 RPM for 2 minutes. After the second centrifugation, the supernatant was discarded, and cells were washed twice with 200 µl of cold binding buffer (PBS-2.5% FBS-0.05% $NaN_3$). Cell pellets were resuspended into 100 µl of Delfia solution. Time resolved fluorescence was measured for both plates (free or bound $Eu^{3+}$-antibody) with a spectrophotometer (Bio-Tek, synergy2, VT, USA; excitation wavelength was 340 nm, emission wavelength was 615 nm, with time delay of 400 µs and an acquisition time of 1000 µs). The dissociation constant Kd was determined by Scatchard analysis, where the slope of the linear representation of bound versus bound/free represent 1/Kd. Kd were determined in duplicate for each antibody and each fluorescence measurements were performed in triplicate. In accordance with the binding assay above, FIGS. 4A and 4B show striking Kd improvement along the different mutation stages from antibody VH16-R94K/VL43 (Kd=47 nM) to antibody VH16-R94K-Y100BF/VL43-V3Q-T7S-P44I-N92A (Kd=10.9 nM). The latter antibody has improved Kd to the parental chimeric FMC63 (11.8 nM).

Binding Competition Between the Europium-Labelled FMC63 Chimera and Unlabelled Anti-CD19 Humanized Antibodies or Ki Determination Another way to evaluate the binding affinity of each humanized antibodies is to measure binding competition against the parental chimeric FMC63 antibody on Raji cells. To inhibit the binding of europium-labelled chimeric FMC63 ($Eu^{3+}$-FMC63) to the CD19 antigen expressed on Raji cells, increasing concentrations of unlabelled antibody were added together with a constant amount of $Eu^{3+}$-FMC63. To that aim, 100 µl volumes of Raji cells in RPMI-1640 medium (Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland), prepared at concentration of $1\times10^6$ cells/ml were seeded in a U-bottomed 96-well plate. Serial dilutions of the competitor antibodies were prepared into a separate 96-well plate into PBS-2.5% FBS-0.05% $NaN_3$ and subsequently mixed with a constant amount of $Eu^{3+}$-FMC63. The antibody dilutions were cooled down to 4° C. before 100 µl was taken and added on the Raji cells. Final dilutions of unlabelled humanized antibodies ranged from 100 nM up to 4.2 pM, while the concentration of $Eu^{3+}$-FMC63 was maintained at 0.2 nM. Cells were incubated with the antibodies for 15 minutes on ice. After reaching equilibrium, the cells were centrifuged at 1300 RPM for 2 minutes and supernatant was discarded. Cell pellets were washed twice with 200 µl of cold binding buffer PBS-2.5% FBS-0.05% $NaN_3$, and resuspended into 100 µl of Delfia solution. Cell bound $Eu^{3+}$-FMC63 was measured with time resolved fluorescence as described above. The amount of $Eu^{3+}$-FMC63 (fmole) per well was determined and plotted versus the total amount of unlabelled antibody. The inhibition binding curve of $Eu^{3+}$-FMC63 was further analysed with the GraphPad Prism 5 software (CA, USA) using one-site competition model, and total ligand fix concentration of 0.2 nM; inhibition binding constants were in the nanomolar range. As shown in Table 20 and according to experiments presented above, the framework VH16VL43 which does not include mutations, displays little affinity for Raji cells (72.8 nM) while humanized variant VH16-R94K-Y100BF/VL43-V3Q-T7S-P44I-N92A exhibits a very high affinity, equivalent to FMC63 chimera (1.9 nM versus 1.4 nM). Results with standard deviation have been determined at least 3 times.

TABLE 20

Ki determination of humanized anti-CD19 antibodies.

| Antibody | Ki (nM) |
|---|---|
| FMC63 Chimera | 1.4 ± 0.32 |
| Isotype control IgG1 | No Competition |
| VH16/VL43 | 72.8 |
| VH16-R94K/VL43 | 7.6 |
| VH16-R94K/VL43-V3Q-T7S-P44I-N92A | 3.9 ± 1.02 |
| VH16-R94K-Y100$_B$F/VL43-V3Q-T7S-Y32F-P44I-N92A | 2.1 ± 0.5 |
| VH16-R94K-Y100$_B$F/VL43-V3Q-T7S-P44I-N92A | 1.9 |
| VH16-Y32F-R94K-Y97F/VL43-V3Q-T7S-N92A | 49.9 |

Example 4

Assessment of Antibody-Dependent Cellular Cytotoxicity (ADCC) Activity

ADCC activities of humanized anti-CD19 antibodies were measured by lactate deshydrogenase (LDH)-releasing assay using the CytoTox 96 Non-Radoactive Cytotoxicity Assay kit (Promega, Madison, USA). Human peripheral blood mononuclear cells (PBMC) were purified from citrated whole blood by standard Ficoll-paque separation, resuspended in complete medium (RPMI-1640 medium (Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland)), and 100 U/ml of human IL-2 (Sigma, Mo., USA)) and incubated overnight at 37° C. The following day, PBMC were collected by centrifugation, washed twice and resuspended in culture medium at a density of $8 \times 10^6$ cells/ml. The CD19$^+$ cell line Raji as described in Example 2 was used as target cells. Raji cells were washed twice and resuspended in complete medium at a density of $0.2 \times 10^6$ cells/ml. Fifty microliters of antibody diluted at 1.5 μg/ml (final concentration was 0.5 μg/ml) were mixed with 50 μl of target cells, and added to an equivalent volume of PBMC into a U-bottomed 96-well plate. A target to effector ratio of 1:40 was used throughout the experiments. After 4 hours incubation at 37° C., cells were centrifuged and 50 μl samples of cell-free supernatant were collected, transferred to a flat-bottomed 96-well plate, and assayed. Percentage of lysis was calculated as follows: (Sample release−Target spontaneous release−Effector spontaneous release)/(Maximum release−Target spontaneous release)*100; where Target spontaneous release is the fluorescence from wells which only contained target cells, Effector spontaneous release is the fluorescence from wells which only contained effector cells, and Maximum release is the fluorescence from wells containing target cells which have been treated with lysis buffer. Background percentage of lysis obtained in absence of antibody (Target+Effector cells) was subtracted from percentage of lysis of sample.

Figure 5:
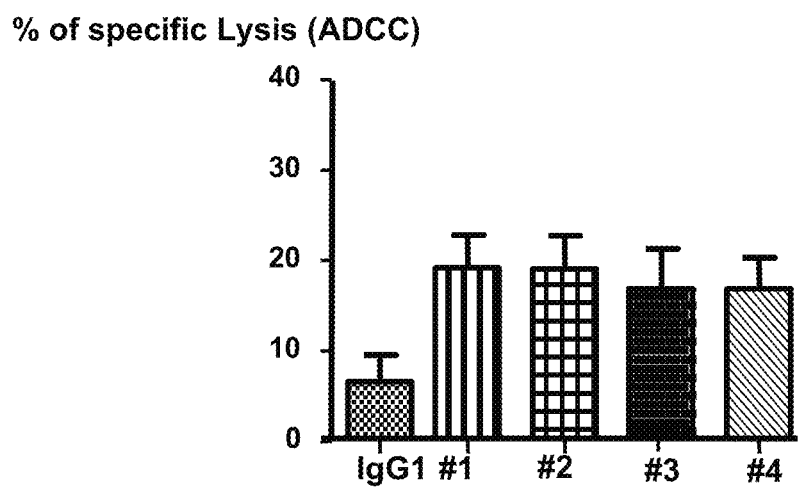
FIGS. 5A and 5B show ADCC activity of humanized anti-CD19 antibodies on Raji tumor cells.
Figure 5:
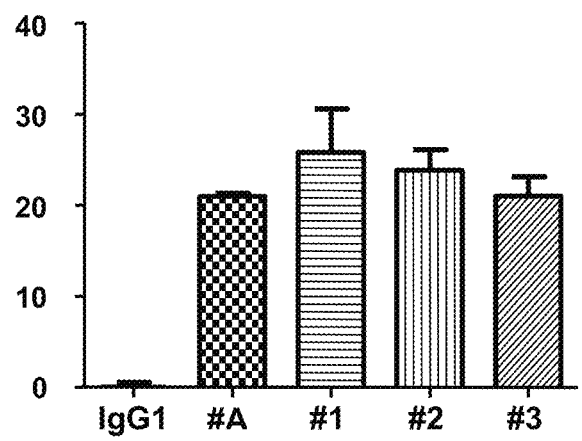

FIG. 5A and FIG. 5B show little specific Raji lysis due to IgG1 control. However, humanized antibody-induced lysis was increased at least three fold for the VH16-R94K-Y100BF/VL43-V3Q-T7S-Y32F-P44I-N92A antibody or VH16-R94K/VL43-V3Q-T7S-P44I-N92A antibody or VH16-R94K-Y100BF/VL43-V3Q-T7S-P44I-N92A or chimeric FMC63 (FIG. 5A shows average of 3 different donors±standard deviation, FIG. 5B shows results from 1 donor performed in triplicate±standard deviation). This data demonstrates that selected humanized anti-CD19 antibodies lead to cellular cytotoxicity of CD19$^+$ expressing cells that is similar to the parental chimeric FMC63.

Example 5

Apoptosis Induction by the Anti-CD19 Antibodies

To measure antibody-induced cell death, Raji cells as described in Example 2 were prepared at $1 \times 10^6$ cells/ml in RPMI-1640 medium ((Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland)), and 100 μl per well in a 96-well plate or 1 ml in a 24-well plate were seeded. Cells were incubated at 37° C., 5% $CO_2$ for 15 min to 24 h with antibody concentration ranging from 0.0016 to 1 μg/ml (0.01 μM to 6.6 μM). After incubation, cells were centrifuged in a U-bottom plate at 1300 RPM for 3 min and washed with 200 μl of PBS. One hundred μl of 1× binding buffer (BD Pharmingen, Allschwil, Switzerland) was added in each well, followed by 2.5 μl of annexin V-FITC and 2.5 μl propidium iodine (PI, BD Pharmingen, Allschwil, Switzerland). Cells were incubated with annexin-V and PI at room temperature before flow cytometry analysis. Double staining with annexin-V and PI characterized the dead-cell population while living cells are stained neither by annexin-V nor PI.

Figure 6:
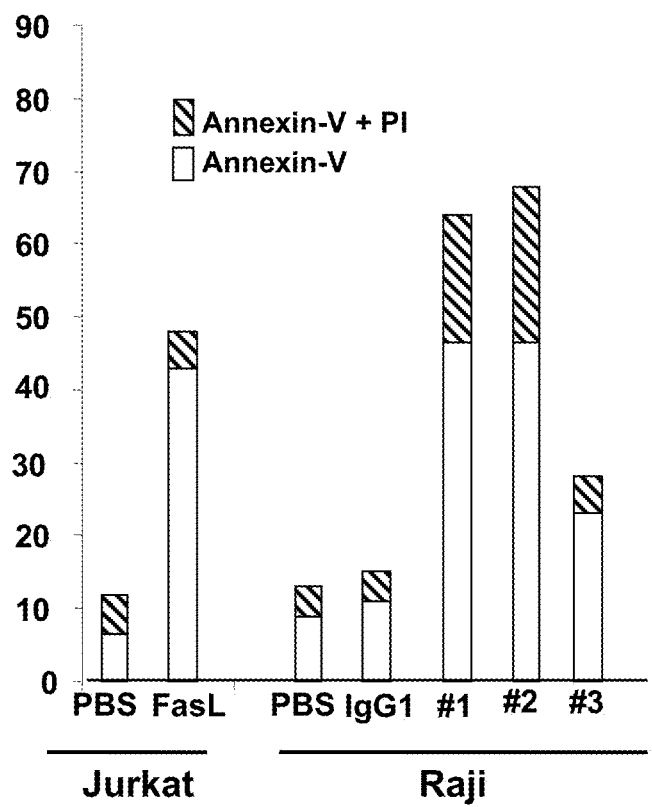
FIG. 6 shows induction of apoptosis by humanized anti-CD19 antibodies on Raji tumor cells.

FIG. 6 shows Annexin-V and PI staining of Raji cells incubated with 1 μg/ml antibody for 2.5 h. Surprisingly enough, while VH16-R94K-Y100BF/VL43-V3Q-T7S-P44I-N92A and VH16-R94K/VL43-V3Q-T7S-P44I-N92A humanized anti-CD19 antibodies induced strong annexin-V staining and cell death, the parental chimeric FMC63 had no effect on apoptosis. On note, the slight increase of annexin-V staining after chimeric FMC63 treatment observed on FIG. 6 was not reproducible and not significant. Strikingly, cells stained with annexin-V as early as 15 min after addition of humanized anti-CD19 antibodies, and both staining (Annexin-V plus PI) reached a plateau after 4 h incubation with humanized anti-CD19 antibodies (not shown). The apoptotic mechanism due to anti-CD19 antibodies is different from anti-FasL-induced apoptosis on Raji cells. Indeed, FasL did not induce Annexin-V staining on Raji cells (not shown). This result proves that humanization gave new characteristics to the anti-CD19 antibody. The new apoptotic characteristic given to humanized anti-CD19 antibodies in addition to their ability to trigger homotypic cell adhesion (not shown) compared to the parental chimeric FMC63 was unexpected and of extreme importance with regard to studies on anti-CD20 antibodies. Indeed, Beers et al. have shown that anti-CD20 antibodies with strong apoptotic and homotypic adhesion properties had better B cell depletion ability in animal (Beers S. A. et al, 2008, Blood 112, p 4170-4177). In addition, Raji cells stained with annexin-V as early as 15 min after adding anti- CD19 antibodies. The staining reached a plateau after 4 h incubation. This fast apoptotic event is superior to anti-CD20 antibodies, which apoptotic effects are generally observed after 24 h (Chan H. T. C. et al., Cancer Research, 63:5480-5489).

Example 6

Inhibition of Proliferation of Malignant B Cells in Vitro

Proliferation—alamarBlue

Figure 7:
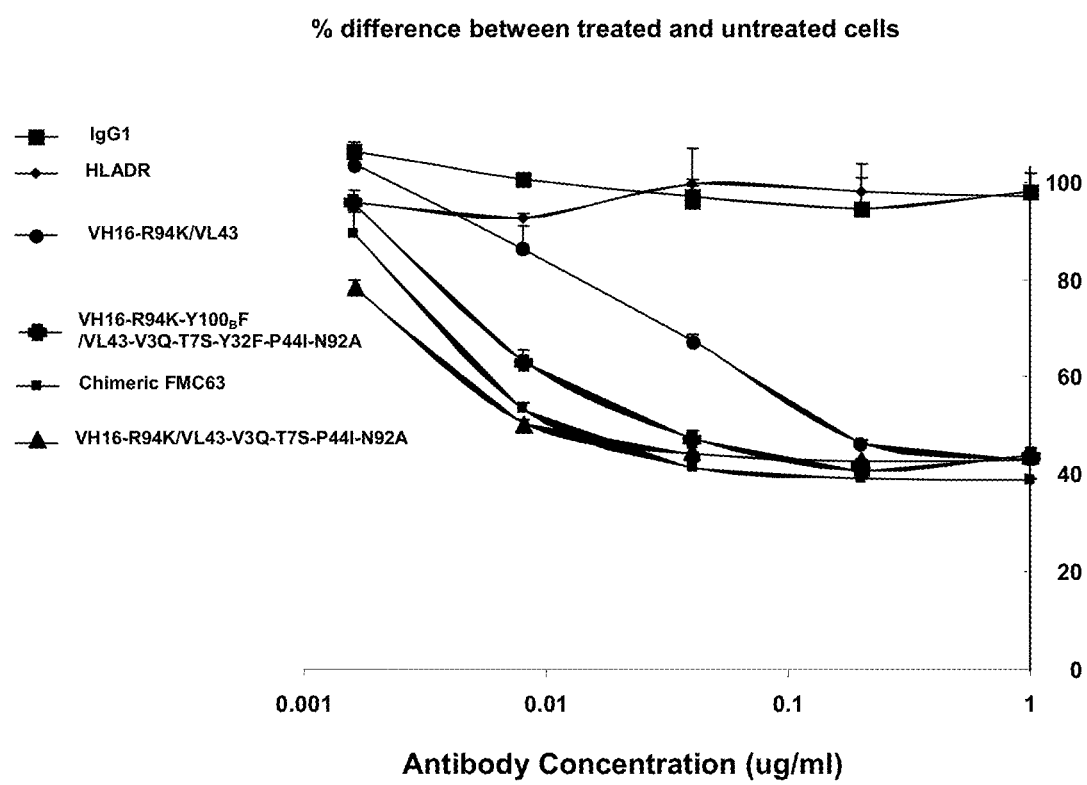
FIG. 7A shows inhibition of SU-DHL-6 human B cell lymphoma cell proliferation by humanized anti-CD19 antibodies.
FIG. 7B shows clonogenicicity of Raji tumor cells after treatment with humanized anti-CD19 antibodies.
Figure 7:
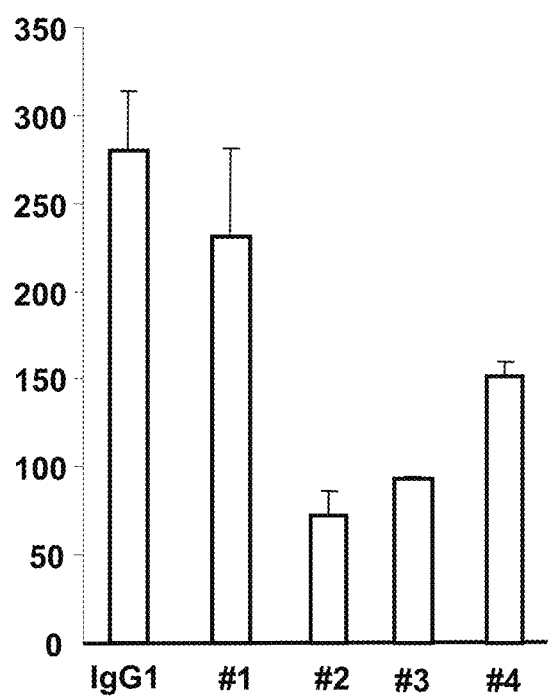

To measure inhibition of cell proliferation by antibodies, cells (Raji or SU-DHL-6 as described in Example 2) were seeded at a density of $2\times10^5$ cells per ml, with 100 µl per well. Cells are incubated with 100 µl of antibodies previously sterilized and diluted in RPMI-1640 medium ((Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland) to reach final concentrations of 0.0016 to 1 µg/ml (0.01 µM to 6.6 µM). Plates were incubated at 37° C., 5% $CO_2$ for 72 hours. 20 p. 1 of alamarBlue (AbD Serotec, Dusseldorf, Germany) was then added to cells for 4 to 8 h. Growing cells cause a chemical reduction in fluorescence of alamarBlue which is monitored by excitation at 540 nm and emission at 620 nm. Percentage differences between treated and untreated cells (vehicle only) were calculated from experiments performed in triplicate. FIG. 7A shows level of proliferation of SU-DHL-6 after 72 h incubation with antibodies. An irrelevant IgG1 and an anti-HLA-DR antibody which strongly binds SU-DHL-6 were used as negative and positive control, respectively. Humanized antibodies VH16-R94K-Y100BF/VL43-V3Q-T7S-Y32F-P44I-N92A, VH16-R94K/VL43-V3Q-T7S-P44I-N92A and VH16-R94K-Y100BF/VL43-V3Q-T7S-P44I-N92A (not shown) have strong inhibitory function on cell proliferation even at concentration as low as 0.01 µg/ml. Therefore, in addition to the early induction of apoptosis, anti-CD19 antibodies block B cell proliferation within 72 h.

Clonogenicity

Clonogenic assay is another method to assess tumor cell death by humanized anti-CD19 antibodies. The method is regularly used to evaluate the anti-proliferative function of antibodies (Chan H T C, Cancer Research 2003). We performed clonogenic assay using the colony-forming cell assay and complete MethoCult medium (StemCell Technologies, Grenoble, France). Raji cells (as described in Example 2) were prepared at $1\times10^6$ cells/ml and seeded at 100 µl/well in 96-well plates. Cells were then incubated with 100 µl of antibodies previously sterilized and diluted in RPMI-1640 medium ((Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland), antibody concentration was 0.2 µg/ml) for 90 minutes. Raji cells plus antibodies were then diluted in Iscove's medium to reach a count of 500 cells in 100 µl, and finally mixed with 1.1 ml of MethoCult medium. 0.8 ml of this preparation was dispensed in a 35 mm×10 mm dish using a tuberculin syringe. Cells were incubated for 9 days at 37° C. (5% $CO_2$) and colonies were counted with a microscope (50× magnification). The results shown in FIG. 7B correlate with humanized antibodies having surprising apoptotic properties (annexin-V plus PI staining) previously observed in Example 5, here, similarly, humanized antibodies show surprisingly good anti-proliferative properties while the parental chimeric FMC63 had very little or no effect on clonogenicity. Humanized anti-CD19 antibodies strongly decreased the number of Raji clones either by inducing apoptosis and killing during the first 90 min of incubation or by inhibiting cell division or both. This experiment is representative of several experiments and was performed in duplicate. The results confirm the effect of humanized anti-CD19 antibodies on B cell killing and inhibition of proliferation.

Example 7

Figure 8:
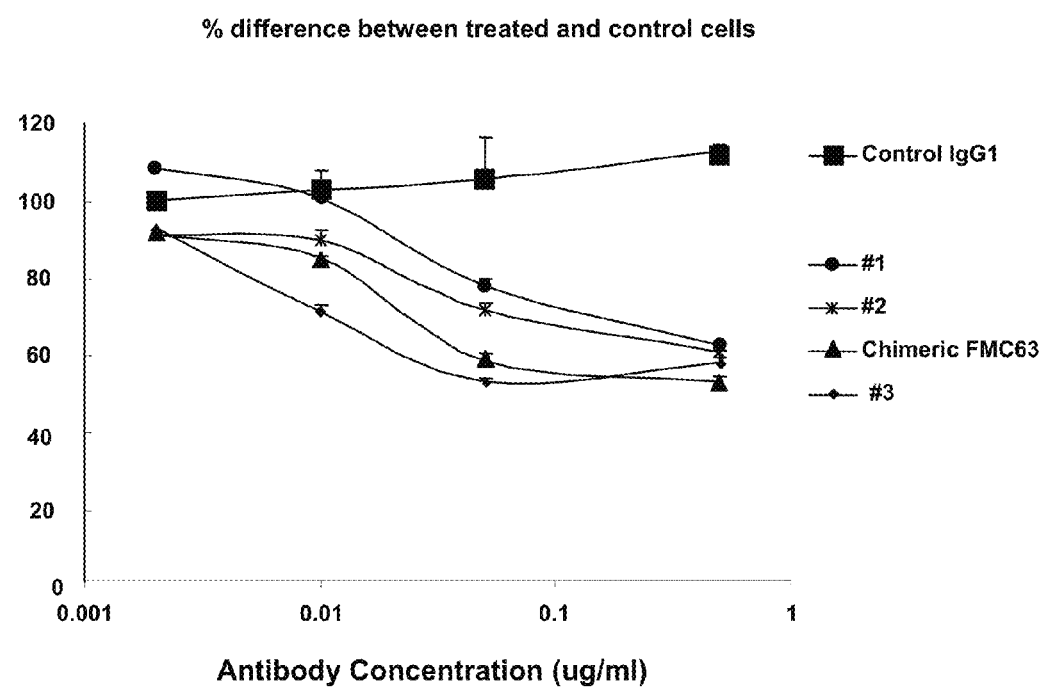
FIG. 8 shows internalization of anti-CD19 antibodies in Raji tumor cells. The internalization is monitored by the cytotoxicity of a saporin-conjugated secondary antibody (Hum-ZAP).

Internalization of Anti-CD19 Monoclonal Antibody Internalization Using Hum-Zap Assays To evaluate antibody internalization, a secondary anti-human antibody conjugated to the toxin saporin (Hum-Zap, Advanced Targeting Systems, San Diego, Calif., USA) was used. When internalized saporin, a ribosome-inactivating protein, induces cell death, which can be subsequently monitored using alamarBlue assays. Raji cells as described in Example 2 were seeded at $1\times10^5$ cells/ml, 100 µl per well in RPMI-1640 medium (Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland). Antibodies were diluted in Hum-Zap previously prepared at 100 ng/10 µl in RPMI-1640 complete cell medium (above). Ten µl of the mixture antibody plus Hum-Zap were added on Raji cells. The final concentrations of the antibodies ranged from 0.5 to 0.005 µg/ml. Cells with antibodies were then incubated for 48 h before measurement of cytotoxicity using alamarBlue. The percentage of cell proliferation was calculated as followed: Fluorescence (emission 590 nm) of antibody-treated cells/fluorescence (emission 590 nm) of control cells (Hum-Zap only)×100. Controls with antibodies and without Hum-Zap were also performed and did not show any significant effects on cell proliferation after 48 h. We observed internalization of the humanized anti-CD19 antibodies (FIG. 8). The internalization of CD19 subsequently to the interaction with antibodies has already been described in previous studies but remained not significant after 6 h and little after 24 h in Raji cells and in fresh B cells from peripheral blood as well (Ingle G. S. et al, BJH, 2007, 140, p 46-58). Using Hum-Zap, the humanized anti-CD19 VH16-R94K/VL43-V3Q-T7S-P44I-N92A antibody internalizes very similarly to the parental chimeric FMC63. However the antibody VH16-R94K-Y100BF/VL43-V3Q-T7S-Y32F-P44I-N92A displays much less internalization, with no internalization at 10 ng/ml. A high level of internalization is only desirable when designing therapeutic antibodies to be used as conjugate with a cytotoxic-payload or toxin.

Example 8

Thermostability of Anti-CD19 Monoclonal Antibodies by Differential Scanning Calorimetry The thermal stability of the humanized anti-CD19 monoclonal antibodies and chimeric FMC63 were compared using calorimetric measurements as shown in Tables 8, 12-16, and 19. Monoclonal antibodies melting profiles are characteristic of their isotypes (Garber and Demarest (2007), BBRC 355: 751-7), however the mid-point melting temperature of the FAB fragment can be easily identified even in the context of a full-length IgG. Such mid-point melting of FAB portion was used to monitor monoclonal stability of humanized candidates.

Calorimetric measurements were carried out on a VP-DSC differential scanning microcalorimeter (MicroCal, Northampton, UK). The cell volume was 0.128 ml, the heating rate was 1° C./min, and the excess pressure was kept at 64 p.s.i. All protein fragments were used at a concentration of 1-0.5 mg/ml in PBS (pH 7.4). The molar heat capacity of each protein was estimated by comparison with duplicate samples containing identical buffer from which the protein had been omitted. The partial molar heat capacities and melting curves were analyzed using standard procedures. Thermograms were baseline corrected and concentration normalized before being further analyzed using a Non-Two State model in the software Origin v7.0.

Example 9

B Cell Depletion Studies

B Cell Depletion in Human Whole Blood

To assess the ability of humanized anti-CD19 antibodies to deplete B cells in human whole blood, B cell depletion assays were performed. Peripheral blood was obtained by venipuncture and was diluted by 2 in RPMI-1640 medium ((Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland). Diluted whole blood was seeded in a 24 well-plate (1-2 mL per well), 10 µg/ml of antibody or PBS (untreated) were added and plates were incubated for 24 h at 37° C., 5% $CO_2$. The blood was lysed twice with RBC lysis buffer (eBiosciences, THP Medical Products, Vienna, Austria) for 5 min at room temperature and centrifuged at 1100 RPM for 3 min. The cell pellet was washed with 2 ml of binding buffer (PBS, 2.5% FCS, 100 mg/l $MgCl_2$, 0.5 mM $CaCl_2$, 0.05% $NaN_3$ and 10% Versene (v/v)). Cells were then resuspended in 0.5 ml of binding buffer and stained with either anti-CD19-PE-Cy5 or anti-CD20-PE, or anti-CD22-FITC antibodies. After 20 minutes incubation on ice, cells were washed once with binding buffer and analyzed by flow cytometry. The percentage of B-cells was determined and the percent change was calculated as followed: (% of B-cells in the untreated (PBS) cells−% of B-cells in the antibody-treated cells)/(% of B-cells in the untreated (PBS) cells)×100.

10 µg/ml of the antibody was used on four blood donors as shown in Table 21 and B cell depletion in whole blood was observed after treatment with humanized anti-CD19 antibodies while. No change in B cell number was observed after a control IgG1 treatment. Typically, $CD19^+$ or $CD20^+$ or $CD22^+$ B cells represented 9 to 10% of the leukocyte population when incubated with the control IgG1. The antibody VH16-R94K-Y100BF/VL43-V3Q-T7S-P44I-N92A had the highest impact on B cell depletion (average=15.25%) while the parental chimeric FMC63 was the least efficient (average=7.25%).

TABLE 21

B-cell depletion from whole blood.

| Antibody (10 ug/ml) | % Change | | | | |
|---|---|---|---|---|---|
| | Donor 1 | Donor 2 | Donor 3 | Donor 4 | Average |
| No Ab (PBS) | 0 | 0 | 0 | 0 | 0 |
| Control IgG1 | 0 | 0 | 0 | 0 | 0 |
| VH16-R94K/VL43-V3Q-T7S-P44I-N92A | 5 | 4 | 22 | 19 | 12.5 ± 8.0 |
| VH16-R94K-Y100$_B$F/VL43-V3Q-T7S-P44I-N92A | 15 | 20 | 10 | 16 | 15.25 ± 3.5 |
| Chimeric FMC63 | 0 | 10 | 12 | 7 | 7.25 ± 4.54 |

Example 10

VH16 R94K-VL43 V3Q/T7S/P44I/N92A Variants with Enhanced Complement-Mediated Effector Function A number of variants were designed with the goal of enhancing complement dependant cytotoxicity (CDC). In the same way that Fc interactions with Fcγ receptors binding mediates ADCC, Fc interactions with the complement component C1q mediates CDC. Although there is currently no structure available for the Fc/C1q complex, several studies have mapped the binding site on human IgG for C1q to a region centred on residues D270, K322, P329 and P331 (Idusogie et al., The Journal of Immunology, 2000, 164:4178-4184) Amino acid modifications were designed in the D269-K334 region of the CH2 domain to explore variants that may mediate enhanced CDC for VH16 R94K-VL43 V3Q/T7S/P44I/N92A.

The study shows that substitution of residues at position E269, S298 and S324 resulted in variants with at least about 1.6 fold (FIG. 9) to a maximum of 5.5 fold (FIG. 10) increase in CDC.

To create these variant cDNA coding sequences, a cDNA coding the VH16 R94K heavy chain (SEQ ID NO: 64) cDNA was converted to heavy chains VH16 R94K/324(NNK), VH16 R94K/S298A (SEQ ID NO: 114), VH16 R94K/E269D/S298A (SEQ ID NO: 115), VH16 R94K/S298A/S324N (SEQ ID NO: 116), VH16 R94K/E269D/S298A/S324N (SEQ ID NO: 117), by standard mutagenesis. NNK at position 324 describes the substitution of the wild-type serine encoding codon with a NNK codon which provides substitution with all 20 amino acids (hard randomization).

These variant coding DNA sequences were ligated in a vector that is based on a modified pREP4 (Invitrogen, CA, USA) vector carrying CMV promoter and Bovine Growth Hormone poly-adenylation signal. In this expression-vector, secretion was driven by the murine VJ2C leader peptide.

For transient expression, equal quantities of each heavy chain and light chain vectors was co-transfected into suspension-adapted HEK-EBNA cells (ATCC-CRL-10852) using Polyethyleneimine (PEI). Typically, 100 ml of cells in suspension at a density of 0.8-1.2 million cells per ml is transfected with a DNA-PEI mixture containing 50 µg of expression vector encoding the variant heavy chain and 50 μg expression vector encoding the VL43 V3Q/T7S/P44I/N92A (SEQ ID NO: 65) light chain. When recombinant expression vectors encoding each engineered chain genes are introduced into the host cells, the construct is produced by further culturing the cells for a period of 4 to 5 days to allow for secretion into the culture medium (EX-CELL 293, HEK293-serum-free medium, Sigma, Buchs, Switzerland), supplemented with 0.1% pluronic acid, 4 mM glutamine, and 0.25 μg/ml geneticin. The construct was then purified from cell-free supernatant using recombinant Streamline rProtein A media (GE, Switzerland), and used for further analysis.

The expression levels of these variants are listed in Table 22.

TABLE 22

IgG transient expression level of VH16 R94K/VL43 V3Q-T7S-P44I-N92A heavy chain variants.

| Antibody | Expression (mg/L) |
|---|---|
| VH16 R94K-VL43 V3Q/T7S/P44I/N92A | 38 |
| VH16 R94K/S324A-VL43 V3Q/T7S/P44I/N92A | 48 |
| VH16 R94K/S324V-VL43 V3Q/T7S/P44I/N92A | 1.5 |
| VH16 R94K/S324L-VL43 V3Q/T7S/P44I/N92A | 20 |
| VH16 R94K/S324I-VL43 V3Q/T7S/P44I/N92A | 24 |
| VH16 R94K/S324P-VL43 V3Q/T7S/P44I/N92A | 15 |
| VH16 R94K/S324T-VL43 V3Q/T7S/P44I/N92A | 0.5 |
| VH16 R94K/S324C-VL43 V3Q/T7S/P44I/N92A | 10 |
| VH16 R94K/S324M-VL43 V3Q/T7S/P44I/N92A | 24 |
| VH16 R94K/S324N-VL43 V3Q/T7S/P44I/N92A | 54 |
| VH16 R94K/S324Q-VL43 V3Q/T7S/P44I/N92A | 44 |
| VH16 R94K/S324F-VL43 V3Q/T7S/P44I/N92A | 48 |
| VH16 R94K/S324Y-VL43 V3Q/T7S/P44I/N92A | 61 |
| VH16 R94K/S324W-VL43 V3Q/T7S/P44I/N92A | 62 |
| VH16 R94K/S324R-VL43 V3Q/T7S/P44I/N92A | 35 |
| VH16 R94K/S324D-VL43 V3Q/T7S/P44I/N92A | 42 |
| VH16 R94K/S324G-VL43 V3Q/T7S/P44I/N92A | 27 |
| VH16 R94K/S324K-VL43 V3Q/T7S/P44I/N92A | 7 |
| VH16 R94K/S324E-VL43 V3Q/T7S/P44I/N92A | 26 |
| VH16 R94K/S324H-VL43 V3Q/T7S/P44I/N92A | — |
| VH16 R94K/S298A-VL43 V3Q/T7S/P44I/N92A | 54 |
| VH16 R94K/E269D/S298A-VL43 V3Q/T7S/P44I/N92A | 12 |
| VH16 R94K/S298AS324N-VL43 V3Q/T7S/P44I/N92A | 30 |
| VH16 R94K/E269D/S298AS324N-VL43 V3Q/T7S/P44I/N92A | 11 |

Complement Mediated Toxicity on Raji Cells

A cell-based assay was used to measure the capacity of the variants to mediate CDC.

Lysis was measured using release of lactate dehydrogenase (LDH) to monitor lysis of variant-opsonized Raji cells by baby rabbit complement (Harlan Laboratories, C-0099F, AN VENRAY, The Netherlands). Target cells were washed 2 times with complete medium (RPMI-1640 medium (Chemie Brunschwig AG, PAA, Basel, Switzerland) supplemented with 10% fetal bovine serum (FBS, Chemie Brunschwig AG, PAA, Basel, Switzerland) and 1% Ultraglutamine (Lonza, Verviers, Belgium)) by centrifugation and resuspension. Variant-antibodies were added at the indicated final concentrations of 1 μg/ml. Baby rabbit serum was diluted to 7.5% with complete medium and added to antibody-opsonized target cells. Plates were incubated for 3 hours at 37° C. Cell cytotoxicity was measured using the Cyto Tox 96 Non-Radioactive Cytotoxicity Assay kit (Promega, Madison, USA).

Figure 9:
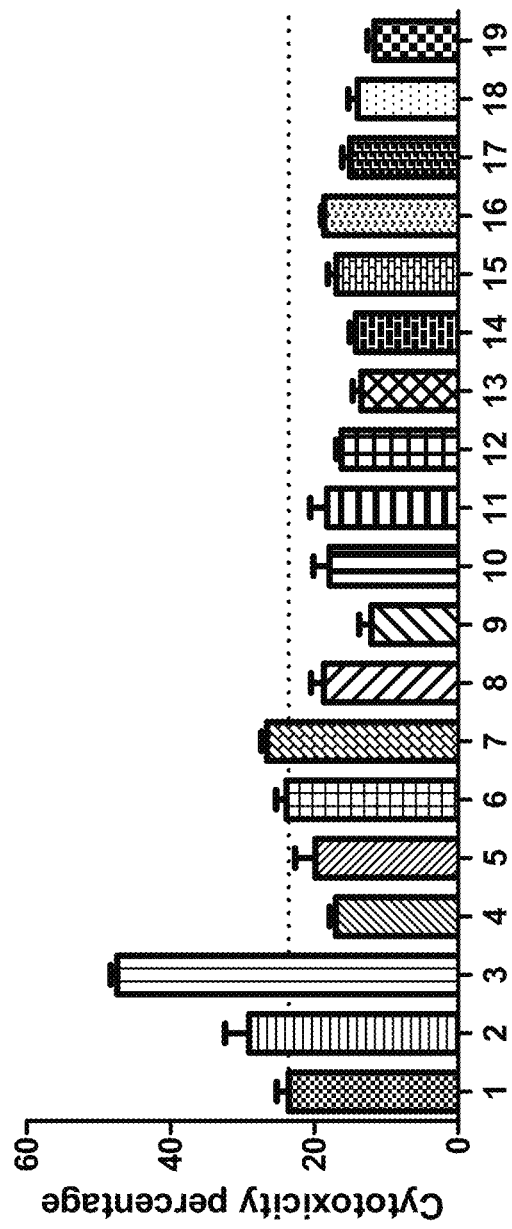
FIG. 9 shows complement dependent cytotoxicity (CDC) of anti-CD19 antibody mutants at position S324, compared to wild type VH16 R94K-VL43 V3Q/T7S/P44I/N92A: (1) IgG1 control antibody; (2) VH16 R94K-VL43 V3Q/T7S/P44I/N92A; (3) VH16 R94K/S324N-VL43 V3Q/T7S/P44I/N92A; (4) VH16 R94K/S324G-VL43 V3Q/T7S/P44I/N92A; (5) VH16 R94K/S324A-VL43 V3Q/T7S/P44I/N92A; (6) VH16 R94K/S324V-VL43 V3Q/T7S/P44I/N92A; (7) VH16 R94K/S324L-VL43 V3Q/T7S/P44I/N92A; (8) VH16 R94K/S324I-VL43 V3Q/T7S/P44I/N92A; (9) VH16 R94K/S324P-VL43 V3Q/T7S/P44I/N92A; (10) VH16 R94K/S324T-VL43 V3Q/T7S/P44I/N92A; (11) VH16 R94K/S324C-VL43 V3Q/T7S/P44I/N92A; (12) VH16 R94K/S324M-VL43 V3Q/T7S/P44I/N92A; (13) VH16 R94K/S324Q-VL43 V3Q/T7S/P44I/N92A; (14) VH16 R94K/S324F-VL43 V3Q/T7S/P44I/N92A; (15) VH16 R94K/S324Y-VL43 V3Q/T7S/P44I/N92A; (16) VH16 R94K/S324W-VL43 V3Q/T7S/P44I/N92A; (17) VH16 R94K/S324R-VL43 V3Q/T7S/P44I/N92A; (18) VH16 R94K/S324D-VL43 V3Q/T7S/P44I/N92A; (19) serum only.
Figure 10:
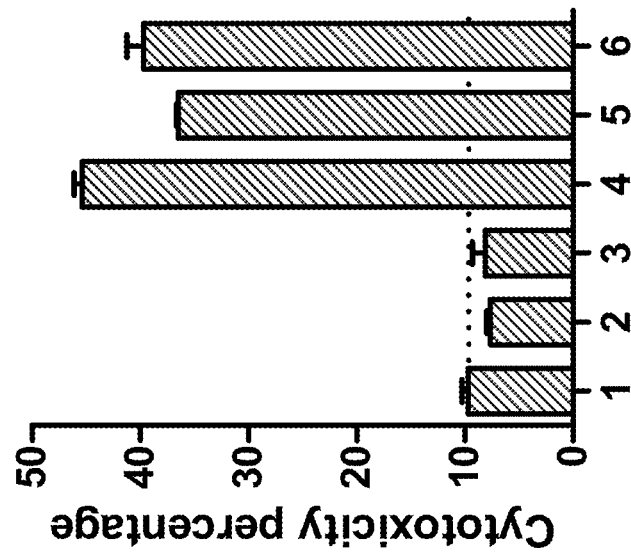
FIG. 10 shows CDC assay of anti-CD19 antibody variants with substitution at positions E269, S298 and S324: (1) negative control—no antibody; (2) IgG1 control antibody; (3) VH16 R94K-VL43 V3Q/T7S/P44I/N92A; (4) VH16 R94K/S324N-VL43 V3Q/T7S/P44I/N92A; (5) VH16 R94K/S298A/S324N-VL43 V3Q/T7S/P44I/N92A; (6) VH16 R94K/E269D/S298A/S324N-VL43 V3Q/T7S/P44I/N92A.

Representative data from this assay are shown in FIG. 9 and FIG. 10.

FIG. 9 and FIG. 10 show little specific lysis due to IgG1 control antibody (Herceptin®, Roche Pharma A.G., Reinach, Switzerland); however, complement-induced lysis was increased at least 1.6 fold (FIG. 9) to a maximum of 5.5 fold (FIG. 10) for the VH16 R94K/S324N (SEQ ID NO: 118)-VL43 V3Q/T7S/P44I/N92A (SEQ ID NO: 65) antibody depending on the variability of the assay which is due to the variation in raji cells viability; both VH16 R94K/S298A/S324N (SEQ ID NO: 116)-VL43 V3Q/T7S/P44I/N92A (SEQ ID NO: 65) antibody and VH16 R94K/E269D/S298A/S324N (SEQ ID NO: 117)-VL43 V3Q/T7S/P44I/N92A (SEQ ID NO: 65) antibody also exhibited improved CDC (at least 4.4 fold) over the parental antibody. FIGS. 9 and 10 show results in triplicate±standard deviation.

Example 11

VH16 R94K-VL43 V3Q/T7S/P44I/N92A Variants with Enhanced Antibody-Dependent Cellular Cytotoxicity (ADCC)

Anti-CD19 antibody variants investigated in the study described in Example 10 with substitution of residues at position E269, S298 were assessed for their ability to elicit ADCC.

ADCC activities of antibodies were measured by lactate dehydrogenase (LDH)-releasing assay using the CytoTox 96 Non-Radioactive Cytotoxicity Assay kit (Promega, Madison, USA). Human peripheral blood mononuclear cells (PBMC) were purified from citrated whole blood by standard Ficoll-paque separation, resuspended in complete medium (RPMI-1640 medium (Chemie Brunschwig AG, PAA, Basel, Switzerland) supplemented with 10% fetal bovine serum (FBS, Chemie Brunschwig AG, PAA, Basel, Switzerland), 2 mM ultraglutamine 1 (Lonza, Verviers, Belgium) and 1% penicillin/streptomycin (Chemie Brunschwig AG, PAA, Basel, Switzerland)), and 100 U/ml of human IL-2 (Sigma, Mo., USA)) and incubated overnight at 37° C. The following day, PBMC were collected by centrifugation, washed twice and resuspended in culture medium at a density of $8 \times 10^6$ cells/ml. The CD19+ cell line Raji as described in Example 2 was used as target cells. Raji cells were washed twice and resuspended in complete medium at a density of $0.2 \times 10^6$ cells/ml. Fifty microliters of antibody diluted at 1.5 μg/ml (final concentration was 0.5 μg/ml) were mixed with 50 μl of target cells, and added to an equivalent volume of PBMC into a U-bottomed 96-well plate. A target to effector ratio of 1:40 was used throughout the experiments. After 4 hours incubation at 37° C., cells were centrifuged and 50 μl samples of cell-free supernatant were collected, transferred to a flat-bottomed 96-well plate, and assayed. Percentage of lysis was calculated as follows: (Sample release−Target spontaneous release−Effector spontaneous release)/(Maximum release−Target spontaneous release)*100; where Target spontaneous release is the fluorescence from wells which only contained target cells, Effector spontaneous release is the fluorescence from wells which only contained effector cells, and Maximum release is the fluorescence from wells containing target cells which have been treated with lysis buffer. Background percentage of lysis obtained in absence of antibody (Target+Effector cells) was subtracted from percentage of lysis of sample.

Figure 11:
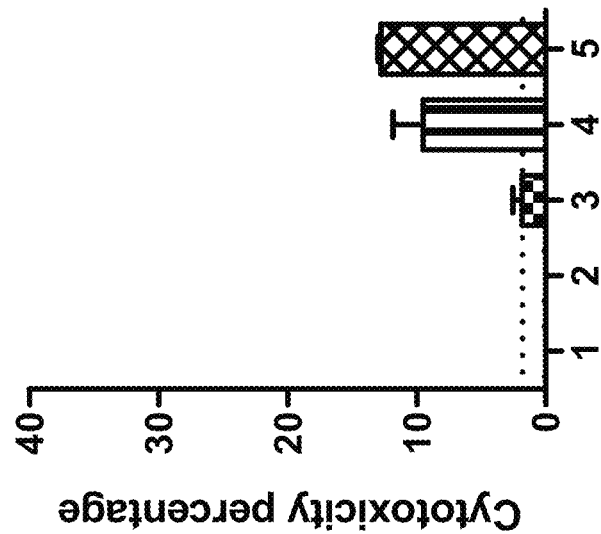
FIG. 11 shows cell-based ADCC assay of selected anti-CD19 antibody variants: (1) negative control—no antibody; (2) IgG1 control antibody; (3) VH16 R94K-VL43 V3Q/T7S/P44I/N92A; (4) VH16 R94K/S298A-VL43 V3Q/T7S/P44I/N92A; (5) VH16 R94K/E269D/S298A-VL43 V3Q/T7S/P44I/N92A.

FIG. 11 show no specific Raji lysis due to IgG control antibody (Herceptin®, Roche Pharma A.G., Reinach, Switzerland), and some cytotoxicity for the parental antibody; data shown are the mean cytotoxicity percentage±SD of triplicate wells using PBMC isolated from one donor. However, antibody-induced lysis was increased at least 5 fold for the VH16-R94K/S298A (SEQ ID NO: 114)-VL43-V3Q/T7S/P44I/N92A (SEQ ID NO: 65) antibody and at least 6.8 fold for the VH16-R94K/E269D/S298A (SEQ ID NO: 115)-VL43-V3Q/T7S/P44I/N92A (SEQ ID NO: 65) antibody.

This data demonstrates that selected the anti-CD19 antibody variants have enhanced cellular cytotoxicity towards CD19+ expressing cells.

Example 12

VH16 R94K-VL43 V3Q/T7S/P44I/N92A Variants with Enhanced Complement-Mediated Effector Function Based on Amino-Acids Substitutions Derived from Human Ig-Gamma3 and Human Ig-Gamma1/Ig-Gamma3 Hinge-Fc Domains Shuffling Human IgG3 antibodies have generally enhanced CDC to human IgG1 antibodies, this due in part because IgG3 Fc has higher C1q-binding affinity than IgG1 Fc (Schumaker V N et al., Biochemistry, 1976, 15:5175-81.)

Amino acid modifications in the Fc region of VH16 R94K were undertaken based on the differences in sequence between the human-IgG3 and human IgG1 Fc portions. In a complementary approach, a shuffling of the human IgG1 hinge and constant domains with the hinge and constant domains of the human IgG3 was performed to generate a chimeric isotype of anti CD19 antibody with enhanced CDC.

The study shows that substitution of residues at position K274 and N276 and a chimeric variant consisting of the CH1 and the hinge each from IgG1 and the Fc from IgG3 (designated by the 1133 suffix) resulted in an increase of 1.7 and 2.2 fold in CDC, respectively.

To create a variant cDNA coding sequence with substitution of residues at position K274 and N276, a cDNA coding the VH16 R94K heavy chain (SEQ ID NO: 64) cDNA was converted to heavy chains VH16 R94K/K274Q (SEQ ID NO: 119), VH16 R94K/N276K (SEQ ID NO: 120), VH16 R94K/K334R (SEQ ID NO: 121), VH16 R94K/K274Q/N276K (SEQ ID NO: 122), and VH16 R94K/K274Q/N276K/K334R (SEQ ID NO: 123) by standard mutagenesis techniques.

Furthermore by substituting a part of heavy chain gene (encoding Kabat residues 231 to its carboxyl terminus) in the expression vector for VH16 R94K-VL43 V3Q/T7S/P44I/N92A IgG1 with the corresponding part of a human IgG3 heavy chain gene (NCBI GenBank accession no. X03604.1, residues 161 to 377) a human anti CD19 VH16 R94K (1133) (SEQ ID NO: 124)-VL43 V3Q/T7S/P44I/N92A (SEQ ID NO: 65) chimeric isotype was generated.

These variant coding DNA sequences were ligated in a vector that is based on a modified pREP4 (Invitrogen, CA, USA) vector carrying CMV promoter and Bovine Growth Hormone poly-adenylation signal. In the expression-vector, secretion was driven by the murine VJ2C leader peptide.

For transient expression of these variants, equal quantities of each heavy chain and light chain vectors was co-transfected into suspension-adapted HEK-EBNA cells (ATCC-CRL-10852) using Polyethyleneimine (PEI). Typically, 100 ml of cells in suspension at a density of 0.8-1.2 million cells per ml is transfected with a DNA-PEI mixture containing 50 µg of expression vector encoding the variant heavy chain and 50 µg expression vector encoding the VL43 V3Q/T7S/P44I/N92A (SEQ ID NO: 65) light chain. When recombinant expression vectors encoding each engineered chain genes are introduced into the host cells, the construct is produced by further culturing the cells for a period of 4 to 5 days to allow for secretion into the culture medium (EX-CELL 293, HEK293-serum-free medium, Sigma, Buchs, Switzerland), supplemented with 0.1% pluronic acid, 4 mM glutamine, and 0.25 µg/ml geneticin). The construct was then purified from cell-free supernatant using recombinant Streamline rProtein A media (GE, Switzerland), and used for further analysis.

The expression levels of these variants are listed in Table 23.

TABLE 23

IgG transient expression level of VH16 R94K/VL43 V3Q-T7S-P44I-N92A heavy chain variants.

| Antibody | Expression (mg/L) |
|---|---|
| VH16 R94K/K274Q/N276K-VL43 V3Q/T7S/P44I/N92A | 12 |
| VH16 R94K (1133)-VL43 V3Q/T7S/P44I/N92A | 21 |

Complement Mediated Toxicity on Raji Cells

A cell-based assay was used to measure the capacity of the variants to mediate CDC according to example 10. Lysis was measured using release of lactate dehydrogenase (LDH) to monitor lysis of variant-opsonized Raji cells by baby rabbit complement (Harlan Laboratories, C-0099F, AN VENRAY, The Netherlands). Target cells were washed 2 times with complete medium (RPMI-1640 medium (Chemie Brunschwig AG, PAA, Basel, Switzerland) supplemented with 10% fetal bovine serum (FBS, Chemie Brunschwig AG, PAA, Basel, Switzerland) and 1% Ultraglutamine (Lonza, Verviers, Belgium) by centrifugation and resuspension. Variant-antibodies were added at the indicated final concentration of 1 µg/ml. Baby rabbit serum was diluted to 5% with complete medium and added to antibody-opsonized target cells. Plates were incubated for 3 hours at 37° C.

Cell cytotoxicity was measured using the Cyto Tox 96 Non-Radioactive Cytotoxicity Assay kit (Promega, Madison, USA). Representative data from this assay is shown in FIG. 12.

Figure 12:
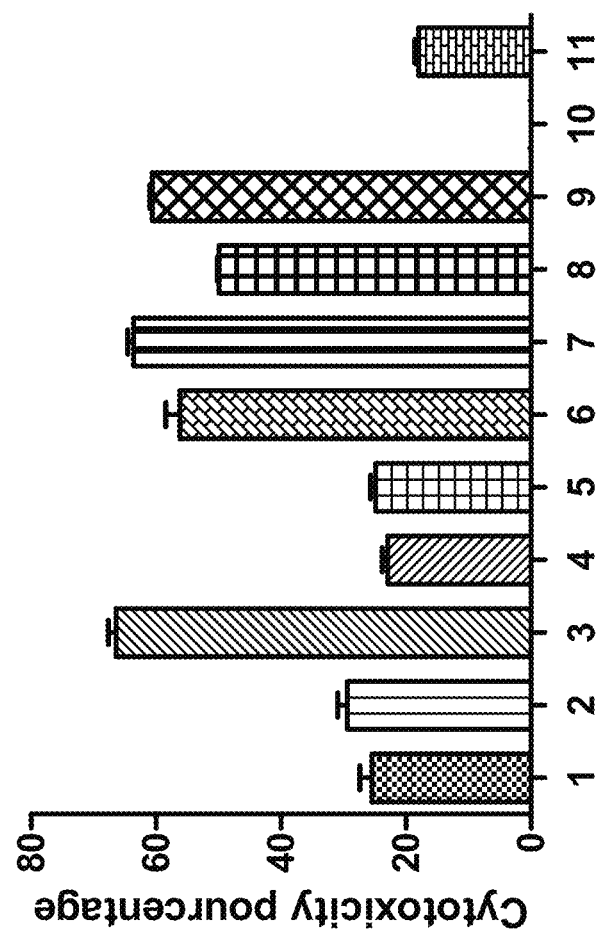
FIG. 12 shows cell-based CDC assay of selected anti-CD19 antibody variants: (1) IgG1 control antibody: (2) VH16 R94K-VL43 V3Q/T7S/P44I/N92A; (3) VH16 R94K (1133) -VL43 V3Q/T7S/P44I/N92A; (4) VH16 R94K/K274Q-VL43 V3Q/T7S/P44I/N92A; (5) VH16 R94K/N276K-VL43 V3Q/T7S/P44I/N92A; (6) VH16 R94K/K334R-VL43 V3Q/T7S/P44I/N92A; (7) VH16 R94K/S324N-VL43 V3Q/T7S/P44I/N92A; (8) VH16 R94K/K274Q/N276K-VL43 V3Q/T7S/P44I/N92A; (9) VH16 R94K/K274Q/N276K/K334R-VL43 V3Q/T7S/P44I/N92A; (10) negative control—no antibody—no serum; (11) negative control—serum only.

FIG. 12 shows little specific lysis due to IgG1 control. when compared to the parental antibody, Complement-induced lysis was increased at least 1.7 fold for the VH16 R94K/K274Q/N276K (SEQ ID NO: 122)-VL43 V3Q/T7S/P44I/N92A (SEQ ID NO: 65) antibody, 2 fold for the VH16 R94K/K274Q/N276K/K334R (SEQ ID NO: 123)-VL43 V3Q/T7S/P44I/N92A (SEQ ID NO: 65) antibody and 2.2 fold for VH16 R94K (1133) (SEQ ID NO: 124)-VL43 V3Q/T7S/P44I/N92A (SEQ ID NO: 65) antibody. FIG. 12 shows results performed in triplicate±standard deviation.

Example 13

Establishment of Cell Lines for Expression of Anti-CD19 Antibodies

A high yielding, mammalian protein expression system was developed. The system is based on a well documented CHO cell line (CHO-S, Invitrogen, Basel, Switzerland) that was adapted to suspension growth in a chemically defined serum-free medium, a highly efficient transfection method and a screening strategy for identification of clonal populations of high-producer cell lines. This mammalian protein expression system was used for the stable expression of humanized variants of the anti CD19 antibody.

The plasmid carrying the cDNA sequence for the VL43 V3Q/T7S/P44I/N92A light chain (SEQ ID NO: 65) and the plasmid pAE18_VH16_R94K carrying the cDNA sequence for VH16 R94K heavy chain (SEQ ID NO: 64) used in Example 1 were both digested with XbaI and HindIII to release the light and heavy chain inserts. These inserts were isolated by gel electrophoresis, gel-extracted, purified and further cloned into the multiple cloning site of an expression vector based on pGL3 from Promega (Madison, Wis., USA), that was previously digested with the same restriction enzymes and prepared using the same gel electrophoresis and purification methods. This yields two expression plasmids: the pGL41[18_HC] plasmid and the pGL41[18_LC] plasmid respectively carrying the heavy chain and the light chain of the VH16 R94K-VL43 V3Q/T7S/P44I/N92A anti CD19 antibody.

The vector pSV2neo, expressing the geneticin resistance gene neo was purchased from Clontech (Mountain View, Calif., USA) and the puromycin resistance vector pSV-Puro was obtained by cloning the SV40 promoter and the puromycin resistance gene (pac) from pBABE-Puro (Addgene, Camebridge, Mass., USA) into the pGL3 vector from Promega. These four plasmids were linearized using a single restriction site in the ampicillin resistance gene (ampR) and purified from remaining salts by ethanolic precipitation. Similarly, expression vectors for further humanization variants (VH16 R94K/Y100$_B$F (SEQ ID NO: 66)-VL43 V3Q/T7S/P44I/N92A (SEQ ID NO: 65) and VH16 R94K/Y100$_B$F (SEQ ID NO: 66)-VL43 V3Q/T7S/Y32F/P44I/N92A (SEQ ID NO: 67)) were cut out using the same restriction enzymes as described above and cloned into the pGL41 backbone.

For stable integration into the host cell line CHO-S (Invitrogen), cells are seeded in 10 ml at a density of $1 \times 10^6$ cells per ml in a 50 ml bioreactor filter tube (TPP, Trasadingen, Switzerland) and cultured overnight. Prior to transfection, the chemically defined cell culture medium (PowerCHO2, Lonza, Basel, Switzerland) was replaced with the transfection medium (Opti-MEM, Invitrogen). Cells were transfected with 12.5 μg of the linearized vector cocktail containing the mix of heavy and light chain expression plasmids, pSV-Puro and pSV2neo using the polykationic transfection agent JetPEI (Polyplus-transfections, Illkirch, France) according to manufacturer's instructions. 4-5 hours after transfection, cells were diluted with 1 volume of growth medium. The following day cells were diluted in a ratio of 1 to 10, 1 to 20 or 1 to 30 in growth medium containing 5.0 μg/ml of puromycin and 500 ug/ml geneticin and distributed in 96 well plates. After 14 days of selection, drug resistant colonies were assayed using an antibody specific-ELISA and positive individual clones were amplified for antibody production analysis. The best performing clones were diluted at the concentrations 1, 10 and 100 cells/ml in cell culture medium (PowerCHO2, Lonza) in order to obtain clonal populations. Finally, best producing clones yielded titers in the range of 400 to 600 mg/L for the VH16 R94K-VL43 V3Q/T7S/P44I/N92A antibody and 200-300 mg/L for the VH16 R94K/Y100$_B$F-VL43 V3Q/T7S/P44I/N92A and VH16 R94K/Y100$_B$F-VL43 V3Q/T7S/Y32F/P44I/N92A antibodies in a 12 day shaken-batch assay using the PowerCHO2 cell culture medium supplemented with glutamine.

Example 14

Production of Defucosylated Variants of Anti CD19 Antibody

In mammals, fucose residues are attached to innermost GlcNAc residue of almost all complex-type Asn-linked oligosaccharides via an α1,6 linkage. A stable cell line expressing the rat beta-1,4-mannosyl-glycoprotein 4-beta-N-acetylglucosaminyltransferase (GNTIII) enzyme was prepared. This enzyme introduces a bisecting N-Acetylglucosamine in the N-linked oligosaccharides of glycoproteins like for example antibodies. Such modification turns the antibody's Fc oligosaccharide into an inaccessible substrate for the enzyme Fut8 which transfers a fucose residue to the reducing N-Acetylglucosamine of glycan tree (Longmore and Schachter, 1982, Carbohydr Res 365-92), thereby inhibiting fucosylation. The rat gntIII gene was ordered from Imagenes (Berlin, Germany) and amplified using specific primers. The amplicon was then digested using the enzymes BamHI and HindIII, gel purified and cloned into the BamHI, HindIII opened multiple cloning site of the expressing vector pGLEX33; a mammalian expression vector based on the pcDNA3.1 plasmid from Invitrogen (Basel, Switzerland) under control of the mouse CMV promoter. The resulting vector was called pGNTIII.

The puromycin resistance vector pSV-Puro was obtained by cloning the SV40 promoter and the puromycin resistance gene (pac) from pBABE-Puro (Addgene, Camebridge, Mass., USA) into the pGL3 vector from Promega (Madison, Wis., USA. The two plasmids were linearized using a single restriction site in the ampicillin resistance gene (ampR) and purified from remaining salts by ethanolic precipitation.

For stable integration into the host cell line CHO-S (Invitrogen), cells are seeded in 10 ml at a density of $1 \times 10^6$ cells per ml in a 50 ml bioreactor filter tube (TPP, Trasadingen, Switzerland) and cultured overnight. Prior to transfection, the chemically defined cell culture medium (PowerCHO2, Lonza, Basel, Switzerland) was replaced with the transfection medium (Opti-MEM, Invitrogen). Cells were transfected with 12.5 μg of the linearized vector cocktail containing the mix of pGNTIII and pSV-Puro using the polykationic transfection agent JetPEI (Polyplus-transfections, Illkirch, France) according to manufacturer's instructions. 4-5 hours after transfection, cells were diluted with 1 volume of growth medium. The following day cells were diluted in a ratio of 1 to 10, 1 to 20 or 1 to 30 in growth medium containing 5.0 μg/ml of puromycin and distributed in 96 well plates. After 14 days of selection, drug resistant colonies expressing the rat GNTIII gene were isolated.

A second stable cell line was prepared using the CHO-S cell line from Invitrogen. The cells were transfected with a vector expressing two small hairpin RNAs (shRNA) that knock down the enzymes Fut8 (α1,6-fucosyltransferase) and GMD (GDP-mannose 4,6-dehydratase) using the shRNA sequences described previously (Imai-Nishiya et al. 2007, BMC Biotechnol., 7:84) under control of the human U6 promoter and the tRNA$^{Val}$ promoter. The construct was ordered from GeneArt A.G. (Regensburg, Germany). In detail, the tRNA$^{Val}$ promoter controls the expression of the Fut8 specific shRNA and the U6 promoter controls the expression of the GMD specific shRNA. The construct was flanked by NheI and NruI sites, and these restriction sites were used to clone the digested and gel purified fragment into the vector backbone of pGLEX1 (a modified version of pcDNA3.1 (Invitrogen) previously digested with the same enzymes.

The combined knockdown of these two enzymes of the de-novo pathway has been shown to have synergistic effects in promoting the absence of fucose in the N-linked oligosaccharide structure of IgG1 (Imai-Nishiya et al. 2007, BMC Biotechnol. 7:84), if the cells were cultured in the absence of fucose. In presence of fucose the reduction of the fucosylation would rely only on the knockdown of the Fut8 enzyme as the GMD enzyme is not part of the salvage pathway. The cells transfected with the double knockdown expression cassettes were previously shown to have lost 90-98% of the fucosylation in the N-linked oligosaccharides (Imai-Nishiya et al. 2007, BMC Biotechnol., 7:84). For stable integration into the host cell line CHO-S (Invitrogen), the siRNA vector was linearized using a single restriction site in the ampicillin resistance. The cells were co-transfected with a selection plasmid and selected as described above for the The two cell lines were transiently transfected with plasmids encoding both the VH16 R94K (SEQ ID NO: 64)-VL43 V3Q/T7S/P44I/N92A (SEQ ID NO: 65) antibody and the VH16 R94K/E269D/S298A (SEQ ID NO: 115)-VL43 V3Q/T7S/P44I/N92A (SEQ ID NO: 65) antibody as described in Example 1 and 11, respectively.

For the transient transfection, cells were seeded in 200 ml at a density of $1\times10^6$ cells per ml in a 1000 ml round Schott bottle and cultured overnight. Prior to transfection, the chemically defined cell culture medium (PowerCHO2, Lonza) was replaced with 100 ml of the transfection medium (Opti-MEM, Invitrogen). Cells were transfected with 250 μg of the vector cocktail containing a mix of 50% heavy chain and 50% light chain DNA using the polykationic transfection agent JetPEI (Polyplus-transfections) according to manufacturer's instructions. 4-5 hours after transfection, cells were diluted with 1 volume of growth medium. The medium was harvested on day 5. After centrifugation, the supernatant was filtered (0.2 μm) and purified by protein-A affinity chromatography (Hitrap, GE healthcare, Zurich, Switzerland) on an Akta purifier system (GE healthcare). The ADCC assays were performed as described in example 11.

Figure 13:
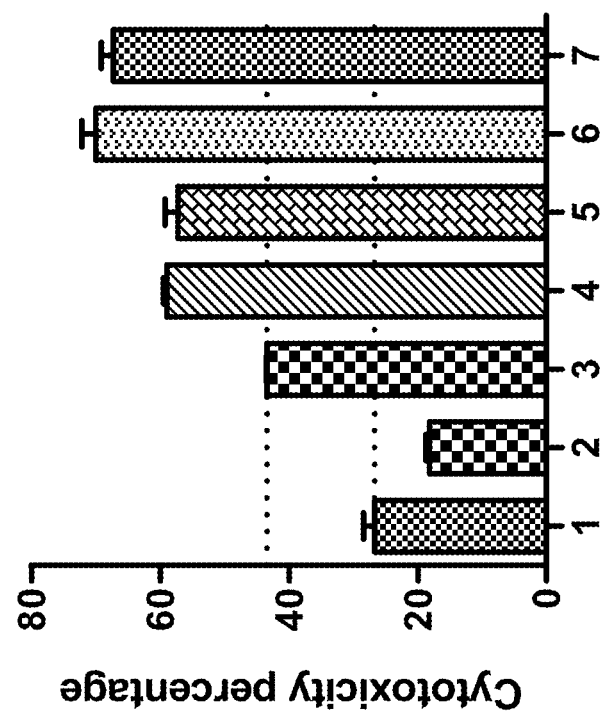
FIG. 13 shows cell-based ADCC assay of defucosylated anti-CD19 antibody variants: (1) negative control—no antibody; (2) IgG1 control antibody; (3) VH16 R94K-VL43 V3Q/T7S/P44I/N92A; (4) VH16 R94K (shRNA)-VL43 V3Q/T7S/P44I/N92A; (5) VH16 R94K (GNTIII)-VL43 V3Q/T7S/P44I/N92A; (6) VH16 R94K/E269D/S298A (shRNA)-VL43 V3Q/T7S/P44I/N92A; (7) VH16 R94K/E269D/S298A (GNTIII)-VL43 V3Q/T7S/P44I/N92A.

Antibody variants produced in the shRNA and the GNTIII cell lines described above are respectively designated by the shRNA or GNTIII suffix. FIG. 13 shows that defucosylated variants have increased ADCC over their fucosylated parental antibody by at least 2 fold.

Example 15

The Effect of Anti-CD19 Antibody on B-Cell Engraftment in Humanized SCID Mice This study was designed to assess the in vivo effect of anti-CD19 treatment of huPBL SCID mice. Before the start of treatment, 30 healthy female severe combined immunodeficiency (SCID, HARLAN) mice, 5-6 weeks-old and weighing 16-20 g were randomized based on body weight into one group of 2 animals and 4 groups of 7 animals. The mean body weight of each group was comparable and not statistically different from the other groups (analysis of variance). All mice were then submitted to whole body irradiation using a γ-source (1.8 Gy, 60Co, NRA BRETENIERE, Dijon, France) at D0. At D1 and D8, mice received a single SC injection of NK-cell depleting Ab (mCD122 antigen, Rat IgG2b isotype, TM-Beta 1, BioXCell, USA) at 20 mg/kg.

Four freshly collected buffy coat samples from healthy volunteer donors were obtained and the peripheral blood mononuclear cells (PBMCs) were purified using gradient centrifugation according to the Ficoll-Paque® plus procedure (Ref 07907, StemCell Technologies) within 48 h after total blood collection. The viability of PBMCs was assessed by 0.25% trypan blue exclusion before in vivo injection. At D3, mice were IP injected with $3\times10^7$ hPBMCs (500 μL in PBS by IP route) from donors #1, #2 and #3 (Groups 2 to 5, 2-3 mice per donor) or with PBS (Group 1). At D14, mice from groups 2, 3, 4 and 5 received a single IV injection of Herceptin® (negative control, 21.0 mg/ml, Batch No B1492), Mabthera® (positive control, 10.0 mg/ml, Batch No B2136), anti-CD 19 antibody variant VH16 R94K (SEQ ID NO: 64)-VL43 V3Q/T7S/P44I/N92A (SEQ ID NO: 65) or anti-CD 19 antibody variant VH16 R94K/S324N (SEQ ID NO: 118)-VL43 V3Q/T7S/P44I/N92A (SEQ ID NO: 65) at 10 mg/kg/inj, respectively. The treatment schedule is summarized in the table 24 below:

TABLE 24

Treatment schedule

| Group | No. mice | Irradiation | NK-cell depleting AB (D 1, D 8) | HPBMC (D 3) | Treatment (D 14, Q1Dx1) |
|---|---|---|---|---|---|
| 1 | 2 | Yes | Yes | No (PBS) | No |
| 2 | 7 | Yes | Yes | 3 donors 2-3 mice/donor | Herceptin ® (10 mg/kg, IV) |
| 3 | 7 | Yes | Yes | 3 donors 2-3 mice/donor | Mabthera ® (10 mg/kg, IV) |
| 4 | 7 | Yes | Yes | 3 donors 2-3 mice/donor | VH16 R94K-VL43 V3Q/T7S/P44I/N92A (10 mg/kg, IV) |
| 5 | 7 | Yes | Yes | 3 donors 2-3 mice/donor | VH16 R94K/S324N -VL43 V3Q/T7S/P44I/N92A (10 mg/kg, IV) |

The human B lymphocytes in the spleens were detected by 4-color flow cytometry analysis. For each sample, the human B lymphocytes cells were quantified using cell surface expression of hCD45(+), mCD45(−), hCD20(+) and hCD19(+) and PKH26 reference microbeads (Ref P7458, Sigma). Antibodies described in table 25 below were used.

TABLE 25

Antibodies for detection of human B lymphocytes cells

| Antigens | Clone | Isotype | Fluorochrome | Ref |
|---|---|---|---|---|
| hCD19 | 4G7 | Mouse IgG$_1$, κ | PerCP | BD[a] 345778 |
| hCD45 | H130 | | APC | BD 555485 |
| hCD20 | L27 | | FITC | BD 345792 |
| mCD45 | 30-F11 | Rat IgG$_{2b}$, κ | APC-Cy7 | BD 557659 |
| mIgG$_1$ | MOPC-21 | Mouse IgG$_1$ | FITC | BD 555748 |
| mIgG$_1$ | X40 | | PerCP | BD 345817 |
| mIgG$_1$ | MOPC-21 | | APC | BD 555751 |
| rIgG$_{2b}$ | A95-1 | Rat IgG$_{2b}$, κ | APC-Cy7 | BD 552773 |

[a]BD: Becton Dickinson Biosciences, Lo Pont de Claix, France

For the CD marker expression analyses, 100 000 cells from spleens in 200 μL staining buffer [PBS (Ref 17-516F, Lonza), 0.2% BSA (Ref A7030, Sigma) 0.02% NaN3 (Ref S2002, Sigma)] were incubated in the dark for 20 min at room temperature with either a mixed solution of hCD19 PerCP, hCD20 FITC, hCD45 APC and mCD45 APC-Cy7 antibodies or a mixed solution of mIgG1-FITC, rIgG2b-APC-Cy7, mIgG1-APC and mIgG1-PerCP antibodies. Isotype control antibodies were used in each case as negative controls.

The red blood cells were lysed using the "Fix and Lyse" procedure. Briefly, "Fix and Lyse" buffer was prepared by adding 25 μL of IOTest 3 10× Fixative Solution (Ref A07800, Beckman Coulter) to 1 mL of VersaLyse (Ref A09777, Beckman Coulter) and 1 ml of the mixture was added to the stained cells. After being vortexed and incubated for 10 min in the dark at room temperature, cells were centrifuged and washed once with 3 mL of staining buffer and resuspended in 0.5 mL of reference microbeads solution (PKH26, Ref P7458, Sigma, ½ diluted in staining buffer). The samples were stored on ice protected from light exposure until FACS analysis. The stained cells were analyzed with a CyFlow® space flow cytometer (Partec S.A.R.L.) using a 488 nm wavelength laser excitation. The acquisition was stopped after a total of 10,000 hCD45(+) (if achievable) were collected for each sample. All the events were saved during the acquisition.

FACS results were represented by dot plot showing FSC versus SSC parameters (forward and side scatter detectors) in order to visualize cells size and complexity, and by dot plots showing the hCD45 (FITC) fluorescence intensities.

Calculation of absolute cell counts was achieved by using the following formula:

$$ACN = \frac{CN}{BN} \times \frac{\text{beads concentration}}{2} \times V_f \times \frac{1}{V_i}$$

Figure 14:
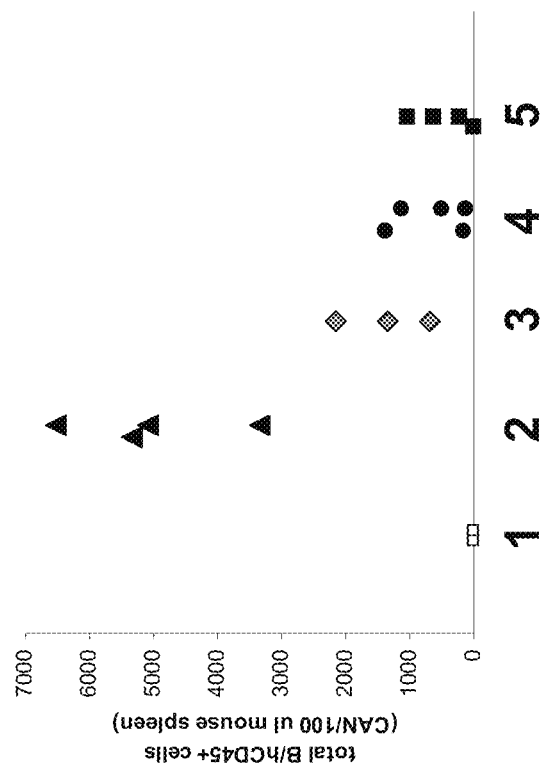
FIG. 14 shows B cell depletion (ACN of total B cells) by anti-CD19 antibody variants detected in the spleens of SCID mice: (1) negative control—no human PBMC; (2) human PBMC—Herceptin®; (3) human PBMC—Mabthera®; (4) human PBMC—VH16 R94K-VL43 V3Q/T7S/P44I/N92A; (5) human PBMC—VH16 R94K/S324N-VL43 V3Q/T7S/P44I/N92A.
Figure 15:
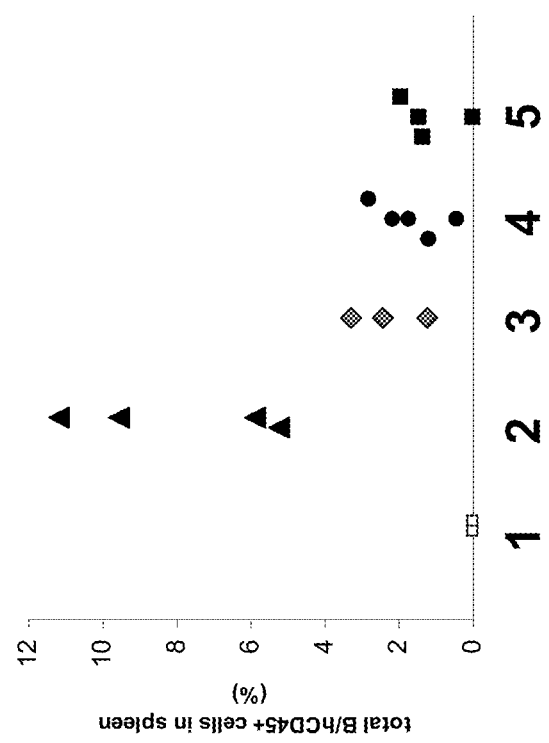
FIG. 15 shows B cell depletion (percentage of total B cells) by anti-CD19 antibody variants detected in the spleens of SCID mice: (1) negative control—no human PBMC; (2) human PBMC—Herceptin®; (3) human PBMC—Mabthera®; (4) human PBMC—VH16 R94K-VL43 V3Q/T7S/P44I/N92A; (5) human PBMC—VH16 R94K/S324N-VL43 V3Q/T7S/P44I/N92A.

Where:
ACN was the absolute cell number per μL
CN was the cell number.
BN was the bead number.
The beads concentration was specified at a latter date as depending on the batch provided by the manufacturer.
Vf (expressed in mL) was the volume of microbeads solution used to resuspended the cell pellet.
Vi (expressed in μL) was the initial volume of blood used for FACS analysis.
The individual ACN of total B cells in the spleens of engrafted SCID mice at D18 are presented in FIG. 14. The individual percentage of total B cells in spleens of engrafted SCID mice at D18 are presented in FIG. 15.

All mice, except one mouse from group hPBMC & anti-CD 19 variant V18 (mouse No 3817), were successfully engrafted with hPBMCs, resulting in detection of circulating human CD45+ leucocytes in mouse blood. The level of human CD45+ leucocytes was over to 15% of blood cells in most of the mice transplanted with hPBMC. Moreover, high levels of human cell reconstitution (reaching 31-73% hCD45+ leucocytes in blood cells) was observed in 52% of engrafted mice. Levels of hCD45+ leucocytes were unchanged or increased during the course of the experiment, reflecting the engraftment efficiency of SCID mice transplanted with human PBMC. Human CD45+ leucocytes were also detected in spleens 18 days after transplantation and the average engraftment level was approximately 45% hCD45+ cell in spleen cells.

The human B cell populations in the spleens were analyzed when mice were killed 4 days after dosing; that is to say 18 days after transplantation. In all engrafted mice from the negative control group, the spleens contained 5 to 11% B cells in hCD45+ leucocytes. Human B cells in the spleens constituted of either hCD19+ or hCD20+ single-positive cells as well as hCD19+ hCD20+ double-positive B cells. Only low levels (<3%) of human B cells were detected in the spleens from mice treated with Mabthera®, anti-CD 19 antibody variant VH16 R94K-VL43 V3Q/T7S/P44I/N92A or anti-CD 19 antibody variant VH16 R94K/S324N-VL43 V3Q/T7S/P44I/N92A and the decrease of the human B cell population was statistically significant in comparison with the Herceptin® group. On the other hand, no statistical difference was observed in the B cell depletion in the spleens between anti-CD 19 variant antibody VH16 R94K-VL43 V3Q/T7S/P44I/N92A or anti-CD 19 antibody variant VH16 R94K/S324N-VL43 V3Q/T7S/P44I/N92A and Mabthera® treatment.

Results demonstrated that a single IV injection of anti-CD 19 antibody variant VH16 R94K-VL43 V3Q/T7S/P44I/N92A or anti-CD 19 antibody variant VH16 R94K/S324N-VL43 V3Q/T7S/P44I/N92A at 10 mg/kg resulted in a B cell depletion in the spleens of treated mice and the response to the GBR antibodies was equivalent in intensity to that of Mabthera®.

---

We claim:

1. A humanized antibody or fragment thereof that binds to human CD19, wherein the humanized antibody or fragment thereof comprises a heavy chain variable region comprising the amino acid sequence of SEQ ID NO: 37 and a light chain variable region comprising the amino acid sequence of SEQ ID NO: 59, wherein the amino acid position of each group member is indicated utilizing the numbering system set forth in Kabat.

2. The humanized antibody or fragment thereof of claim 1, further comprising human heavy and/or light constant regions.

3. The humanized antibody or fragment thereof of claim 2, wherein the human heavy constant region comprises an isotypic variant comprising the CH1 from human IgG1, the hinge from human IgG1 and the Fc region from human IgG3.

4. The humanized antibody or fragment thereof of claim 1, wherein the antibody is a full length antibody.

5. The humanized antibody or fragment thereof of claim 1, wherein the antibody is an antibody fragment selected from the group consisting of Fab, Fab', Fab'-SH, Fv, F(ab')2, scFv, diabodies, and triabodies.

6. The, humanized antibody or fragment thereof of claim 1, wherein the antibody comprises a variant human IgG Fc region which comprises at least one amino acid modification relative to the human IgG Fc region of the parent antibody, whereas the antibody comprising the variant human IgG Fc region exhibits altered effector function compared to the parent antibody.

7. The humanized antibody or fragment thereof of claim 1, having a mature core carbohydrate structure attached to the human IgG Fc region as represented schematically below

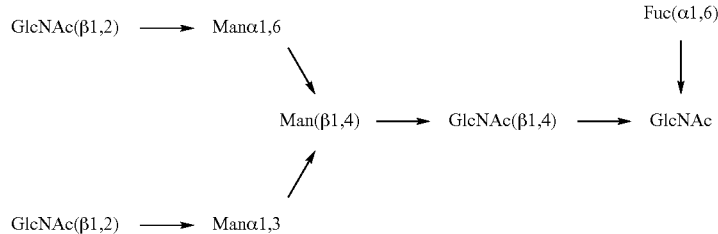

except that the Fuc(α1,6) residue is absent.

8. The humanized antibody or fragment thereof of claim 1, wherein the humanized antibody or fragment contains an Fc region and induces ADCC activity of Raji tumor cells.

9. A composition comprising the humanized antibody or fragment thereof of claim 1, and a pharmaceutically acceptable carrier.

10. An immunoconjugate comprising the humanized antibody or fragment thereof of claim 1, linked to a therapeutic agent.

11. A composition comprising the immunoconjugate of claim 10 and a pharmaceutically acceptable carrier.

12. An article of manufacture comprising the humanized antibody or fragment thereof of claim 1, for the treatment of a CD19 mediated disorder.

13. A kit comprising the humanized antibody or fragment thereof of claim 1, for the treatment of a CD19 mediated disorder.

14. A humanized antibody or fragment thereof that binds to human CD19, wherein the humanized antibody or fragment thereof comprises
   (a) a heavy chain sequence comprising the amino acid sequence of SEQ ID NO: 64; and
   (b) a light chain sequence comprising the amino acid sequence of SEQ ID NO: 65.

15. The humanized antibody or fragment thereof of claim 1, wherein the humanized antibody or fragment thereof comprises a light chain variable framework region sequence which is at least 95% identical to the light chain variable framework region sequence of SEQ ID NO: 59 or SEQ ID NO: 65 and/or wherein the humanized antibody or fragment thereof comprises a heavy chain variable framework region sequence which is at least 95% identical to the heavy chain variable framework region sequence of SEQ ID NO: 37 or SEQ ID NO: 64.

* * * * *

SEQUENCE LISTING

<160> NUMBER OF SEQ ID NOS: 126

<210> SEQ ID NO 1
<211> LENGTH: 120
<212> TYPE: PRT
<213> ORGANISM: Artificial
<220> FEATURE:
<223> OTHER INFORMATION: FMC63-VH NCBI-CAA74659

<400> SEQUENCE: 1

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu

```
                    65                  70                  75                  80
Lys Met Asn Ser Leu Gln Thr Asp Asp Thr Ala Ile Tyr Tyr Cys Ala
                        85                  90                  95

Lys His Tyr Tyr Tyr Gly Gly Ser Tyr Ala Met Asp Tyr Trp Gly Gln
                100                 105                 110

Gly Thr Ser Val Thr Val Ser Ser
            115                 120

<210> SEQ ID NO 2
<211> LENGTH: 107
<212> TYPE: PRT
<213> ORGANISM: Artificial
<220> FEATURE:
<223> OTHER INFORMATION: FMC63-VL NCBI-CAA74660

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 3
<211> LENGTH: 94
<212> TYPE: PRT
<213> ORGANISM: Artificial
<220> FEATURE:
<223> OTHER INFORMATION: humIGKV087 [V1-5*03]

<400> SEQUENCE: 3

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr
                85                  90

<210> SEQ ID NO 4
<211> LENGTH: 94
<212> TYPE: PRT
<213> ORGANISM: Artificial
<220> FEATURE:
<223> OTHER INFORMATION: humIGKV106 [V1-27*01]

<400> SEQUENCE: 4
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                      80

Glu Asp Val Ala Thr Tyr Tyr Cys Gln Lys Tyr Asn Ser Ala
                85                  90
```

<210> SEQ ID NO 5
<211> LENGTH: 94
<212> TYPE: PRT
<213> ORGANISM: Artificial
<220> FEATURE:
<223> OTHER INFORMATION: humIGKV115 [V1-39*01]

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                      80

Glu Asp Phe Ala Thr Tyr Tyr Cys Gln Gln Ser Tyr Ser Thr
                85                  90
```

<210> SEQ ID NO 6
<211> LENGTH: 94
<212> TYPE: PRT
<213> ORGANISM: Artificial
<220> FEATURE:
<223> OTHER INFORMATION: humIGKV094 [V1-12*01]

<400> SEQUENCE: 6

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                      80

Glu Asp Phe Ala Thr Tyr Tyr Cys Gln Gln Ala Asn Ser Phe
                85                  90
```

<210> SEQ ID NO 7
<211> LENGTH: 213
<212> TYPE: PRT
<213> ORGANISM: Artificial
<220> FEATURE:

<223> OTHER INFORMATION: donor amplified cDNA clone#39

<400> SEQUENCE: 7

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Leu Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 8
<211> LENGTH: 214
<212> TYPE: PRT
<213> ORGANISM: Artificial
<220> FEATURE:
<223> OTHER INFORMATION: donor amplified cDNA clone#40

<400> SEQUENCE: 8

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Gly Tyr Tyr
            20                  25                  30

Leu Ala Trp Tyr Gln Gln Lys Pro Gly Lys Val Pro Asn Leu Leu Ile
        35                  40                  45

Tyr Ala Ala Ser Thr Leu Arg Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Leu Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 214
<212> TYPE: PRT
<213> ORGANISM: Artificial
<220> FEATURE:
<223> OTHER INFORMATION: donor amplified cDNA clone#43

<400> SEQUENCE: 9

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 214
<212> TYPE: PRT
<213> ORGANISM: Artificial
<220> FEATURE:
<223> OTHER INFORMATION: donor amplified cDNA clone#44

<400> SEQUENCE: 10

```
Asp Ile Val Met Thr Gln Ser Pro Ser Met Ser Ala Ser Ile Gly
 1               5                  10                  15

Asp Arg Val Thr Ile Thr Cys Arg Ala Ser Gln Gly Ile Thr Ser Trp
            20                  25                  30

Leu Ala Trp Tyr Gln Gln Lys Pro Gly Lys Ala Pro Asn Leu Leu Ile
                35                  40                  45

Tyr Gly Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Tyr Ser Phe Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 11
<211> LENGTH: 98
<212> TYPE: PRT
<213> ORGANISM: Artificial
<220> FEATURE:
<223> OTHER INFORMATION: humIGHV199 [V3-33*01]

<400> SEQUENCE: 11

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
                35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg

<210> SEQ ID NO 12
<211> LENGTH: 98
<212> TYPE: PRT
<213> ORGANISM: Artificial
<220> FEATURE:
<223> OTHER INFORMATION: humIGHV175 [V3-11*01]
```

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 13
<211> LENGTH: 98
<212> TYPE: PRT
<213> ORGANISM: Artificial
<220> FEATURE:
<223> OTHER INFORMATION: humIGHV195 [V3-30*18]

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 14
<211> LENGTH: 98
<212> TYPE: PRT
<213> ORGANISM: Artificial
<220> FEATURE:
<223> OTHER INFORMATION: humIGHV031 [V3-48*01]

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 15
<211> LENGTH: 233
<212> TYPE: PRT
<213> ORGANISM: Artificial
<220> FEATURE:
<223> OTHER INFORMATION: donor amplified cDNA clone#2

<400> SEQUENCE: 15

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Ser Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Asp Leu Leu Ala Ala Pro Thr Ser Arg Gly Tyr Gly Asp Tyr
            100                 105                 110

Leu Tyr Tyr Phe Asp Tyr Trp Gly Gln Gly Thr Leu Val Thr Val Ser
        115                 120                 125

Ser Gly Ser Ala Ser Ala Pro Thr Leu Phe Pro Leu Val Ser Cys Glu
    130                 135                 140

Asn Ser Pro Ser Asp Thr Ser Ser Val Ala Val Gly Cys Leu Ala Gln
145                 150                 155                 160

Asp Phe Leu Pro Asp Ser Ile Thr Phe Ser Trp Lys Tyr Lys Asn Asn
                165                 170                 175

Ser Asp Ile Ser Ser Thr Arg Gly Phe Pro Ser Val Leu Arg Gly Gly
            180                 185                 190

Lys Tyr Ala Ala Thr Ser Gln Val Leu Leu Pro Ser Lys Asp Val Met
        195                 200                 205

Gln Gly Thr Asp Glu His Val Val Cys Lys Val Gln His Pro Asn Gly
    210                 215                 220

Asn Lys Glu Lys Asn Val Pro Leu Pro
225                 230

<210> SEQ ID NO 16
<211> LENGTH: 228
<212> TYPE: PRT
<213> ORGANISM: Artificial
<220> FEATURE:
<223> OTHER INFORMATION: donor amplified cDNA clone#5

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

Tyr Met Ser Trp Ile Arg Gln Ala Pro Gly Lys Gly Leu Glu Trp Val
        35                  40                  45

Ser Tyr Ile Val Ser Ser Gly Thr Asn Lys Tyr Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asp Ser Leu Arg Val Glu Asp Thr Ala Val Tyr Tyr Cys
                            85                  90                  95

Ala Gly Ala Gly Gly Leu Val Ser Ala Ala Gly Arg Ala Ala Pro Arg
                100                 105                 110

Ser Trp Gly Gln Gly Thr Leu Val Thr Val Ser Ser Gly Ser Ala Ser
            115                 120                 125

Ala Pro Thr Leu Phe Pro Leu Val Ser Cys Glu Asn Ser Pro Ser Asp
        130                 135                 140

Thr Ser Ser Val Ala Val Gly Cys Leu Ala Gln Asp Phe Leu Pro Asp
145                 150                 155                 160

Ser Ile Thr Phe Ser Trp Lys Tyr Lys Asn Asn Ser Asp Ile Ser Ser
                165                 170                 175

Thr Arg Gly Phe Pro Ser Val Leu Arg Gly Gly Lys Tyr Ala Ala Thr
            180                 185                 190

Ser Gln Val Leu Leu Pro Ser Lys Asp Val Met Gln Gly Thr Asp Glu
        195                 200                 205

His Val Val Cys Lys Val Gln His Pro Asn Gly Asn Lys Glu Lys Asn
    210                 215                 220

Val Pro Leu Pro
225

<210> SEQ ID NO 17
<211> LENGTH: 222
<212> TYPE: PRT
<213> ORGANISM: Artificial
<220> FEATURE:
<223> OTHER INFORMATION: donor amplified cDNA clone#16

<400> SEQUENCE: 17

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Gly Gly Ser Ser Phe Asp Tyr Trp Gly Gln Gly Thr
            100                 105                 110

Leu Val Thr Val Ser Ser Gly Ser Ala Ser Ala Pro Thr Leu Phe Pro
        115                 120                 125

Leu Val Ser Cys Glu Asn Ser Pro Ser Asp Thr Ser Ser Val Ala Val
    130                 135                 140

Gly Cys Leu Ala Gln Asp Phe Leu Pro Asp Ser Ile Thr Phe Ser Trp
145                 150                 155                 160

Lys Tyr Lys Asn Asn Ser Asp Ile Ser Ser Thr Arg Gly Phe Pro Ser
                165                 170                 175

Val Leu Arg Gly Gly Lys Tyr Ala Ala Thr Ser Gln Val Leu Leu Pro
            180                 185                 190

Ser Lys Asp Val Met Gln Gly Thr Asp Glu His Val Val Cys Lys Val
        195                 200                 205
```

Gln His Pro Asn Gly Asn Lys Glu Lys Asn Val Pro Leu Pro
    210                 215                 220

<210> SEQ ID NO 18
<211> LENGTH: 224
<212> TYPE: PRT
<213> ORGANISM: Artificial
<220> FEATURE:
<223> OTHER INFORMATION: donor amplified cDNA clone#20

<400> SEQUENCE: 18

Gln Val Gln Leu Val Gln Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Tyr Ile Val Ser Ser Gly Thr Asn Lys Tyr Tyr Ala Val Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Met Gly Ala Glu Phe Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

<210> SEQ ID NO 19
<211> LENGTH: 120
<212> TYPE: PRT
<213> ORGANISM: Artificial
<220> FEATURE:
<223> OTHER INFORMATION: VH2

<400> SEQUENCE: 19

Glu Val Gln Leu Val Glu Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Lys Thr Glu Asp Thr Ala Val Tyr Tyr Cys Thr
                    85                  90                  95

Thr His Tyr Tyr Tyr Gly Gly Ser Tyr Ala Met Asp Tyr Trp Gly Gln
                100                 105                 110

Gly Thr Leu Val Thr Val Ser Ser
            115                 120

<210> SEQ ID NO 20
<211> LENGTH: 120
<212> TYPE: PRT
<213> ORGANISM: Artificial
<220> FEATURE:
<223> OTHER INFORMATION: VH5

<400> SEQUENCE: 20

Glu Val Gln Leu Val Glu Ser Gly Gly Leu Val Lys Pro Gly Gly
1               5                   10                  15

Ser Leu Arg Leu Ser Cys Ala Ala Ser Gly Val Ser Leu Pro Asp Tyr
                20                  25                  30

Gly Val Ser Trp Ile Arg Gln Ala Pro Gly Lys Gly Leu Glu Trp Val
            35                  40                  45

Ser Val Ile Trp Gly Ser Glu Thr Thr Tyr Tyr Asn Ser Ala Leu Lys
    50                  55                  60

Ser Arg Phe Thr Ile Ser Arg Asp Asn Ala Lys Asn Ser Leu Tyr Leu
65                  70                  75                  80

Gln Met Asp Ser Leu Arg Val Glu Asp Thr Ala Val Tyr Tyr Cys Ala
                85                  90                  95

Gly His Tyr Tyr Tyr Gly Gly Ser Tyr Ala Met Asp Tyr Trp Gly Gln
                100                 105                 110

Gly Thr Leu Val Thr Val Ser Ser
            115                 120

<210> SEQ ID NO 21
<211> LENGTH: 120
<212> TYPE: PRT
<213> ORGANISM: Artificial
<220> FEATURE:
<223> OTHER INFORMATION: VH16

<400> SEQUENCE: 21

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
                20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
                100                 105                 110

Gly Thr Leu Val Thr Val Ser Ser
            115                 120

<210> SEQ ID NO 22

```
<211> LENGTH: 120
<212> TYPE: PRT
<213> ORGANISM: Artificial
<220> FEATURE:
<223> OTHER INFORMATION: VH20

<400> SEQUENCE: 22

Gln Val Gln Leu Val Gln Ser Gly Gly Gly Leu Val Gln Pro Gly Gly
1               5                   10                  15

Ser Leu Arg Leu Ser Cys Val Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ser Val Ile Trp Gly Ser Glu Thr Thr Tyr Tyr Asn Ser Ala Leu Lys
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 23
<211> LENGTH: 112
<212> TYPE: PRT
<213> ORGANISM: Artificial
<220> FEATURE:
<223> OTHER INFORMATION: VL39

<400> SEQUENCE: 23

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

<210> SEQ ID NO 24
<211> LENGTH: 112
<212> TYPE: PRT
<213> ORGANISM: Artificial
<220> FEATURE:
<223> OTHER INFORMATION: VL40

<400> SEQUENCE: 24

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Val Pro Asn Leu Leu Ile
```

35                  40                  45
Tyr His Thr Ser Arg Leu His Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                     85                  90                  95

Thr Phe Gly Gly Gly Thr Lys Val Glu Ile Lys Arg Thr Val Ala Ala
                    100                 105                 110

<210> SEQ ID NO 25
<211> LENGTH: 112
<212> TYPE: PRT
<213> ORGANISM: Artificial
<220> FEATURE:
<223> OTHER INFORMATION: VL43

<400> SEQUENCE: 25

Asp Ile Val Met Thr Gln Thr Pro Ser Ser Leu Ser Ala Ser Val Gly
 1               5                  10                  15

Asp Arg Val Thr Ile Thr Cys Arg Ala Ser Gln Asp Ile Ser Lys Tyr
                 20                  25                  30

Leu Asn Trp Tyr Gln Gln Lys Pro Gly Lys Ala Pro Lys Leu Leu Ile
             35                  40                  45

Tyr His Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                     85                  90                  95

Thr Phe Gly Pro Gly Thr Lys Val Asp Ile Lys Arg Thr Val Ala Ala
                    100                 105                 110

<210> SEQ ID NO 26
<211> LENGTH: 112
<212> TYPE: PRT
<213> ORGANISM: Artificial
<220> FEATURE:
<223> OTHER INFORMATION: VL44

<400> SEQUENCE: 26

Asp Ile Val Met Thr Gln Ser Pro Ser Ser Met Ser Ala Ser Ile Gly
 1               5                  10                  15

Asp Arg Val Thr Ile Thr Cys Arg Ala Ser Gln Asp Ile Ser Lys Tyr
                 20                  25                  30

Leu Asn Trp Tyr Gln Gln Lys Pro Gly Lys Ala Pro Asn Leu Leu Ile
             35                  40                  45

Tyr His Thr Ser Arg Leu His Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                     85                  90                  95

Thr Phe Gly Gln Gly Thr Lys Leu Glu Ile Lys Arg Thr Val Ala Ala
                    100                 105                 110

<210> SEQ ID NO 27
<211> LENGTH: 10
<212> TYPE: PRT

<213> ORGANISM: Artificial
<220> FEATURE:
<223> OTHER INFORMATION: HCDR1

<400> SEQUENCE: 27

Gly Val Ser Leu Pro Asp Tyr Gly Val Ser
1               5                   10

<210> SEQ ID NO 28
<211> LENGTH: 16
<212> TYPE: PRT
<213> ORGANISM: Artificial
<220> FEATURE:
<223> OTHER INFORMATION: HCDR2

<400> SEQUENCE: 28

Val Ile Trp Gly Ser Glu Thr Thr Tyr Tyr Asn Ser Ala Leu Lys Ser
1               5                   10                  15

<210> SEQ ID NO 29
<211> LENGTH: 12
<212> TYPE: PRT
<213> ORGANISM: Artificial
<220> FEATURE:
<223> OTHER INFORMATION: HCDR3

<400> SEQUENCE: 29

His Tyr Tyr Tyr Gly Gly Ser Tyr Ala Met Asp Tyr
1               5                   10

<210> SEQ ID NO 30
<211> LENGTH: 11
<212> TYPE: PRT
<213> ORGANISM: Artificial
<220> FEATURE:
<223> OTHER INFORMATION: LCDR1

<400> SEQUENCE: 30

Arg Ala Ser Gln Asp Ile Ser Lys Tyr Leu Asn
1               5                   10

<210> SEQ ID NO 31
<211> LENGTH: 7
<212> TYPE: PRT
<213> ORGANISM: Artificial
<220> FEATURE:
<223> OTHER INFORMATION: LCDR2

<400> SEQUENCE: 31

His Thr Ser Arg Leu His Ser
1               5

<210> SEQ ID NO 32
<211> LENGTH: 9
<212> TYPE: PRT
<213> ORGANISM: Artificial
<220> FEATURE:
<223> OTHER INFORMATION: LCDR3

<400> SEQUENCE: 32

Gln Gln Gly Asn Thr Leu Pro Tyr Thr
1               5

<210> SEQ ID NO 33
<211> LENGTH: 120
<212> TYPE: PRT
<213> ORGANISM: Artificial
<220> FEATURE:

<223> OTHER INFORMATION: VH16-G42R

<400> SEQUENCE: 33

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Arg Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 34
<211> LENGTH: 120
<212> TYPE: PRT
<213> ORGANISM: Artificial
<220> FEATURE:
<223> OTHER INFORMATION: VH16-F67L

<400> SEQUENCE: 34

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Leu Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 35
<211> LENGTH: 120
<212> TYPE: PRT
<213> ORGANISM: Artificial
<220> FEATURE:
<223> OTHER INFORMATION: VH16-R71K

<400> SEQUENCE: 35

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

```
Ala Val Ile Trp Gly Ser Glu Thr Thr Tyr Tyr Asn Ser Ala Leu Lys
    50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
                100                 105                 110

Gly Thr Leu Val Thr Val Ser Ser
        115                 120

<210> SEQ ID NO 36
<211> LENGTH: 120
<212> TYPE: PRT
<213> ORGANISM: Artificial
<220> FEATURE:
<223> OTHER INFORMATION: VH16-L78V

<400> SEQUENCE: 36

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
                20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
                100                 105                 110

Gly Thr Leu Val Thr Val Ser Ser
        115                 120

<210> SEQ ID NO 37
<211> LENGTH: 120
<212> TYPE: PRT
<213> ORGANISM: Artificial
<220> FEATURE:
<223> OTHER INFORMATION: VH16-R94K

<400> SEQUENCE: 37

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
                20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110
```

```
Gly Thr Leu Val Thr Val Ser Ser
        115                 120

<210> SEQ ID NO 38
<211> LENGTH: 107
<212> TYPE: PRT
<213> ORGANISM: Artificial
<220> FEATURE:
<223> OTHER INFORMATION: VL43-P44V

<400> SEQUENCE: 38

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 39
<211> LENGTH: 107
<212> TYPE: PRT
<213> ORGANISM: Artificial
<220> FEATURE:
<223> OTHER INFORMATION: VL43-F71Y

<400> SEQUENCE: 39

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 40
<211> LENGTH: 107
<212> TYPE: PRT
<213> ORGANISM: Artificial
<220> FEATURE:
<223> OTHER INFORMATION: VL43-Y87F

<400> SEQUENCE: 40

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
```

```
                20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Asn Thr Leu Pro Tyr
                85                  90                  95

Thr Phe Gly Pro Gly Thr Lys Val Asp Ile Lys
            100                 105

<210> SEQ ID NO 41
<211> LENGTH: 107
<212> TYPE: PRT
<213> ORGANISM: Artificial
<220> FEATURE:
<223> OTHER INFORMATION: VL43-V3Q/T7S

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 42
<211> LENGTH: 120
<212> TYPE: PRT
<213> ORGANISM: Artificial
<220> FEATURE:
<223> OTHER INFORMATION: VH16-Q6E

<400> SEQUENCE: 42

Gln Val Gln Leu Val Glu Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
        50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg His Tyr Tyr Tyr Gly Gly Ser Tyr Ala Met Asp Tyr Trp Gly Gln
            100                 105                 110

Gly Thr Leu Val Thr Val Ser Ser
```

<210> SEQ ID NO 43
<211> LENGTH: 120
<212> TYPE: PRT
<213> ORGANISM: Artificial
<220> FEATURE:
<223> OTHER INFORMATION: VH16-Y32F/R94K

<400> SEQUENCE: 43

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Phe
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial
<220> FEATURE:
<223> OTHER INFORMATION: VH16-R94K/Y96F

<400> SEQUENCE: 44

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Phe Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 45
<211> LENGTH: 120
<212> TYPE: PRT
<213> ORGANISM: Artificial
<220> FEATURE:
<223> OTHER INFORMATION: VH16-R94K/Y97F

<400> SEQUENCE: 45

```
Gln Val Gln Leu Val Gln Ser Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
50                      55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Phe Tyr Gly Gly Ser Tyr Ala Met Asp Tyr Trp Gly Gln
                100                 105                 110

Gly Thr Leu Val Thr Val Ser Ser
            115                 120

<210> SEQ ID NO 46
<211> LENGTH: 120
<212> TYPE: PRT
<213> ORGANISM: Artificial
<220> FEATURE:
<223> OTHER INFORMATION: VH16-R94K/Y98F

<400> SEQUENCE: 46

Gln Val Gln Leu Val Gln Ser Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
50                      55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Phe Gly Gly Ser Tyr Ala Met Asp Tyr Trp Gly Gln
                100                 105                 110

Gly Thr Leu Val Thr Val Ser Ser
            115                 120

<210> SEQ ID NO 47
<211> LENGTH: 120
<212> TYPE: PRT
<213> ORGANISM: Artificial
<220> FEATURE:
<223> OTHER INFORMATION: VH16-R94K/Y100bF

<400> SEQUENCE: 47

Gln Val Gln Leu Val Gln Ser Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
50                      55                  60
```

```
Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys His Tyr Tyr Tyr Gly Gly Ser Phe Ala Met Asp Tyr Trp Gly Gln
            100                 105                 110

Gly Thr Leu Val Thr Val Ser Ser
        115                 120

<210> SEQ ID NO 48
<211> LENGTH: 107
<212> TYPE: PRT
<213> ORGANISM: Artificial
<220> FEATURE:
<223> OTHER INFORMATION: VL43-Y32F

<400> SEQUENCE: 48

Asp Ile Val Met Thr Gln Thr Pro Ser Ser Leu Ser Ala Ser Val Gly
1               5                  10                  15

Asp Arg Val Thr Ile Thr Cys Arg Ala Ser Gln Asp Ile Ser Lys Phe
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 49
<211> LENGTH: 107
<212> TYPE: PRT
<213> ORGANISM: Artificial
<220> FEATURE:
<223> OTHER INFORMATION: VL43-P44I

<400> SEQUENCE: 49

Asp Ile Val Met Thr Gln Thr Pro Ser Ser Leu Ser Ala Ser Val Gly
1               5                  10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 50
<211> LENGTH: 107
<212> TYPE: PRT
<213> ORGANISM: Artificial
<220> FEATURE:
```

<223> OTHER INFORMATION: VL43-P44L

<400> SEQUENCE: 50

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Leu Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 51
<211> LENGTH: 107
<212> TYPE: PRT
<213> ORGANISM: Artificial
<220> FEATURE:
<223> OTHER INFORMATION: VL43-N92A

<400> SEQUENCE: 51

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys
            100                 105

<210> SEQ ID NO 52
<211> LENGTH: 107
<212> TYPE: PRT
<213> ORGANISM: Artificial
<220> FEATURE:
<223> OTHER INFORMATION: VL43-T93V

<400> SEQUENCE: 52

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Val Leu Pro Tyr
                85                  90                  95

Thr Phe Gly Pro Gly Thr Lys Val Asp Ile Lys
            100                 105

<210> SEQ ID NO 53
<211> LENGTH: 107
<212> TYPE: PRT
<213> ORGANISM: Artificial
<220> FEATURE:
<223> OTHER INFORMATION: VL43-T93A

<400> SEQUENCE: 53

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ala Leu Pro Tyr
                85                  90                  95

Thr Phe Gly Pro Gly Thr Lys Val Asp Ile Lys
            100                 105

<210> SEQ ID NO 54
<211> LENGTH: 120
<212> TYPE: PRT
<213> ORGANISM: Artificial
<220> FEATURE:
<223> OTHER INFORMATION: VH16-R94K/Y97W

<400> SEQUENCE: 54

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
                20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Trp Tyr Gly Gly Ser Tyr Ala Met Asp Tyr Trp Gly Gln
            100                 105                 110

Gly Thr Leu Val Thr Val Ser Ser
            115                 120

<210> SEQ ID NO 55
<211> LENGTH: 120
<212> TYPE: PRT
<213> ORGANISM: Artificial
<220> FEATURE:
<223> OTHER INFORMATION: VH16-Y32F/R94K/Y97F -continued

```
<400> SEQUENCE: 55

Gln Val Gln Leu Val Gln Ser Gly Gly Val Val Gln Pro Gly Arg
1               5                   10                  15

Ser Leu Arg Leu Ser Cys Ala Ala Ser Gly Val Ser Leu Pro Asp Phe
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Phe Tyr Gly Gly Ser Tyr Ala Met Asp Tyr Trp Gly Gln
            100                 105                 110

Gly Thr Leu Val Thr Val Ser Ser
        115                 120

<210> SEQ ID NO 56
<211> LENGTH: 107
<212> TYPE: PRT
<213> ORGANISM: Artificial
<220> FEATURE:
<223> OTHER INFORMATION: VL43-Y32F/P44I

<400> SEQUENCE: 56

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Phe
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105

<210> SEQ ID NO 57
<211> LENGTH: 107
<212> TYPE: PRT
<213> ORGANISM: Artificial
<220> FEATURE:
<223> OTHER INFORMATION: VL43-V3Q/T7S/N92A

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
                65                  70                  75                  80
Glu Asp Phe Ala Thr Tyr Tyr Cys Gln Gln Gly Ala Thr Leu Pro Tyr
                    85                  90                  95
Thr Phe Gly Pro Gly Thr Lys Val Asp Ile Lys
                100                 105

<210> SEQ ID NO 58
<211> LENGTH: 107
<212> TYPE: PRT
<213> ORGANISM: Artificial
<220> FEATURE:
<223> OTHER INFORMATION: VL43-V3Q/T7S/Y32F/N92A

<400> SEQUENCE: 58

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Lys Phe
                20                  25                  30
Leu Asn Trp Tyr Gln Gln Lys Pro Gly Lys Ala Pro Lys Leu Leu Ile
            35                  40                  45
Tyr His Thr Ser Arg Leu His Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Ala Thr Leu Pro Tyr
                    85                  90                  95
Thr Phe Gly Pro Gly Thr Lys Val Asp Ile Lys
                100                 105

<210> SEQ ID NO 59
<211> LENGTH: 107
<212> TYPE: PRT
<213> ORGANISM: Artificial
<220> FEATURE:
<223> OTHER INFORMATION: VL43-V3Q/T7S/P44I/N92A

<400> SEQUENCE: 59

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Lys Tyr
                20                  25                  30
Leu Asn Trp Tyr Gln Gln Lys Pro Gly Lys Ala Ile Lys Leu Leu Ile
            35                  40                  45
Tyr His Thr Ser Arg Leu His Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Ala Thr Leu Pro Tyr
                    85                  90                  95
Thr Phe Gly Pro Gly Thr Lys Val Asp Ile Lys
                100                 105

<210> SEQ ID NO 60
<211> LENGTH: 107
<212> TYPE: PRT
<213> ORGANISM: Artificial
<220> FEATURE:
<223> OTHER INFORMATION: VL43-V3Q/T7S/Y32F/P44I/N92A

<400> SEQUENCE: 60
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Phe
            20                  25                  30

Leu Asn Trp Tyr Gln Gln Lys Pro Gly Lys Ala Ile Lys Leu Leu Ile
            35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys
            100                 105
```

<210> SEQ ID NO 61
<211> LENGTH: 107
<212> TYPE: PRT
<213> ORGANISM: Artificial
<220> FEATURE:
<223> OTHER INFORMATION: VL43-F71H

<400> SEQUENCE: 61

```
Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
    50                  55                  60

Ser Gly Ser Gly Thr Asp His Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Pro Gly Thr Lys Val Asp Ile Lys
            100                 105
```

<210> SEQ ID NO 62
<211> LENGTH: 107
<212> TYPE: PRT
<213> ORGANISM: Artificial
<220> FEATURE:
<223> OTHER INFORMATION: VL43-F71S

<400> SEQUENCE: 62

```
Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
            35                  40                  45

Tyr His Thr Ser Arg Leu His Ser Gly Val Pro Ser Arg Phe Ser Gly
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95
```

Thr Phe Gly Pro Gly Thr Lys Val Asp Ile Lys
            100                 105

<210> SEQ ID NO 63
<211> LENGTH: 107
<212> TYPE: PRT
<213> ORGANISM: Artificial
<220> FEATURE:
<223> OTHER INFORMATION: VL43-F71T

<400> SEQUENCE: 63

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Thr Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
            85                  90                  95

Thr Phe Gly Pro Gly Thr Lys Val Asp Ile Lys
            100                 105

<210> SEQ ID NO 64
<211> LENGTH: 450
<212> TYPE: PRT
<213> ORGANISM: Artificial
<220> FEATURE:
<223> OTHER INFORMATION: VH16-- R94K heavy chain

<400> SEQUENCE: 64

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Ser Leu Gly Thr Gln Thr Tyr Ile Cys Asn Val Asn His Lys
        195                 200                 205

Pro Ser Asn Thr Lys Val Asp Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 65
<211> LENGTH: 214
<212> TYPE: PRT
<213> ORGANISM: Artificial
<220> FEATURE:
<223> OTHER INFORMATION: VL43-- V3Q/T7S/P44I/N92A light chain

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Ile Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys Arg Thr Val Ala Ala
```

```
                100             105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 66
<211> LENGTH: 450
<212> TYPE: PRT
<213> ORGANISM: Artificial
<220> FEATURE:
<223> OTHER INFORMATION: VH16-- R94K Y100BF heavy chain

<400> SEQUENCE: 66

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 67
<211> LENGTH: 214
<212> TYPE: PRT
<213> ORGANISM: Artificial
<220> FEATURE:
<223> OTHER INFORMATION: VL43-- V3Q/T7S/Y32F/P44I/N92A light chain

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Phe
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
            165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 68
<211> LENGTH: 450
<212> TYPE: PRT
<213> ORGANISM: Artificial
<220> FEATURE:
<223> OTHER INFORMATION: FMC63 chimeric Heavy Chain

<400> SEQUENCE: 68

```
Glu Val Lys Leu Gln Glu Ser Gly Pro Gly Leu Val Ala Pro Ser Gln
1               5                   10                  15
Ser Leu Ser Val Thr Cys Thr Val Ser Gly Val Ser Leu Pro Asp Tyr
            20                  25                  30
Gly Val Ser Trp Ile Arg Gln Pro Pro Arg Lys Gly Leu Glu Trp Leu
        35                  40                  45
Gly Val Ile Trp Gly Ser Glu Thr Thr Tyr Tyr Asn Ser Ala Leu Lys
    50                  55                  60
Ser Arg Leu Thr Ile Ile Lys Asp Asn Ser Lys Ser Gln Val Phe Leu
65                  70                  75                  80
Lys Met Asn Ser Leu Gln Thr Asp Asp Thr Ala Ile Tyr Tyr Cys Ala
                85                  90                  95
Lys His Tyr Tyr Tyr Gly Gly Ser Tyr Ala Met Asp Tyr Trp Gly Gln
            100                 105                 110
Gly Thr Ser Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
```

```
            305                 310                 315                 320
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 69
<211> LENGTH: 214
<212> TYPE: PRT
<213> ORGANISM: Artificial
<220> FEATURE:
<223> OTHER INFORMATION: FMC63 chimeric Light Chain

<400> SEQUENCE: 69

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 70
<211> LENGTH: 39
<212> TYPE: DNA
<213> ORGANISM: Artificial
<220> FEATURE:
<223> OTHER INFORMATION: Table-1 Fwd Primer

<400> SEQUENCE: 70
gatcggatcc actggtgata ttgtgatgac ycagwctcc                39

<210> SEQ ID NO 71
<211> LENGTH: 36
<212> TYPE: DNA
<213> ORGANISM: Artificial
<220> FEATURE:
<223> OTHER INFORMATION: Table-1 Rev Primer

<400> SEQUENCE: 71
gatcgcggcc gcacactctc ccctgttgaa gctctt                   36

<210> SEQ ID NO 72
<211> LENGTH: 36
<212> TYPE: DNA
<213> ORGANISM: Artificial
<220> FEATURE:
<223> OTHER INFORMATION: Table-2 Fwd Primer I

<400> SEQUENCE: 72
gatcggatcc actggtgagg tgcagctggt ggagtc                   36

<210> SEQ ID NO 73
<211> LENGTH: 36
<212> TYPE: DNA
<213> ORGANISM: Artificial
<220> FEATURE:
<223> OTHER INFORMATION: Table-2 Rev Primer

<400> SEQUENCE: 73
gatcgcggcc gctggaagag gcacgttctt ttcttt                   36

<210> SEQ ID NO 74
<211> LENGTH: 21
<212> TYPE: DNA
<213> ORGANISM: Artificial
<220> FEATURE:
<223> OTHER INFORMATION: CMV-IE Forward

<400> SEQUENCE: 74
cgcaaatggg cggtaggcgt g                                   21

<210> SEQ ID NO 75
<211> LENGTH: 18
<212> TYPE: DNA
<213> ORGANISM: Artificial
<220> FEATURE:
<223> OTHER INFORMATION: BGH Reverse

<400> SEQUENCE: 75
tagaaggcac agtcgagg                                       18

<210> SEQ ID NO 76
<211> LENGTH: 52
<212> TYPE: DNA
<213> ORGANISM: Artificial
<220> FEATURE:
<223> OTHER INFORMATION: VH2 mCDR1 linker Reverse -continued

<400> SEQUENCE: 76
gctcacgccg tagtcgggca ggctcacgcc agacgctgca caggagagtc tc      52

<210> SEQ ID NO 77
<211> LENGTH: 50
<212> TYPE: DNA
<213> ORGANISM: Artificial
<220> FEATURE:
<223> OTHER INFORMATION: VH2 mCDR1 linker Forward

<400> SEQUENCE: 77
ggcgtgagcc tgcccgacta cggcgtgagc tgggtccgcc aggctccagg          50

<210> SEQ ID NO 78
<211> LENGTH: 61
<212> TYPE: DNA
<213> ORGANISM: Artificial
<220> FEATURE:
<223> OTHER INFORMATION: VH2 mCDR2 linker Reverse

<400> SEQUENCE: 78
ggcgctgttg tagtaggttg tctcggagcc ccagatcact gccacccact ccagcccctt    60
g                                                               61

<210> SEQ ID NO 79
<211> LENGTH: 66
<212> TYPE: DNA
<213> ORGANISM: Artificial
<220> FEATURE:
<223> OTHER INFORMATION: VH2 mCDR2 linker Forward

<400> SEQUENCE: 79
ggctccgaga caacctacta caacagcgcc ctgaagagcc gattcaccat ctccagagac    60
aattcc                                                          66

<210> SEQ ID NO 80
<211> LENGTH: 51
<212> TYPE: DNA
<213> ORGANISM: Artificial
<220> FEATURE:
<223> OTHER INFORMATION: VH2 mCDR3 linker Reverse

<400> SEQUENCE: 80
catggcgtag ctgccgccgt agtagtagtg tgtggtacag taatacacgg c         51

<210> SEQ ID NO 81
<211> LENGTH: 54
<212> TYPE: DNA
<213> ORGANISM: Artificial
<220> FEATURE:
<223> OTHER INFORMATION: VH2 mCDR3 linker Forward

<400> SEQUENCE: 81
cactactact acggcggcag ctacgccatg gactactggg gccagggaac cctg     54

<210> SEQ ID NO 82
<211> LENGTH: 52
<212> TYPE: DNA
<213> ORGANISM: Artificial
<220> FEATURE:
<223> OTHER INFORMATION: VH5 mCDR1 linker Reverse

<400> SEQUENCE: 82
gctcacgccg tagtcgggca ggctcacgcc agaggctgca caggagagtc tc      52

<210> SEQ ID NO 83
<211> LENGTH: 51
<212> TYPE: DNA
<213> ORGANISM: Artificial
<220> FEATURE:
<223> OTHER INFORMATION: VH5 mCDR1 linker Forward

<400> SEQUENCE: 83
ggcgtgagcc tgcccgacta cggcgtgagc tggatccgcc aggctccagg g       51

<210> SEQ ID NO 84
<211> LENGTH: 66
<212> TYPE: DNA
<213> ORGANISM: Artificial
<220> FEATURE:
<223> OTHER INFORMATION: VH5 mCDR2 linker Forward

<400> SEQUENCE: 84
ggctccgaga caacctacta caacagcgcc ctgaagagcc gattcaccat ctccagggac   60
aacgcc                                                             66

<210> SEQ ID NO 85
<211> LENGTH: 57
<212> TYPE: DNA
<213> ORGANISM: Artificial
<220> FEATURE:
<223> OTHER INFORMATION: VH5 mCDR3 linker Reverse

<400> SEQUENCE: 85
gtagtccatg gcgtagctgc cgccgtagta gtagtgcccc gcacagtaat aaacggc      57

<210> SEQ ID NO 86
<211> LENGTH: 60
<212> TYPE: DNA
<213> ORGANISM: Artificial
<220> FEATURE:
<223> OTHER INFORMATION: VH5 mCDR3 linker Forward

<400> SEQUENCE: 86
cactactact acggcggcag ctacgccatg gactactggg gccagggaac cctggtcacc   60

<210> SEQ ID NO 87
<211> LENGTH: 51
<212> TYPE: DNA
<213> ORGANISM: Artificial
<220> FEATURE:
<223> OTHER INFORMATION: VH16 mCDR3 linker Reverse

<400> SEQUENCE: 87
catggcgtag ctgccgccgt agtagtagtg tctcgcacag taatacacgg c         51

<210> SEQ ID NO 88
<211> LENGTH: 52
<212> TYPE: DNA
<213> ORGANISM: Artificial
<220> FEATURE:
<223> OTHER INFORMATION: VH20 mCDR1 linker Reverse

<400> SEQUENCE: 88
gctcacgccg tagtcgggca ggctcacgcc agaggctaca caggagagtc tc          52

<210> SEQ ID NO 89
<211> LENGTH: 61
<212> TYPE: DNA
<213> ORGANISM: Artificial

```
<220> FEATURE:
<223> OTHER INFORMATION: VH20 mCDR2 linker Reverse

<400> SEQUENCE: 89
ggcgctgttg tagtaggttg tctcggagcc ccagatcact gaaacccact ccagcccctt    60
c                                                                   61

<210> SEQ ID NO 90
<211> LENGTH: 66
<212> TYPE: DNA
<213> ORGANISM: Artificial
<220> FEATURE:
<223> OTHER INFORMATION: VH20 mCDR2 linker Forward

<400> SEQUENCE: 90
ggctccgaga caacctacta caacagcgcc ctgaagagcc gattcaccat ctccagagac    60
aacgcc                                                              66

<210> SEQ ID NO 91
<211> LENGTH: 51
<212> TYPE: DNA
<213> ORGANISM: Artificial
<220> FEATURE:
<223> OTHER INFORMATION: VH20 mCDR3 linker Reverse

<400> SEQUENCE: 91
catggcgtag ctgccgccgt agtagtagtg tctcgcacag taatacacag c             51

<210> SEQ ID NO 92
<211> LENGTH: 32
<212> TYPE: DNA
<213> ORGANISM: Artificial
<220> FEATURE:
<223> OTHER INFORMATION: SalI adaptor

<400> SEQUENCE: 92
gatcgtcgac gctgaggaga cggtgaccag gg                                  32

<210> SEQ ID NO 93
<211> LENGTH: 37
<212> TYPE: DNA
<213> ORGANISM: Artificial
<220> FEATURE:
<223> OTHER INFORMATION: HindIII VJ2C Forward

<400> SEQUENCE: 93
gatcaagctt gccgccacca tggagacaga cacactc                             37

<210> SEQ ID NO 94
<211> LENGTH: 45
<212> TYPE: DNA
<213> ORGANISM: Artificial
<220> FEATURE:
<223> OTHER INFORMATION: VL39 mCDR2 linker Forward

<400> SEQUENCE: 94
cacaccagcc ggctgcacag cggggtccca tcaaggttca gcggc                    45

<210> SEQ ID NO 95
<211> LENGTH: 51
<212> TYPE: DNA
<213> ORGANISM: Artificial
<220> FEATURE:
<223> OTHER INFORMATION: VL39 mCDR3 linker Reverse

<400> SEQUENCE: 95
```

```
ggtgtagggc agtgtgttgc cttgctggca gtaataagtt gcaaaatcat c          51
```

<210> SEQ ID NO 96
<211> LENGTH: 49
<212> TYPE: DNA
<213> ORGANISM: Artificial
<220> FEATURE:
<223> OTHER INFORMATION: VL39 mCDR3 linker Forward

<400> SEQUENCE: 96

```
cagcaaggca acacactgcc ctacaccttc ggccaaggga ccaaggtgg              49
```

<210> SEQ ID NO 97
<211> LENGTH: 42
<212> TYPE: DNA
<213> ORGANISM: Artificial
<220> FEATURE:
<223> OTHER INFORMATION: VL40 mCDR2 linker Reverse

<400> SEQUENCE: 97

```
gctgtgcagc cggctggtgt gatagatcag gaggttagga ac                    42
```

<210> SEQ ID NO 98
<211> LENGTH: 45
<212> TYPE: DNA
<213> ORGANISM: Artificial
<220> FEATURE:
<223> OTHER INFORMATION: VL40 mCDR2 linker Forward

<400> SEQUENCE: 98

```
cacaccagcc ggctgcacag cggggtccca tctcggttca gcggc                 45
```

<210> SEQ ID NO 99
<211> LENGTH: 51
<212> TYPE: DNA
<213> ORGANISM: Artificial
<220> FEATURE:
<223> OTHER INFORMATION: VL40 mCDR3 linker Reverse

<400> SEQUENCE: 99

```
ggtgtagggc agtgtgttgc cttgctgaca gtaataagtt gcaaaatctt c          51
```

<210> SEQ ID NO 100
<211> LENGTH: 48
<212> TYPE: DNA
<213> ORGANISM: Artificial
<220> FEATURE:
<223> OTHER INFORMATION: VL40 mCDR3 linker Forward

<400> SEQUENCE: 100

```
cagcaaggca acacactgcc ctacaccttc ggcggaggga ccaaggtg              48
```

<210> SEQ ID NO 101
<211> LENGTH: 57
<212> TYPE: DNA
<213> ORGANISM: Artificial
<220> FEATURE:
<223> OTHER INFORMATION: VL43 mCDR1 linker Reverse

<400> SEQUENCE: 101

```
gttcaggtac ttgctgatgt cctggctggc ccggcaagtg atggtgactc tgtctcc    57
```

<210> SEQ ID NO 102
<211> LENGTH: 54
<212> TYPE: DNA
<213> ORGANISM: Artificial

<220> FEATURE:
<223> OTHER INFORMATION: VL43 mCDR1 linker Forward

<400> SEQUENCE: 102
cgggccagcc aggacatcag caagtacctg aactggtatc agcagaaacc aggg    54

<210> SEQ ID NO 103
<211> LENGTH: 42
<212> TYPE: DNA
<213> ORGANISM: Artificial
<220> FEATURE:
<223> OTHER INFORMATION: VL43 mCDR2 linker Reverse

<400> SEQUENCE: 103
gctgtgcagc cggctggtgt gatagatcag gagcttaggg gc    42

<210> SEQ ID NO 104
<211> LENGTH: 45
<212> TYPE: DNA
<213> ORGANISM: Artificial
<220> FEATURE:
<223> OTHER INFORMATION: VL43 mCDR2 linker Forward

<400> SEQUENCE: 104
cacaccagcc ggctgcacag cggggtccca tcaaggttca gtggc    45

<210> SEQ ID NO 105
<211> LENGTH: 51
<212> TYPE: DNA
<213> ORGANISM: Artificial
<220> FEATURE:
<223> OTHER INFORMATION: VL43 mCDR3 linker Reverse

<400> SEQUENCE: 105
ggtgtagggc agtgtgttgc cttgctgaca gtagtaagtt gcaaaatctt c    51

<210> SEQ ID NO 106
<211> LENGTH: 49
<212> TYPE: DNA
<213> ORGANISM: Artificial
<220> FEATURE:
<223> OTHER INFORMATION: VL43 mCDR3 linker Forward

<400> SEQUENCE: 106
cagcaaggca acacactgcc ctacaccttc ggccctggga ccaaagtgg    49

<210> SEQ ID NO 107
<211> LENGTH: 57
<212> TYPE: DNA
<213> ORGANISM: Artificial
<220> FEATURE:
<223> OTHER INFORMATION: VL44 mCDR1 linker Reverse

<400> SEQUENCE: 107
gttcaggtac ttgctgatgt cctggctggc ccgacaagtg atggtgactc tgtctcc    57

<210> SEQ ID NO 108
<211> LENGTH: 42
<212> TYPE: DNA
<213> ORGANISM: Artificial
<220> FEATURE:
<223> OTHER INFORMATION: VL44 mCDR2 linker Reverse

<400> SEQUENCE: 108
gctgtgcagc cggctggtgt gatagatcag gaggttaggg gc    42

-continued

<210> SEQ ID NO 109
<211> LENGTH: 45
<212> TYPE: DNA
<213> ORGANISM: Artificial
<220> FEATURE:
<223> OTHER INFORMATION: VL44 mCDR2 linker Forward

<400> SEQUENCE: 109
cacaccagcc ggctgcacag cggggtccca tcaaggttca gcggc                45

<210> SEQ ID NO 110
<211> LENGTH: 51
<212> TYPE: DNA
<213> ORGANISM: Artificial
<220> FEATURE:
<223> OTHER INFORMATION: VL44 mCDR3 linker Reverse

<400> SEQUENCE: 110
ggtgtagggc agtgtgttgc cttgctgaca ataataagtt gcaaaatctt c          51

<210> SEQ ID NO 111
<211> LENGTH: 49
<212> TYPE: DNA
<213> ORGANISM: Artificial
<220> FEATURE:
<223> OTHER INFORMATION: VL44 mCDR3 linker Forward

<400> SEQUENCE: 111
cagcaaggca acacactgcc ctacaccttt ggccagggga ccaagttgg            49

<210> SEQ ID NO 112
<211> LENGTH: 38
<212> TYPE: DNA
<213> ORGANISM: Artificial
<220> FEATURE:
<223> OTHER INFORMATION: NotI Kappa Reverse

<400> SEQUENCE: 112
gatcgcggcc gcttatcaac actctcccct gttgaagc                         38

<210> SEQ ID NO 113
<211> LENGTH: 39
<212> TYPE: DNA
<213> ORGANISM: Artificial
<220> FEATURE:
<223> OTHER INFORMATION: Table-2 Fwd Primer II

<400> SEQUENCE: 113
gatcggatcc actggtcagg tycagctkgt gcagtctgg                        39

<210> SEQ ID NO 114
<211> LENGTH: 450
<212> TYPE: PRT
<213> ORGANISM: Artificial
<220> FEATURE:
<223> OTHER INFORMATION: VH16-R94K/S298A heavy chain

<400> SEQUENCE: 114

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ala Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 115
<211> LENGTH: 450
<212> TYPE: PRT

<213> ORGANISM: Artificial
<220> FEATURE:
<223> OTHER INFORMATION: VH16-R94K/E269D/S298A heavy chain

<400> SEQUENCE: 115

| | | | | | | | | | | | | | | |
|---|---|---|---|---|---|---|---|---|---|---|---|---|---|---|
| Gln | Val | Gln | Leu | Val | Gln | Ser | Gly | Gly | Gly | Val | Val | Gln | Pro | Gly | Arg |
| 1 | | | | 5 | | | | | 10 | | | | | 15 | |
| Ser | Leu | Arg | Leu | Ser | Cys | Ala | Ala | Ser | Gly | Val | Ser | Leu | Pro | Asp | Tyr |
| | | | 20 | | | | | 25 | | | | | 30 | | |
| Gly | Val | Ser | Trp | Val | Arg | Gln | Ala | Pro | Gly | Lys | Gly | Leu | Glu | Trp | Val |
| | | | 35 | | | | | 40 | | | | | 45 | | |
| Ala | Val | Ile | Trp | Gly | Ser | Glu | Thr | Thr | Tyr | Tyr | Asn | Ser | Ala | Leu | Lys |
| | 50 | | | | | 55 | | | | | 60 | | | | |
| Ser | Arg | Phe | Thr | Ile | Ser | Arg | Asp | Asn | Ser | Lys | Asn | Thr | Leu | Tyr | Leu |
| 65 | | | | | 70 | | | | | 75 | | | | | 80 |
| Gln | Met | Asn | Ser | Leu | Arg | Ala | Glu | Asp | Thr | Ala | Val | Tyr | Tyr | Cys | Ala |
| | | | | 85 | | | | | 90 | | | | | 95 | |
| Lys | His | Tyr | Tyr | Tyr | Gly | Gly | Ser | Tyr | Ala | Met | Asp | Tyr | Trp | Gly | Gln |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Lys | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Asp |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | | 275 | | | | | 280 | | | | | 285 | | |
| Asn | Ala | Lys | Thr | Lys | Pro | Arg | Glu | Glu | Gln | Tyr | Asn | Ala | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Asp | Glu | Leu | Thr | Lys | Asn | Gln | Val | Ser | Leu |
| | | | 355 | | | | | 360 | | | | | 365 | | |
| Thr | Cys | Leu | Val | Lys | Gly | Phe | Tyr | Pro | Ser | Asp | Ile | Ala | Val | Glu | Trp |
| | 370 | | | | | 375 | | | | | 380 | | | | |
| Glu | Ser | Asn | Gly | Gln | Pro | Glu | Asn | Asn | Tyr | Lys | Thr | Thr | Pro | Pro | Val |
| 385 | | | | | 390 | | | | | 395 | | | | | 400 |

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 116
<211> LENGTH: 450
<212> TYPE: PRT
<213> ORGANISM: Artificial
<220> FEATURE:
<223> OTHER INFORMATION: VH16-R94K/S298A/S324N heavy chain

<400> SEQUENCE: 116

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ala Thr Tyr Arg
            290                 295                 300

```
Val Val Ser Val Leu Thr Val Leu His Gln Asp Trp Leu Asn Gly Lys
305                 310                 315                 320

Glu Tyr Lys Cys Lys Val Asn Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 117
<211> LENGTH: 450
<212> TYPE: PRT
<213> ORGANISM: Artificial
<220> FEATURE:
<223> OTHER INFORMATION: VH16-R94K/E269D/S298A/S324N heavy chain

<400> SEQUENCE: 117

Gln Val Gln Leu Val Gln Ser Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
                210                 215                 220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Asp
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ala Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Asn Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 118
<211> LENGTH: 450
<212> TYPE: PRT
<213> ORGANISM: Artificial
<220> FEATURE:
<223> OTHER INFORMATION: VH16-R94K/S324N heavy chain

<400> SEQUENCE: 118

Gln Val Gln Leu Val Glu Ser Gly Gly Gly Val Val Gln Pro Gly Arg
1               5                   10                  15

Ser Leu Arg Leu Ser Cys Ala Ala Ser Gly Val Ser Leu Pro Asp Tyr
                20                  25                  30

Gly Val Ser Trp Val Arg Gln Ala Pro Gly Lys Gly Leu Glu Trp Val
                35                  40                  45

Ala Val Ile Trp Gly Ser Glu Thr Thr Tyr Tyr Asn Ser Ala Leu Lys
                50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
                100                 105                 110

Gly Thr Leu Val Thr Val Ser Ser Ala Ser Thr Lys Gly Pro Ser Val
                115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Asn Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 119
<211> LENGTH: 450
<212> TYPE: PRT
<213> ORGANISM: Artificial
<220> FEATURE:
<223> OTHER INFORMATION: VH16-R94K/K274Q heavy chain

<400> SEQUENCE: 119

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30
```

-continued

```
Gly Val Ser Trp Val Arg Gln Ala Pro Gly Lys Gly Leu Glu Trp Val
             35                  40                  45

Ala Val Ile Trp Gly Ser Glu Thr Thr Tyr Tyr Asn Ser Ala Leu Lys
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Lys His Tyr Tyr Tyr Gly Gly Ser Tyr Ala Met Asp Tyr Trp Gly Gln
        100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
             165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
             195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
             245                 250                 255

Ser Arg Thr Pro Glu Val Thr Cys Val Val Val Asp Val Ser His Glu
             260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
             325                 330                 335

Lys Thr Ile Ser Lys Ala Lys Gly Gln Pro Arg Glu Pro Gln Val Tyr
             340                 345                 350

Thr Leu Pro Pro Ser Arg Asp Glu Leu Thr Lys Asn Gln Val Ser Leu
             355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
             405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
             435                 440                 445

Gly Lys
450
```

<210> SEQ ID NO 120
<211> LENGTH: 450
<212> TYPE: PRT
<213> ORGANISM: Artificial
<220> FEATURE:
<223> OTHER INFORMATION: VH16-R94K/N276K heavy chain

<400> SEQUENCE: 120

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Lys Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

-continued

Thr Cys Leu Val Lys Gly Phe Tyr Pro Ser Asp Ile Ala Val Glu Trp
           370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
           420                 425                 430

Glu Ala Leu His Asn His Tyr Thr Gln Lys Ser Leu Ser Leu Ser Pro
               435                 440                 445

Gly Lys
    450

<210> SEQ ID NO 121
<211> LENGTH: 450
<212> TYPE: PRT
<213> ORGANISM: Artificial
<220> FEATURE:
<223> OTHER INFORMATION: VH16-R94K/K334R heavy chain

<400> SEQUENCE: 121

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys His Tyr Tyr Tyr Gly Gly Ser Tyr Ala Met Asp Tyr Trp Gly Gln
        100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His

```
                    275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Arg Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 122
<211> LENGTH: 450
<212> TYPE: PRT
<213> ORGANISM: Artificial
<220> FEATURE:
<223> OTHER INFORMATION: VH16-R94K/K274Q/N276K heavy chain

<400> SEQUENCE: 122

Gln Val Gln Leu Val Gln Ser Gly Gly Gly Val Val Gln Pro Gly Arg
1               5                   10                  15
Ser Leu Arg Leu Ser Cys Ala Ala Ser Gly Val Ser Leu Pro Asp Tyr
            20                  25                  30
Gly Val Ser Trp Val Arg Gln Ala Pro Gly Lys Gly Leu Glu Trp Val
        35                  40                  45
Ala Val Ile Trp Gly Ser Glu Thr Thr Tyr Tyr Asn Ser Ala Leu Lys
    50                  55                  60
Ser Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys His Tyr Tyr Tyr Gly Gly Ser Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Lys Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 123
<211> LENGTH: 450
<212> TYPE: PRT
<213> ORGANISM: Artificial
<220> FEATURE:
<223> OTHER INFORMATION: VH16-R94K/K274Q/N276K/K334R heavy chain

<400> SEQUENCE: 123

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95
```

```
Lys His Tyr Tyr Tyr Gly Ser Tyr Ala Met Asp Tyr Trp Gly Gln
                100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Lys Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Arg Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 124
<211> LENGTH: 450
<212> TYPE: PRT
<213> ORGANISM: Artificial
<220> FEATURE:
<223> OTHER INFORMATION: VH16-R94K(1133) heavy chain

<400> SEQUENCE: 124

Gln Val Gln Leu Val Gln Ser Gly Gly Gly Val Val Gln Pro Gly Arg
```

-continued

```
1               5               10              15
Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
            35                  40                  45

Ala Val Ile Trp Gly Ser Glu Thr Thr Tyr Tyr Asn Ser Ala Leu Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Gln Phe Lys Trp Tyr Val Asp Gly Val Glu Val His
            275                 280                 285

Asn Ala Lys Thr Lys Pro Arg Glu Glu Gln Tyr Asn Ser Thr Phe Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Ser Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Ile Phe Ser Cys Ser Val Met His
            420                 425                 430
```

```
Glu Ala Leu His Asn Arg Phe Thr Gln Lys Ser Leu Ser Leu Ser Pro
            435                 440                 445

Gly Lys
    450

<210> SEQ ID NO 125
<211> LENGTH: 556
<212> TYPE: PRT
<213> ORGANISM: Homo sapiens
<220> FEATURE:
<221> NAME/KEY: MISC_FEATURE
<222> LOCATION: (1)..(556)
<223> OTHER INFORMATION: human CD19

<400> SEQUENCE: 125

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320
```

```
Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
            485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 126
<211> LENGTH: 5
<212> TYPE: PRT
<213> ORGANISM: Artificial Sequence
<220> FEATURE:
<223> OTHER INFORMATION: Glycine Serine Linker

<400> SEQUENCE: 126

Gly Gly Gly Gly Ser
1               5
```